United States Patent
Uesugi et al.

(10) Patent No.: US 10,328,064 B2
(45) Date of Patent: Jun. 25, 2019

(54) COMPOSITIONS OF FATOSTATIN BASED HETEROCYCLIC COMPOUNDS AND USES THEREOF

(71) Applicant: FGH BIOTECH, INC., Houston, TX (US)

(72) Inventors: Motonari Uesugi, Osaka (JP); Joel Huff, Spring Branch, TX (US)

(73) Assignee: FGH BIOTECH, INC., Houston, TX (US)

( * ) Notice: Subject to any disclaimer, the term of this patent is extended or adjusted under 35 U.S.C. 154(b) by 0 days.

(21) Appl. No.: 15/539,647

(22) PCT Filed: Dec. 23, 2015

(86) PCT No.: PCT/US2015/000221
§ 371 (c)(1),
(2) Date: Jun. 23, 2017

(87) PCT Pub. No.: WO2016/105491
PCT Pub. Date: Jun. 30, 2016

(65) Prior Publication Data
US 2018/0000801 A1    Jan. 4, 2018

Related U.S. Application Data

(60) Provisional application No. 62/096,121, filed on Dec. 23, 2014.

(51) Int. Cl.
| | |
|---|---|
| A61K 31/44 | (2006.01) |
| C07D 401/14 | (2006.01) |
| C07D 401/04 | (2006.01) |
| C07D 413/04 | (2006.01) |
| C07D 417/04 | (2006.01) |
| C07D 417/06 | (2006.01) |
| C07D 417/14 | (2006.01) |
| A61K 31/41 | (2006.01) |
| A61K 31/422 | (2006.01) |
| A61K 31/427 | (2006.01) |
| A61K 31/454 | (2006.01) |
| A61K 31/4545 | (2006.01) |
| A61K 31/497 | (2006.01) |
| A61P 3/06 | (2006.01) |
| A61P 35/00 | (2006.01) |

(52) U.S. Cl.
CPC .............. *A61K 31/44* (2013.01); *A61K 31/41* (2013.01); *A61K 31/422* (2013.01); *A61K 31/427* (2013.01); *A61K 31/454* (2013.01); *A61K 31/4545* (2013.01); *A61K 31/497* (2013.01); *A61P 3/06* (2018.01); *A61P 35/00* (2018.01); *C07D 401/04* (2013.01); *C07D 401/14* (2013.01); *C07D 413/04* (2013.01); *C07D 417/04* (2013.01); *C07D 417/06* (2013.01); *C07D 417/14* (2013.01)

(58) Field of Classification Search
CPC ..... A61K 31/44; C07D 401/04; C07D 401/14
USPC .......................................................... 514/277
See application file for complete search history.

(56) References Cited

U.S. PATENT DOCUMENTS

| | | | |
|---|---|---|---|
| 6,355,635 B1 * | 3/2002 | Elliott | C07D 401/04 514/231.5 |
| 8,207,196 B2 | 6/2012 | Uesugi et al. | |
| 8,778,976 B2 | 7/2014 | Uesugi et al. | |
| 8,927,578 B2 | 1/2015 | Uesugi et al. | |
| 9,085,566 B2 | 7/2015 | Uesugi et al. | |
| 9,187,485 B2 | 11/2015 | Uesugi et al. | |
| 9,212,179 B2 | 12/2015 | Uesugi et al. | |
| 9,233,941 B2 | 1/2016 | Uesugi et al. | |

(Continued)

FOREIGN PATENT DOCUMENTS

| | | |
|---|---|---|
| IN | 2816/MUM/2013 | 5/2016 |
| JP | 1996181009 | 1/1998 |

(Continued)

OTHER PUBLICATIONS de Barros et al. *Anais da Associacao Brasileira de Quimica* (2001), 50(4), 162-165 (abstract only).
Bellale, Eknath et al., "Diarylthiazole: an antimycobacterial scaffold potentially targeting PrrB-PrrA two-component system", Journal of Medicinal Chemistry Jun. 26, 2014, vol. 57, No. 15, pp. 6572-6582.
Chen, Yet al., "Copper catalyzed synthesis of 1-aryl-1,2,3-triazoles from aryl iodides, alkynes, and sodium azide," Journal of Organometallic Chemistry 2014, 749(31):215-218.

(Continued)

*Primary Examiner* — Kahsay Habte
(74) *Attorney, Agent, or Firm* — Squire Patton Boggs (US) LLP

(57) ABSTRACT

The present invention relates to compounds, pharmaceutical compositions and formulations that have a structure (I). The compounds comprise a heterocyclic ring where W, X, Y, and Z generally and independently are S, N or C with the proviso that at least 2 of these positions in the ring are other than carbon. A pyridine or a substituted pyridine A ring and a phenyl or a substituted phenyl B ring are covalently bonded to the heterocyclic ring. Further provided are methods for treating a metabolic disorder, cell proliferative disease, reducing body weight or increasing thermogenesis during weight loss with the compounds of structure as described or pharmaceutically acceptable salt or stereoisomer thereof or both.

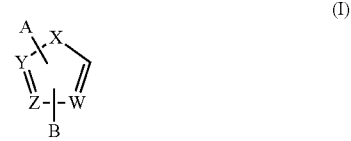

(I)

19 Claims, 50 Drawing Sheets

(56) References Cited

U.S. PATENT DOCUMENTS

| | | | |
|---|---|---|---|
| 9,713,613 B2 | 7/2017 | Uesugi et al. |
| 2002/0065289 A1 | 5/2002 | Kordik et al. |
| 2002/0111353 A1 | 8/2002 | Ledeboer et al. |
| 2003/0055085 A1 | 3/2003 | Wagenen et al. |
| 2004/0229927 A1 | 11/2004 | Sircar et al. |
| 2008/0280869 A1 | 11/2008 | Almstead et al. |
| 2011/0021771 A1 | 1/2011 | Mallais et al. |
| 2011/0112282 A1 | 5/2011 | Roehrig et al. |
| 2012/0252796 A1 | 10/2012 | Pingali et al. |
| 2013/0018053 A1 | 1/2013 | Zhou et al. |
| 2014/0038984 A1 | 2/2014 | Uesugi et al. |
| 2014/0045845 A1 | 2/2014 | Uesugi et al. |
| 2014/0235646 A1 | 8/2014 | Uesugi et al. |
| 2015/0065519 A1 | 3/2015 | Chakravarty et al. |
| 2015/0210705 A1 | 7/2015 | Jacobsen et al. |
| 2015/0307501 A1 | 10/2015 | Uesugi et al. |
| 2016/0128985 A1 | 5/2016 | Uesugi et al. |
| 2018/0028518 A1 | 2/2018 | Bernales et al. |
| 2018/0051013 A1 | 2/2018 | Pujala et al. |
| 2018/0291013 A1 | 10/2018 | Uesugi et al. |

FOREIGN PATENT DOCUMENTS

| | | |
|---|---|---|
| WO | WO 1994/22846 A1 | 10/1994 |
| WO | WO 2005/044194 A2 | 5/2005 |
| WO | WO 2006/024642 A1 | 3/2006 |
| WO | WO 2007/001973 A1 | 1/2007 |
| WO | WO 2007/052843 | 5/2007 |
| WO | WO 2008/090382 | 7/2008 |
| WO | WO 2008/097835 A2 | 8/2008 |
| WO | WO 2009/027346 | 3/2009 |
| WO | WO 2015/031710 A1 | 3/2015 |
| WO | WO 2016/073826 A1 | 5/2016 |
| WO | WO 2016/105491 A1 | 6/2016 |
| WO | WO 2016/106331 | 6/2016 |
| WO | WO 2018/049080 | 3/2018 |

OTHER PUBLICATIONS

U.S. Appl. No. 16/097,211, filed Nov. 2, 2017, FGH Biotech, Inc.
Compounds comprising pyrazole, STN database accessed on Jan. 18, 2019, 236 pages.
Compounds comprising triazole, STN database accessed on Jan. 15, 2019, 26 pages.
International Search Report and Written Opinion dated May 12, 2016 in International Patent Application No. PCT/US2015/000221, 7 pages.
Krishnan et al., "Synthesis of Aryltriazolyl Derivatives," Indian Journal of Chemistry, vol. 26B, Jul. 1987, pp. 616-619.
Schweinfurth et al. "1,3-Dipolar cycloaddition of alkynes to azides. Construction of operationally functional metal responsive fluorophores" Chemical Communications (Cambridge, United Kingdom) (2008), (19), 2203-2205.
Shi et al. "Facile derivatization of pyridyloxazole-type fluorophore via click chemistry" Chemistry Letters (2007), 36(9), 1142-1143.
Ueda, S. et al. Angew. Chem. Int. Ed. 2011, 38, 8944.
Vachal et al., "Highly selective and potent agonists of sphingosine-1-phosphate 1 (S1P$_1$ receptor," *Bioorganic & Medicinal Chemistry Letters*, 16:3684-3687, 2006.
Xu et al., "Design, synthesis, and biologic evaluation of some novel N-arylpyrazole derivatives as cytotxic agents," Medicinal Chemistry Research, 2013, vol. 22, 5610-5616.
De Barros et al. Anais da Associacao Brasileira de Quimica (2001), 50(4), 162-165.

\* cited by examiner

FIG. 30

COMPOSITIONS OF FATOSTATIN BASED HETEROCYCLIC COMPOUNDS AND USES THEREOF

CROSS-REFERENCE TO RELATED APPLICATIONS

This international application claims benefit of priority under 35 U.S.C. § 119(e) of provisional application U.S. Ser. No. 62/096,121, filed Dec. 23, 2014, the entirety of which is hereby incorporated by reference.

BACKGROUND OF THE INVENTION

Field of the Invention

The present invention generally relates to the fields of medicinal chemistry and therapeutic compounds. Specifically, the present invention relates to heterocyclic analogs and derivatives of fatostatin A and therapeutic uses thereof.

Description of the Related Art

Metabolic syndrome covers many cardiovascular risk factors including hypertension, dyslipidaemia, obesity, type 2 diabetes, pancreatic β-cell dysfunction, and atherosclerosis. A diet varying in fat or carbohydrate contents contributes to energy metabolism of animals including humans. Long chain fatty acids are major source of energy and important components of the lipids that comprise the cellular membranes. They are derived from food and synthesized de novo from acetyl-CoA. Cholesterol is also derived from food and synthesized from acetyl-CoA. The conversion of carbohydrates into acylglycerides through de novo fatty acid and cholesterol synthesis involves at least 12 and 23 enzymatic reactions, respectively. Expression levels of the genes encoding these enzymes are controlled by three transcription factors, designated sterol regulatory element-binding proteins (SREBPs), SREBP-1a, -1c and SREBP-2. These membrane-bound proteins are members of a class of the basic helix-loop-helix leucin zipper family of transcription factors. Unlike other leucin zipper members of transcription factors, SREBPs are synthesized as an ER-membrane-bound precursor, which needs to be proteolytically released by two proteases bound to the Golgi membrane, Site-1 and Site-2 proteases, in order to activate transcription of target genes in the nucleus.

The proteolytic activation of SREBPs is tightly regulated by sterols through the interaction with SREBP cleavage-activating protein (SCAP), an ER-membrane-bound escort protein of SREBPs. When sterols accumulate in the ER membranes, the SCAP/SREBP complex fails to exit the ER to the Golgi, and thereby the proteolytic processing of SREBPs is suppressed. SREBPs are key lipogenic transcription factors that govern the homeostasis of fat metabolism. Fatostatin is identified as an inhibitor of SREBP activation. Fatostatin impairs the proteolytic activation of SREBPs, thereby decreasing the transcription of lipogenic genes in cells.

The prior art is deficient in development of novel compositions and methods of use in the regulation of sterol regulatory element-binding protein. Particularly, the prior art is deficient in heterocyclic fatostatin derivatives or analogs useful for treating metabolic disorders The present invention fulfills this long standing need and desire in the art.

SUMMARY OF THE INVENTION

The present invention is directed to a compound having the chemical structure:

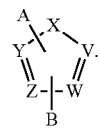

The A group may be a substituted or unsubstituted pyridine, a substituted or unsubstituted piperidine, a substituted or unsubstituted pyrrolidine, a substituted or unsubstituted indole, or a natural or an unnatural amino acid. The B group may be a substituted or unsubstituted phenyl ring, a substituted or unsubstituted pyridine, a substituted or unsubstituted piperidine, a substituted or unsubstituted cycloalkyl ring, a substituted or unsubstituted heterocycloalkyl ring. The B group in combination with V and W may form a benzothiazole ring.

The W substituent may be N or C. The X substituent may be O, S, N or C. The Y substituent may be N or C. The Z substituent may be N or C. At least two of the W, X, Y, and Z substituents are other than carbon.

The present invention also is directed to a method for treating a metabolic disorder in an animal in need thereof, comprising the step of: administering to the animal a therapeutically effective amount of at least one compound disclosed in this invention, or a pharmaceutically acceptable salt or a stereoisomer thereof or a combination thereof.

The present invention is directed further to a method for treating a cell proliferative disease in an animal in need thereof, comprising the step of: administering to the animal a therapeutically effective amount of at least one compound disclosed in this invention, or a pharmaceutically acceptable salt or a stereoisomer thereof or a combination thereof.

The present invention is directed further still to a method for reducing body weight in an animal in need thereof, comprising the step of: administering to the animal a therapeutically effective amount of at least one compound disclosed in this invention, or a pharmaceutically acceptable salt or a stereoisomer thereof or a combination thereof.

The present invention is directed further still to a method for increasing thermogenesis without reducing lean body mass during weight loss in an animal, comprising the step of: administering to the animal a therapeutically effective amount of at least one compound disclosed in this invention, or a pharmaceutically acceptable salt or a stereoisomer thereof or a combination thereof.

BRIEF DESCRIPTION OF THE DRAWINGS

For a more complete understanding of the present invention, reference is now made to the following descriptions taken in conjunction with the accompanying drawings.

FIG. 12B illustrates the synthesis of thiazole derivatives 146a-146e from compound 79a.

FIG. 30 illustrates the synthesis of thiazoles 154a-154g from pyridine 151.

DETAILED DESCRIPTION OF THE INVENTION

Figure 1:
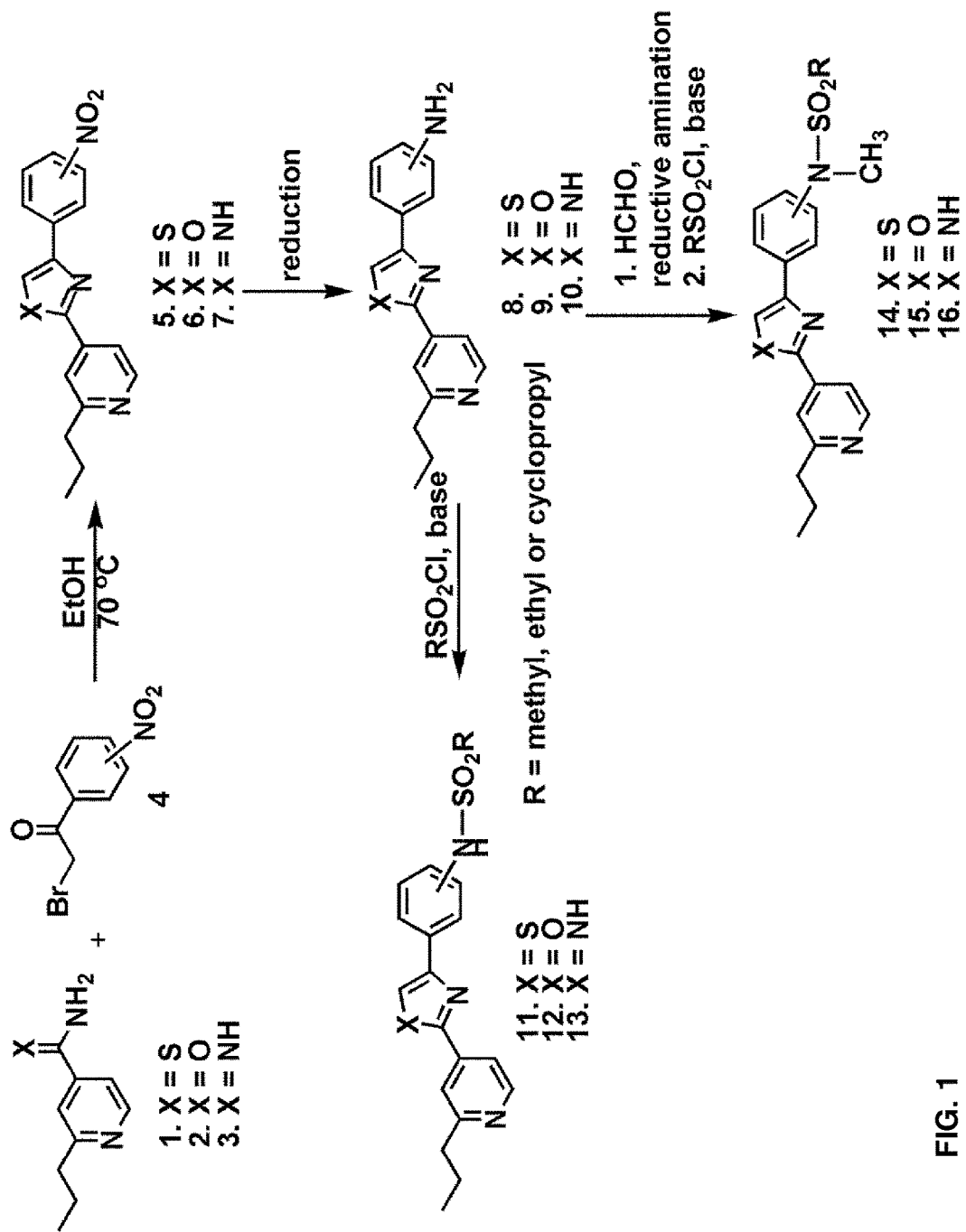
FIG. 1 illustrates a general strategy for the synthesis of the compounds disclosed herein. Synthetic method is shown for the sulfonamides 11-16 as an example.

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

Embodiments of the Invention

In one embodiment of the present invention, there is a compound having the chemical structure:

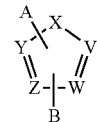

wherein A is a substituted or unsubstituted pyridine, a substituted or unsubstituted piperidine, a substituted or unsubstituted pyrrolidine, a substituted or unsubstituted indole, or a natural or an unnatural amino acid; B is a substituted or unsubstituted phenyl ring, a substituted or unsubstituted pyridine, a substituted or unsubstituted piperidine, a substituted or unsubstituted cycloalkyl ring, a substituted or unsubstituted heterocycloalkyl ring or wherein B in combination with V and W form a benzothiazole ring; W is N or C; X is N or C; X is O S, N or C; Y is N or C; Z is N or C; and wherein at least two of W, X, Y, and Z are other than carbon.

In one preferred aspect of this embodiment, the chemical structure is

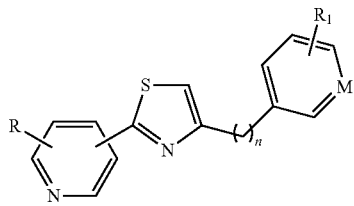

wherein n=0, 1 or 2; M is N or CH; R is ethyl or n-propyl, isopropyl, —O—$C_{1-3}$ alkoxy, a substituted or unsubstituted pyrrolidine, or a substituted or unsubstituted morpholine; $R_1$ is H, halogen, —OH, —O—$C_{1-3}$ alkoxy, —OC(O)$R_2$, or —N$R_3R_4$; $R_2$ is $C_1$-$C_3$ alkyl or aryl; $R_3$ is H, $C_1$-$C_3$ alkyl, alkylcyclopropane, cyclohexyl, benzyl or —SO$_2$—$R_5$; $R_4$ is H, $C_1$-$C_3$ alkyl, or —SO$_2$—$R_5$; and $R_5$ is alkyl, cycloalkyl, aryl or heteroaryl. In one preferred aspect of this embodiment, the chemical structure is

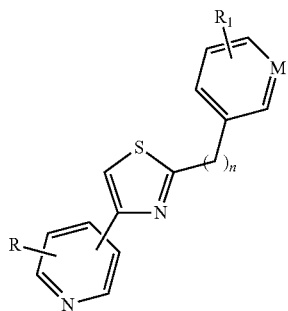

wherein n=0, 1 or 2; M is N or CH; R is ethyl, n-propyl, isopropyl, —O—$C_{1-3}$ alkoxy, a substituted or unsubstituted pyrrolidine, or a substituted or unsubstituted morpholine; $R_1$ is H, halogen, —OH, —O—$C_{1-3}$ alkoxy, —OC(O)$R_2$, or —$NR_3R_4$; $R_2$ is $C_1$-$C_3$ alkyl or aryl; $R_3$ is H, $C_1$-$C_3$ alkyl, alkylcyclopropane, cyclohexyl, benzyl, or —$SO_2$—$R_5$; $R_4$ is H, $C_1$-$C_3$ alkyl, or —$SO_2$—$R_5$; and $R_5$ is alkyl, cycloalkyl, aryl or heteroaryl.

In another preferred aspect of this embodiment, the chemical structure is

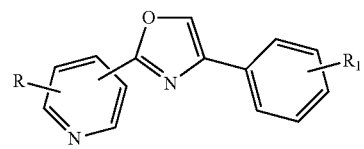

wherein R is ethyl, n-propyl, isopropyl, —O—$C_{1-3}$ alkoxy, a substituted or unsubstituted pyrrolidine, or a substituted or unsubstituted morpholine; $R_1$ is H, halogen, —OH, —O—$C_{1-3}$ alkoxy, —OC(O)$R_2$, or —$NR_3R_4$; $R_2$ is $C_1$-$C_3$ alkyl or aryl; $R_3$ is H, $C_1$-$C_3$ alkyl, alkylcyclopropane, cyclohexyl, benzyl, or —$SO_2$—$R_5$; $R_4$ is H, $C_1$-$C_3$ alkyl, or —$SO_2$—$R_5$; and $R_5$ is alkyl, cycloalkyl, aryl or heteroaryl.

In yet another preferred aspect of this embodiment, the chemical structure is

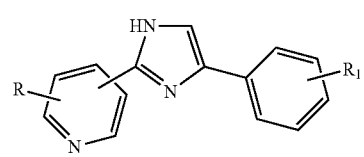

wherein R is ethyl, n-propyl, isopropyl, —O—$C_{1-3}$ alkoxy, a substituted or unsubstituted pyrrolidine, or a substituted or unsubstituted morpholine; $R_1$ is H, halogen, —OH, —O—$C_{1-3}$ alkoxy, —OC(O)$R_2$, or —$NR_3R_4$; $R_2$ is $C_1$-$C_3$ alkyl or aryl; $R_3$ is H, $C_1$-$C_3$ alkyl, alkylcyclopropane, cyclohexyl, benzyl, or —$SO_2$—$R_5$; $R_4$ is H, $C_1$-$C_3$ alkyl, or —$SO_2$—$R_5$; and $R_5$ is alkyl, cycloalkyl, aryl or heteroaryl.

In yet another preferred aspect of this embodiment, the chemical structure is

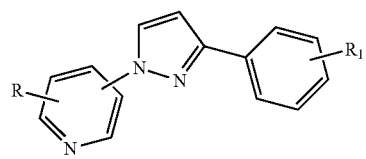

wherein R is ethyl, n-propyl, isopropyl, —O—$C_{1-3}$ alkoxy, a substituted or unsubstituted pyrrolidine, or a substituted or unsubstituted morpholine; $R_1$ is H, halogen, —OH, —O—$C_{1-3}$ alkoxy, —OC(O)$R_2$, or —$NR_3R_4$; $R_2$ is $C_1$-$C_3$ alkyl or aryl; $R_3$ is H, $C_1$-$C_3$ alkyl, alkylcyclopropane, cyclohexyl, benzyl, or —$SO_2$—$R_5$; $R_4$ is H, $C_1$-$C_3$ alkyl, or —$SO_2$—$R_5$; and $R_5$ is alkyl, cycloalkyl, aryl or heteroaryl.

In yet another preferred aspect of this embodiment, the chemical structure is

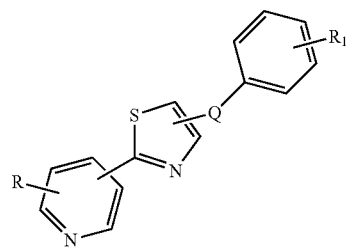

wherein Q is —NH—C(O) or —C(O)—NH; R is ethyl, n-propyl, isopropyl, —O—$C_{1-3}$ alkoxy, a substituted or unsubstituted pyrrolidine, or a substituted or unsubstituted morpholine; $R_1$ is H, halogen, —OH, —O—$C_{1-3}$ alkoxy, —OC(O)$R_2$, or —$NR_3R_4$; $R_2$ is $C_1$-$C_3$ alkyl or aryl; $R_3$ is H, $C_1$-$C_3$ alkyl, alkylcyclopropane, cyclohexyl, benzyl, or —$SO_2$—$R_5$; $R_4$ is H, $C_1$-$C_3$ alkyl, or —$SO_2$—$R_5$; and $R_5$ is alkyl, cycloalkyl, aryl or heteroaryl.

In yet another preferred aspect of this embodiment, the chemical structure is

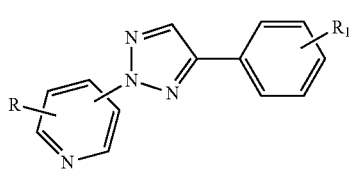

wherein R is ethyl, n-propyl, isopropyl, —O—$C_{1-3}$ alkoxy, a substituted or unsubstituted pyrrolidine, or a substituted or unsubstituted morpholine; $R_1$ is H, halogen, —OH, —O—$C_{1-3}$ alkoxy, —OC(O)$R_2$, or —$NR_3R_4$; $R_2$ is $C_1$-$C_3$ alkyl or aryl; $R_3$ is H, $C_1$-$C_3$ alkyl, alkylcyclopropane, cyclohexyl, benzyl, or —$SO_2$—$R_5$; $R_4$ is H, $C_1$-$C_3$ alkyl, or —$SO_2$—$R_5$; and $R_5$ is alkyl, cycloalkyl, aryl or heteroaryl.

In yet another preferred aspect of this embodiment, the chemical structure is

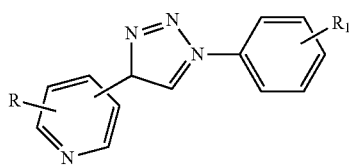

wherein R is ethyl, n-propyl, isopropyl, —O—$C_{1-3}$ alkoxy, a substituted or unsubstituted pyrrolidine, or a substituted or unsubstituted morpholine; $R_1$ is H, halogen, —OH, —O—$C_{1-3}$ alkoxy, —OC(O)$R_2$, or —N$R_3R_4$; $R_2$ is $C_1$-$C_3$ alkyl or aryl; $R_3$ is H, $C_1$-$C_3$ alkyl, alkylcyclopropane, cyclohexyl, benzyl, or —SO$_2$—$R_5$; $R_4$ is H, $C_1$-$C_3$ alkyl, or —SO$_2$—$R_5$; and $R_5$ is alkyl, cycloalkyl, aryl or heteroaryl.

In yet another preferred aspect of this embodiment, the chemical structure is

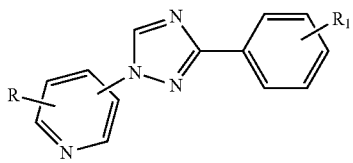

wherein R is ethyl, n-propyl, isopropyl, —O—$C_{1-3}$ alkoxy, a substituted or unsubstituted pyrrolidine, or a substituted or unsubstituted morpholine; $R_1$ is H, halogen, —OH, —O—$C_{1-3}$ alkoxy, —OC(O)$R_2$, or —N$R_3R_4$; $R_2$ is $C_1$-$C_3$ alkyl or aryl; $R_3$ is H, $C_1$-$C_3$ alkyl, alkylcyclopropane, cyclohexyl, benzyl, or —SO$_2$—$R_5$; $R_4$ is H, $C_1$-$C_3$ alkyl, or —SO$_2$—$R_5$; and $R_5$ is alkyl, cycloalkyl, aryl or heteroaryl.

In yet another preferred aspect of this embodiment, the chemical structure is

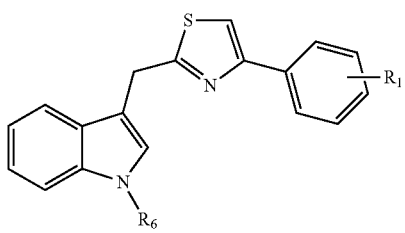

wherein $R_1$ is H, halogen, —OH, —O—$C_{1-3}$ alkoxy, —OC(O)$R_2$, or —N$R_3R_4$; $R_2$ is $C_1$-$C_3$ alkyl or aryl; $R_3$ is H, $C_1$-$C_3$ alkyl, alkylcyclopropane, cyclohexyl, benzyl, or —SO$_2$—$R_5$; $R_4$ is H, $C_1$-$C_3$ alkyl, or —SO$_2$—$R_5$; $R_5$ is alkyl, cycloalkyl, aryl or heteroaryl; and $R_6$ is H, methyl, isopropyl, benzyl, cyclohexyl, cyclopropylmethyl, —COMe, tert-butyloxycarbonyl, carboxybenzyl, methanesulfonyl, p-toluenesulfonyl, quinolinesulfonyl, or thiophenesulfonyl.

In yet another preferred aspect of this embodiment, the chemical structure is

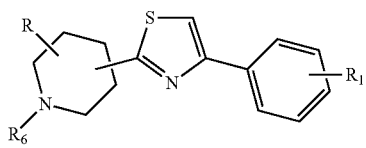

wherein R is ethyl, n-propyl, isopropyl, —O—$C_{1-3}$ alkoxy, a substituted or unsubstituted pyrrolidine, or a substituted or unsubstituted morpholine; $R_1$ is H, halogen, —OH, —O—$C_{1-3}$ alkoxy, —OC(O)$R_2$, or —N$R_3R_4$; $R_2$ is $C_1$-$C_3$ alkyl or aryl; $R_3$ is H, $C_1$-$C_3$ alkyl, alkylcyclopropane, cyclohexyl, benzyl, or —SO$_2$—$R_5$, $R_4$ is H, $C_1$-$C_3$ alkyl, or —SO$_2$—$R_5$; $R_5$ is alkyl, cycloalkyl, aryl or heteroaryl; and $R_6$ is H, methyl, isopropyl, benzyl, cyclohexyl, cyclopropylmethyl, —COMe, tert-butyloxycarbonyl, carboxybenzyl, methanesulfonyl, p-toluenesulfonyl, quinolinesulfonyl, or thiophenesulfonyl.

In yet another preferred aspect of this embodiment, the chemical structure is

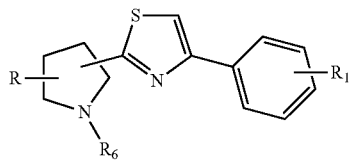

wherein R is ethyl, n-propyl, isopropyl, —O—$C_{1-3}$ alkoxy, a substituted or unsubstituted pyrrolidine, or a substituted or unsubstituted morpholine; $R_1$ is H, halogen, —OH, —O—$C_{1-3}$ alkoxy, —OC(O)$R_2$, or —N$R_3R_4$; $R_2$ is $C_1$-$C_3$ alkyl or aryl; $R_3$ is H, $C_1$-$C_3$ alkyl, alkylcyclopropane, cyclohexyl, benzyl, or —SO$_2$—$R_5$; $R_4$ is H, $C_1$-$C_3$ alkyl, or —SO$_2$—$R_5$; $R_5$ is alkyl, cycloalkyl, aryl or heteroaryl; and $R_6$ is H, methyl, isopropyl, benzyl, cyclohexyl, cyclopropylmethyl, —COMe, tert-butyloxycarbonyl, carboxybenzyl, methanesulfonyl, p-toluenesulfonyl, quinolinesulfonyl, or thiophenesulfonyl.

In yet another preferred aspect of this embodiment, the chemical structure is

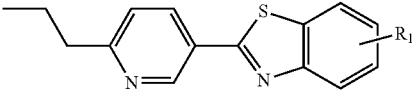

wherein $R_1$ is H, halogen, —OH, —O—$C_{1-3}$ alkoxy, —OC(O)$R_2$, or —N$R_3R_4$; $R_2$ is $C_1$-$C_3$ alkyl or aryl; $R_3$ is H, $C_1$-$C_3$ alkyl, alkylcyclopropane, cyclohexyl, or benzyl; $R_4$ is H, $C_1$-$C_3$ alkyl, or —SO$_2$—$R_5$; and $R_5$ is alkyl, aryl or heteroaryl.

In yet another preferred aspect of this embodiment, the chemical structure is

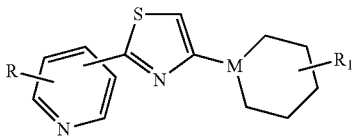

wherein M is N or CH; R is ethyl, n-propyl, isopropyl, —O—$C_{1-3}$ alkoxy, a substituted or unsubstituted pyrrolidine, or a substituted or unsubstituted morpholine; $R_1$ is H, halogen, —OH, —O—$C_{1-3}$ alkoxy, —OC(O)$R_2$, or —N$R_3R_4$; $R_2$ is $C_1$-$C_3$ alkyl or aryl; $R_3$ is H, $C_1$-$C_3$ alkyl, alkylcyclopropane, cyclohexyl, benzyl, or —SO$_2$—$R_5$, $R_4$ is H, $C_1$-$C_3$ alkyl, or —SO$_2$—$R_5$; and $R_5$ is alkyl, cycloalkyl, aryl or heteroaryl.

In another embodiment of the present invention, there is a method for treating a metabolic disorder in an animal in need thereof, comprising the step of: administering to the animal a therapeutically effective amount of at least one compound having the chemical structure:

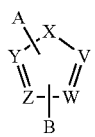

wherein A is a substituted or unsubstituted pyridine, a substituted or unsubstituted piperidine, a substituted or unsubstituted pyrrolidine, a substituted or unsubstituted indole, or a natural or an unnatural amino acid; B is a substituted or unsubstituted phenyl ring, a substituted or unsubstituted pyridine, a substituted or unsubstituted piperidine, a substituted or unsubstituted cycloalkyl ring, a substituted or unsubstituted heterocycloalkyl ring or wherein B in combination with V and W form a benzothiazole ring; W is N or C; X is O, S, N or C; Y is N or C; and Z is N or C; and wherein at least two of W, X, Y, and Z are other than carbon, or a pharmaceutically acceptable salt or a stereoisomer thereof or a combination thereof.

In yet another embodiment of the present invention, there is a method for method for treating a cell proliferative disease in an animal in need thereof, comprising the step of: administering to the animal a therapeutically effective amount of at least one compound having the chemical structure:

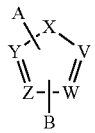

wherein A is a substituted or unsubstituted pyridine, a substituted or unsubstituted piperidine, a substituted or unsubstituted pyrrolidine, a substituted or unsubstituted indole, or a natural or an unnatural amino acid; B is a substituted or unsubstituted phenyl ring, a substituted or unsubstituted pyridine, a substituted or unsubstituted piperidine, a substituted or unsubstituted cycloalkyl ring, a substituted or unsubstituted heterocycloalkyl ring or wherein B in combination with V and W form a benzothiazole ring; W is N or C; X is O, S, N or C; Y is N or C; and Z is N or C; and wherein at least two of W, X, Y, and Z are other than carbon, or a pharmaceutically acceptable salt or a stereoisomer thereof or a combination thereof.

In yet another embodiment of the present invention, there is a method for reducing body weight in an animal in need thereof, comprising the step of: administering to the animal a therapeutically effective amount of at least one compound having the chemical structure:

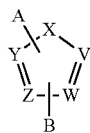

wherein A is a substituted or unsubstituted pyridine, a substituted or unsubstituted piperidine, a substituted or unsubstituted pyrrolidine, a substituted or unsubstituted indole, or a, natural or an unnatural amino acid; B is a substituted or unsubstituted phenyl ring, a substituted or unsubstituted pyridine, a substituted or unsubstituted piperidine, a substituted or unsubstituted cycloalkyl ring, a substituted or unsubstituted heterocycloalkyl ring or wherein B in combination with V and W form a benzothiazole ring; W is N or C; X is O, S, N or C; Y is N or C; and Z is N or C; and wherein at least two of W, X, Y, and Z are other than carbon, or a pharmaceutically acceptable salt or a stereoisomer thereof or a combination thereof.

In yet another embodiment of the present invention, there is a method for increasing thermogenesis without reducing lean body mass during weight loss in an animal, comprising the step of: administering to the animal a therapeutically effective amount of at least one compound having the chemical structure:

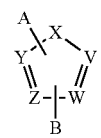

wherein A is a substituted or unsubstituted pyridine, a substituted or unsubstituted piperidine, a substituted or unsubstituted pyrrolidine, a substituted or unsubstituted indole, or a natural or an unnatural amino acid; B is a substituted or unsubstituted phenyl ring, a substituted or unsubstituted pyridine, a substituted or unsubstituted piperidine, a substituted or unsubstituted cycloalkyl ring, a substituted or unsubstituted heterocycloalkyl ring or wherein B in combination with V and W form a benzothiazole ring; W is N or C; X is O, S, N or C; Y is N or C; and Z is N or C; and wherein at least two of W, X, Y, and Z are other than carbon, or a pharmaceutically acceptable salt or a stereoisomer thereof or a combination thereof.

Provided herein are fatostatin analogs and derivatives and methods and strategies for producing the same. Also provided are methods of treating pathophysiological conditions, such as, but not limited to, metabolic disorders and related diseases, cell proliferative diseases, such as cancer, and for increasing thermogenesis without reducing lean body mass during weight loss in an animal with one or more of the described compounds. It is further contemplated that additional therapies may be provided that are administered concurrently or sequentially with the compounds. Thus, pharmaceutical compositions of the compounds in a pharmaceutically acceptable carrier are provided. Generally, the animal may be a mammal, preferably a human.

As described below, the invention provides a number of advantages and uses, however such advantages and uses are not limited by such description. Embodiments of the present invention are better illustrated with reference to the Figure(s), however, such reference is not meant to limit the present invention in any fashion. The embodiments and variations described in detail herein are to be interpreted by the appended claims and equivalents thereof.

Synthesis of fatostatin analogs or derivatives is accomplished by a series of strategic procedures which has been developed as described in FIGS. 1-30. The strategies include, inter alia, the reaction of amides or thioamides and amidines with acyl halides to form the 5-membered heterocyclic derivatives. As shown in FIG. 1, compounds 1-3 are reacted with bromoketone 4 to yield heterocyclic derivatives 5-7 respectively. The nitro group is subjected to reduction conditions to yield compounds 8-10. Protection of the amines 8-10 with suitable protecting groups, for example methanesulfonyl chloride in the presence of a base (such as Et$_3$N) yields compounds 11-13 respectively. Alternatively, compounds 8-10 are subjected to reductive amination conditions and the resultant secondary amines are protected to yield compounds 14-16 respectively.

Figure 2:
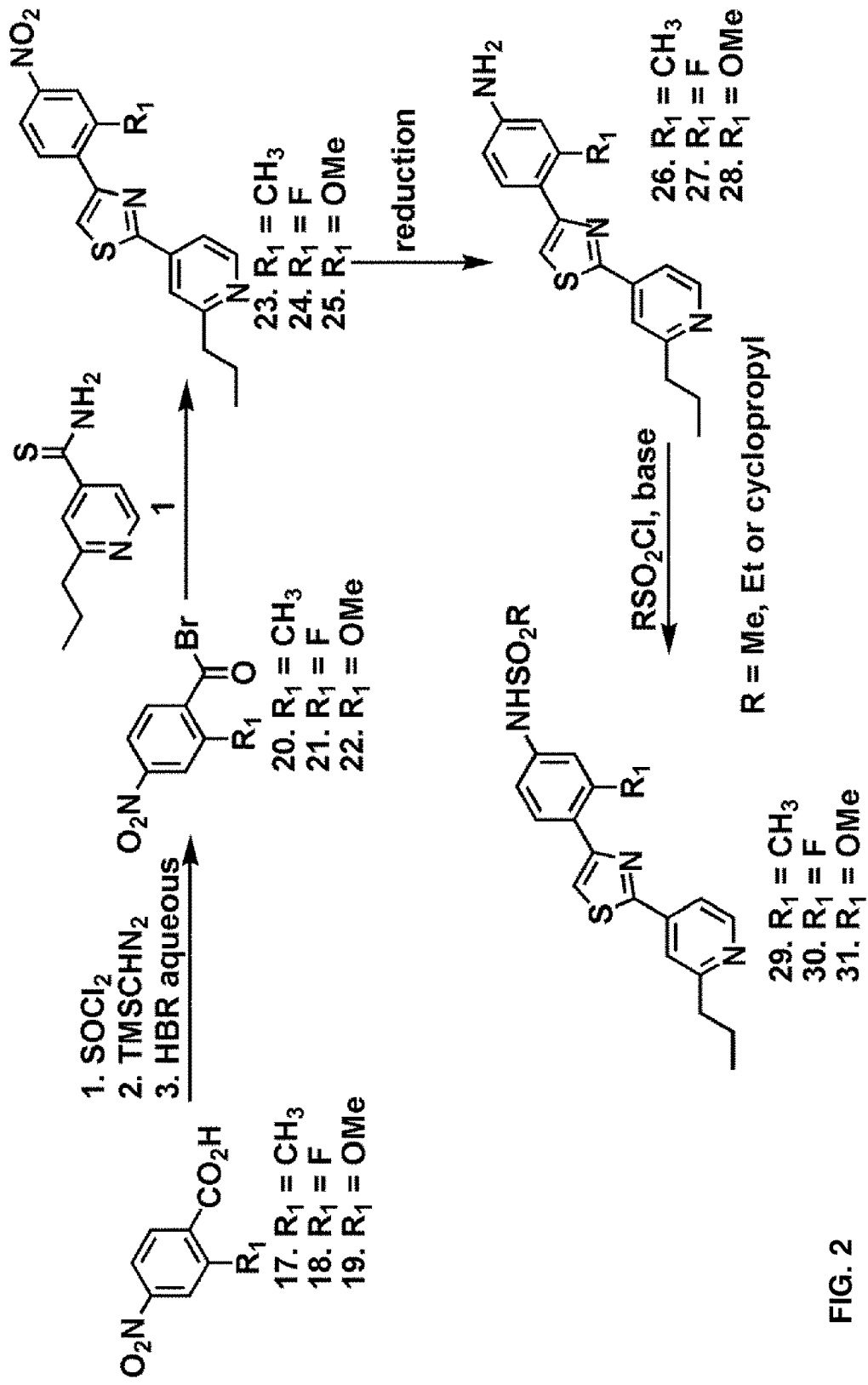
FIG. 2 illustrates the synthesis of thiazole derivatives 29-31 from 4-nitrobenzoic acid (or p-nitrobenzoic acid) derivatives 17-19.

FIG. 2 illustrates the synthesis of compounds 26-28. The synthesis begins with the conversion of 4-nitrobenzoic acid derivatives 17-19 to the corresponding acyl bromides 20-22. Acyl bromides 20-22 are then reacted with prothionamide (1) to yield the thiazole derivatives 23-25 respectively. The nitro groups of compounds 23-25 are reduced (e.g. hydrogenation) to result amines 26-28 respectively. Protection of the amine is accomplished by the reaction of the amines 26-28 with commercially available alkylsulfonyl chlorides in the presence of a base (such as Et$_3$N) yields corresponding sulfonamides 29-31.

Figure 3:
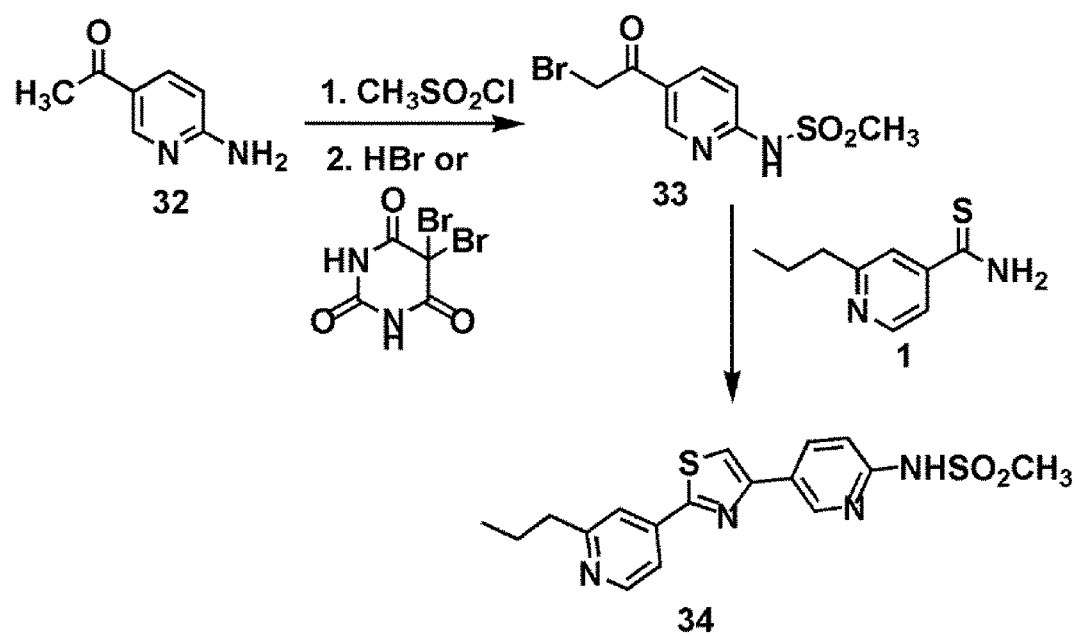
FIG. 3 illustrates the synthesis of thiazole derivative 34 from 1-(6-aminopyridin-3-yl)ethanonone (32).

Synthesis of thiazole derivative 34 from 1-(6-aminopyridin-3-yl)ethanonone (32) is shown in FIG. 3. The amine group is protected with methanesulfonyl chloride to yield the corresponding sulfonamide which under the conditions of alpha-bromination yielded the acyl bromide 33. Reaction of compound 33 with prothionamide (1) yields thiazole derivative 34.

Figure 4:
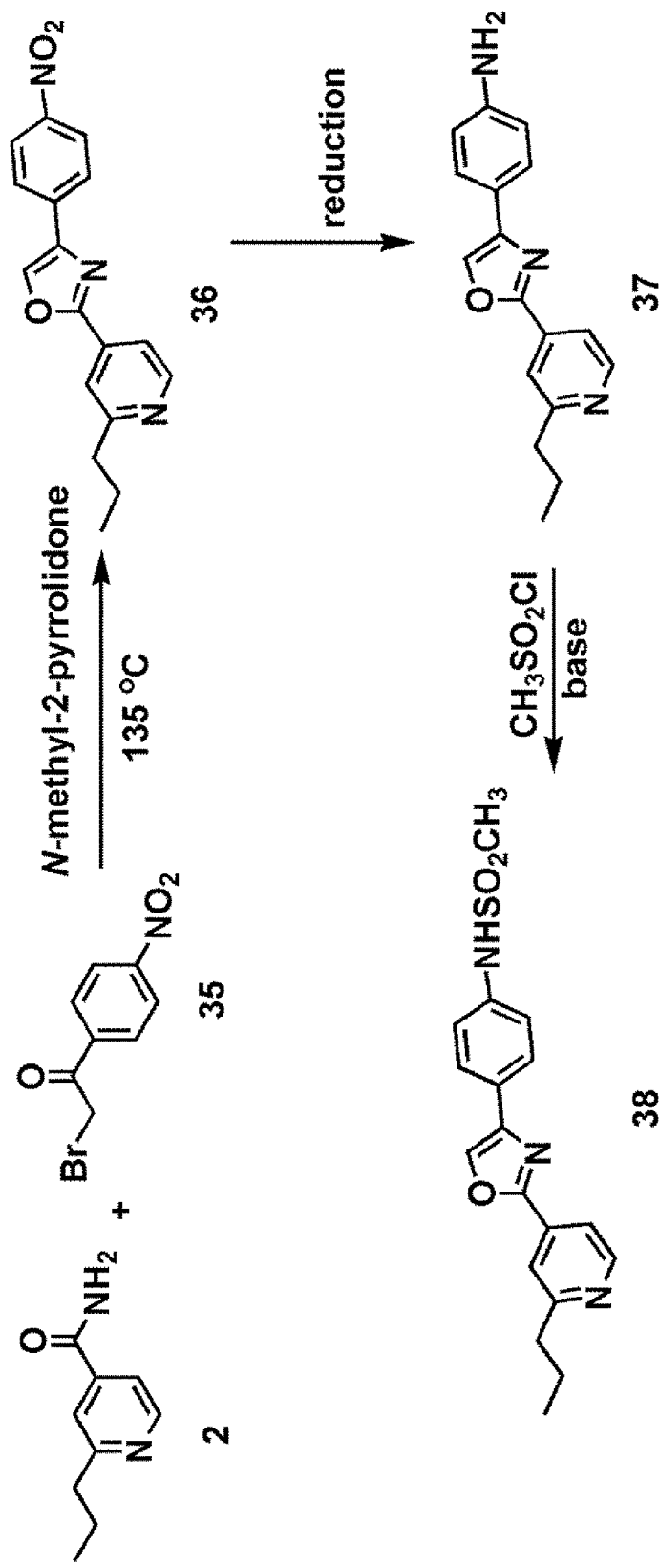
FIG. 4 illustrates the synthesis of oxazole derivative 38 from 2-propylpyridine-4-carboxamide (2).

Synthesis of oxazole derivative 38 is shown in FIG. 4. Reaction of amide 2 with acyl bromide 35 in the presence of N-methyl-2-pyrrolidone (NMP) at 135° C. yields the oxazole compound 36. The nitro group of compound 36 is reduced (e.g. hydrogenation) to produce an amine 37. Protection of the amine with methanesulfonyl chloride in the presence of a base (such as Et$_3$N) yields the corresponding sulfonamide 38.

Figure 5:
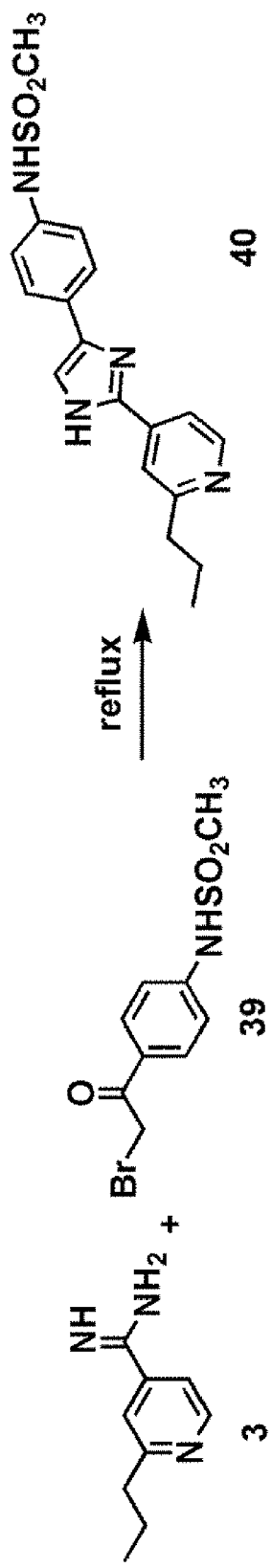
FIG. 5 illustrates the synthesis of imidazole derivative 40 from 2-propylpyridine-4-carboxamidine (3).

Synthesis of imidazole derivative 40 is shown in FIG. 5. The method involves the reaction of 2-propylpyridine-4-carboxamidine (3) with acyl bromide 39 under reflux conditions to yield the desired compound 40.

Figure 6:
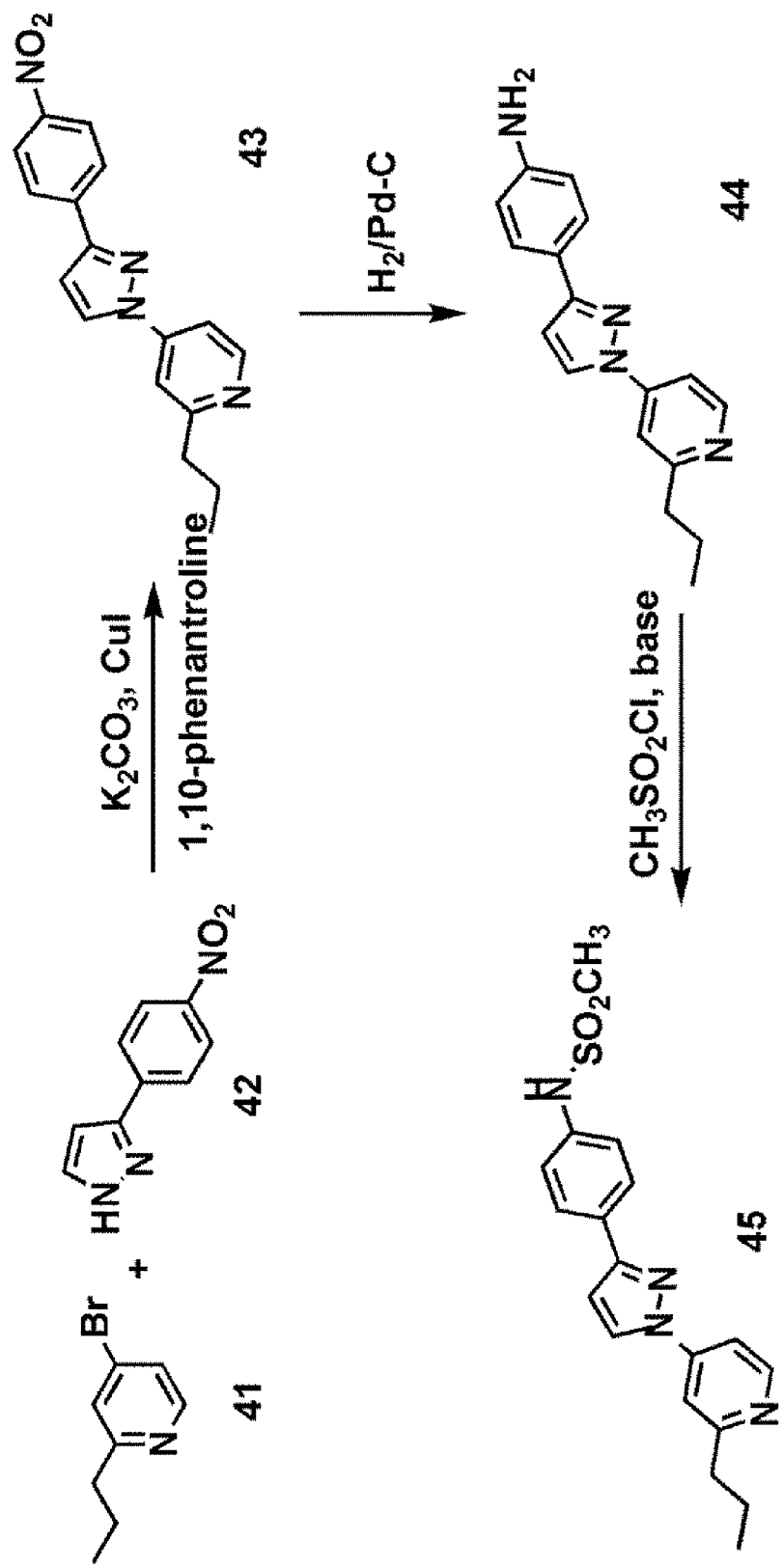
FIG. 6 illustrates the synthesis of thiazole derivative 45.

Synthesis of pyrazole derivative 44 is shown in FIG. 6. The reaction involves generation of pyrazole derivative 43 by the reaction of compound 41 with pyrazole 42. The nitro group of compound 43 is reduced (e.g. hydrogenation) to result an amine 44. Protection of the amine with methanesulfonyl chloride in the presence of a base (such as Et$_3$N) yields the corresponding sulfonamide 45.

Figure 7:
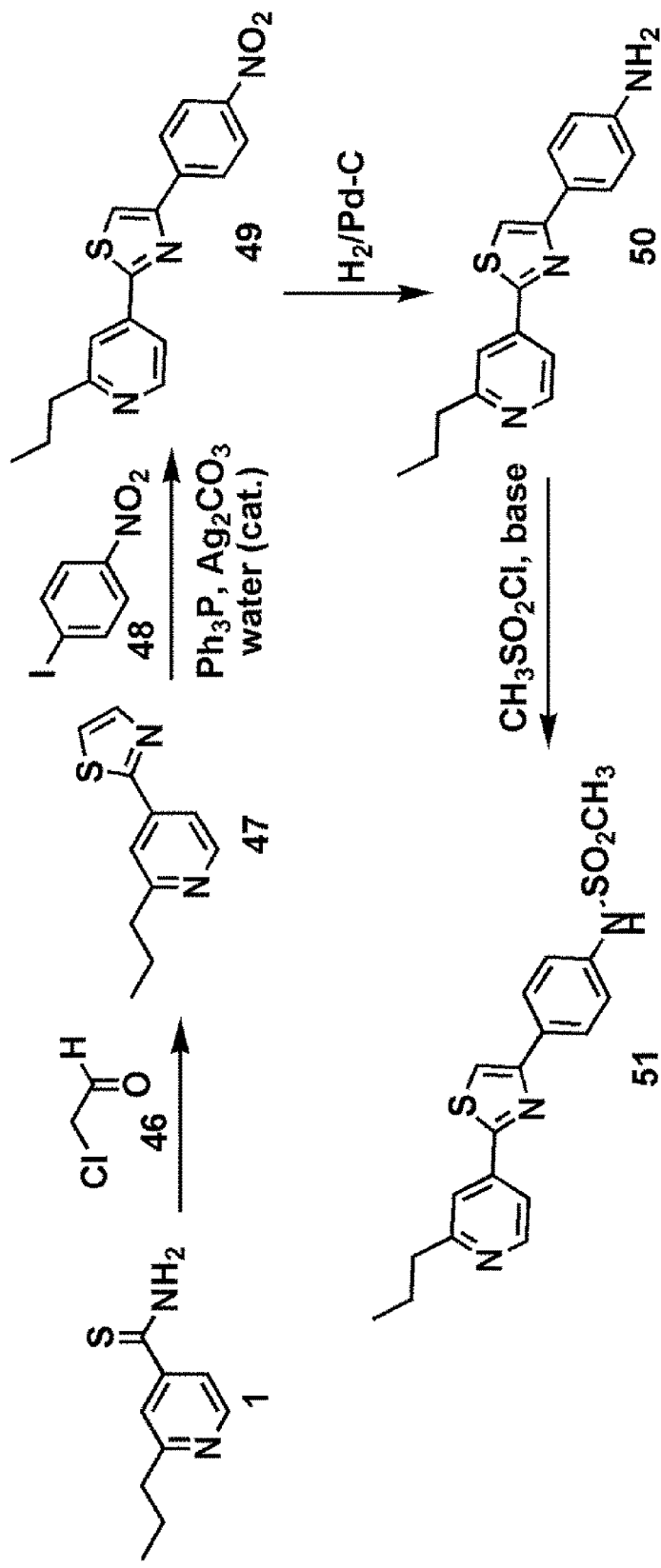
FIG. 7 illustrates the synthesis of thiazole derivative 51 from 2-propylpyridine-4-carbothioamide (prothionamide; 1).

Synthesis of thiazole derivative 51 is shown in FIG. 7. Prothionamide (1) when reacted with 2-chloroacetaldehyde (46) yields the thiazole compound 47. Compound 47 is then coupled with aryl iodide 48 in the presence of triphenyl phosphine (Ph$_3$P), silver carbonate (Ag$_2$CO$_3$) and catalytic amount of water, to result in the formation of compound 49. The nitro group of compound 49 is reduced (e.g. hydrogenation) to produce an amine 50. Protection of the amine with methanesulfonyl chloride in the presence of a base (such as Et$_3$N) yields the corresponding sulfonamide 51.

Figure 8:
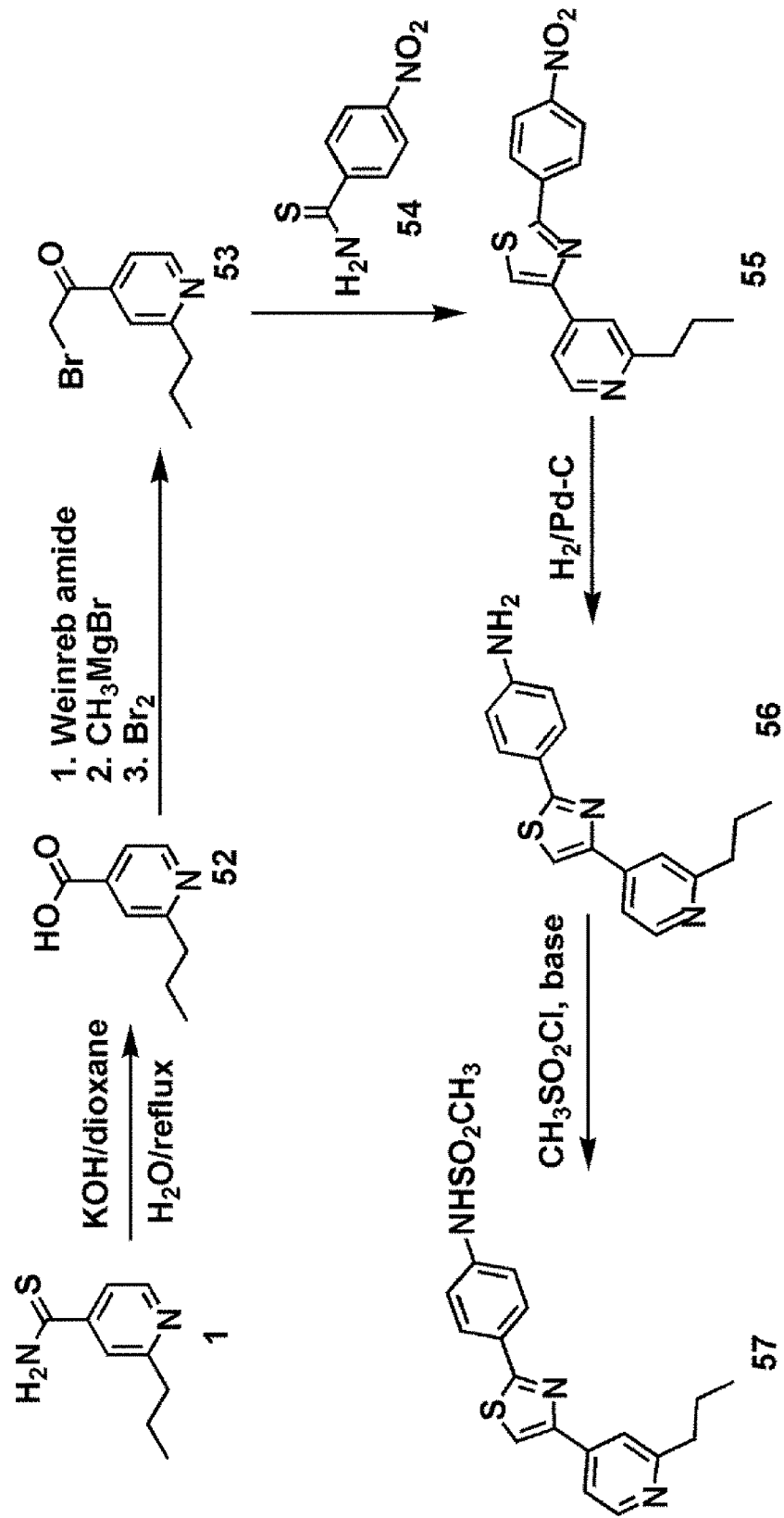
FIG. 8 illustrates the synthesis of thiazole derivative 57 from 2-propylpyridine-4-carbothioamide (prothionamide; 1).

Synthesis of thiazole derivative 57 is shown in FIG. 8. Prothionamide (1) is converted to acyl bromide 53 by reaction with a Weinreb amide followed by a Grignard reaction with methylmagnesium bromide to obtain a methyl ketone which upon reaction with bromine yields compound 53. Compound 53 is then reacted with 4-nitrobenzothionamide (54) to yield the thiazole derivative 55. The nitro group of compound 55 is reduced (e.g. hydrogenation) to produce an amine 56. Protection of the amine with methanesulfonyl chloride in the presence of a base (such as Et$_3$N) yields the corresponding sulfonamide 57.

Figure 9:
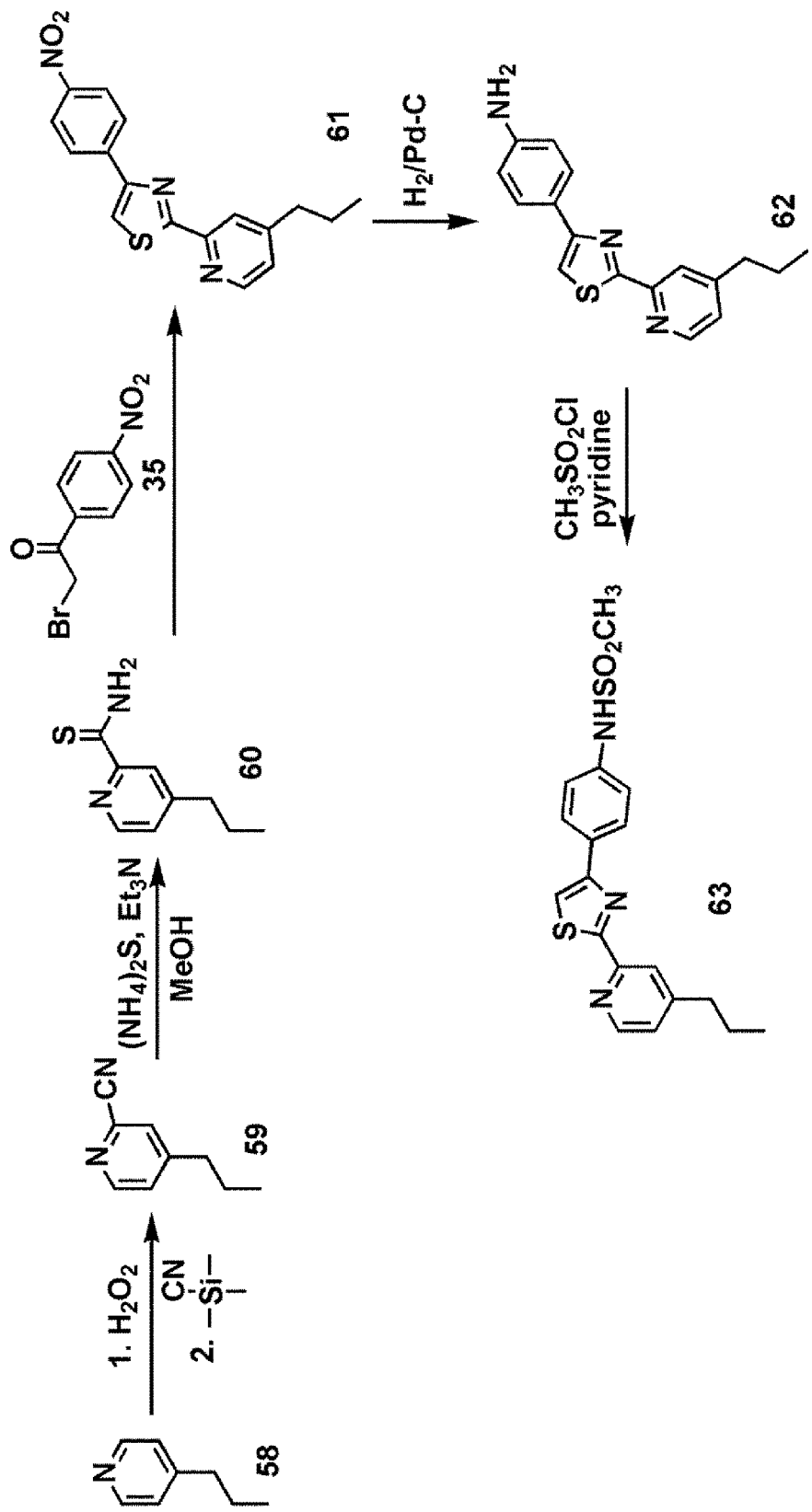
FIG. 9 illustrates the synthesis of thiazole derivative 63 from 4-propylpyridine (58).

Synthesis of thiazole derivative 63 is shown in FIG. 9. Starting with compound 58, the method involves incorporation of a cyano group to obtain compound 59, which is then converted to the thioamide 60. Reaction of the thioamide 60 with compound 35 results in the formation of thiazole derivative 61. The nitro group of compound 61 is reduced (e.g. hydrogenation) to result an amine 62. Protection of the amine with methanesulfonyl chloride in the presence of a base (such as Et$_3$N) yields the corresponding sulfonamide 63.

Figure 10:
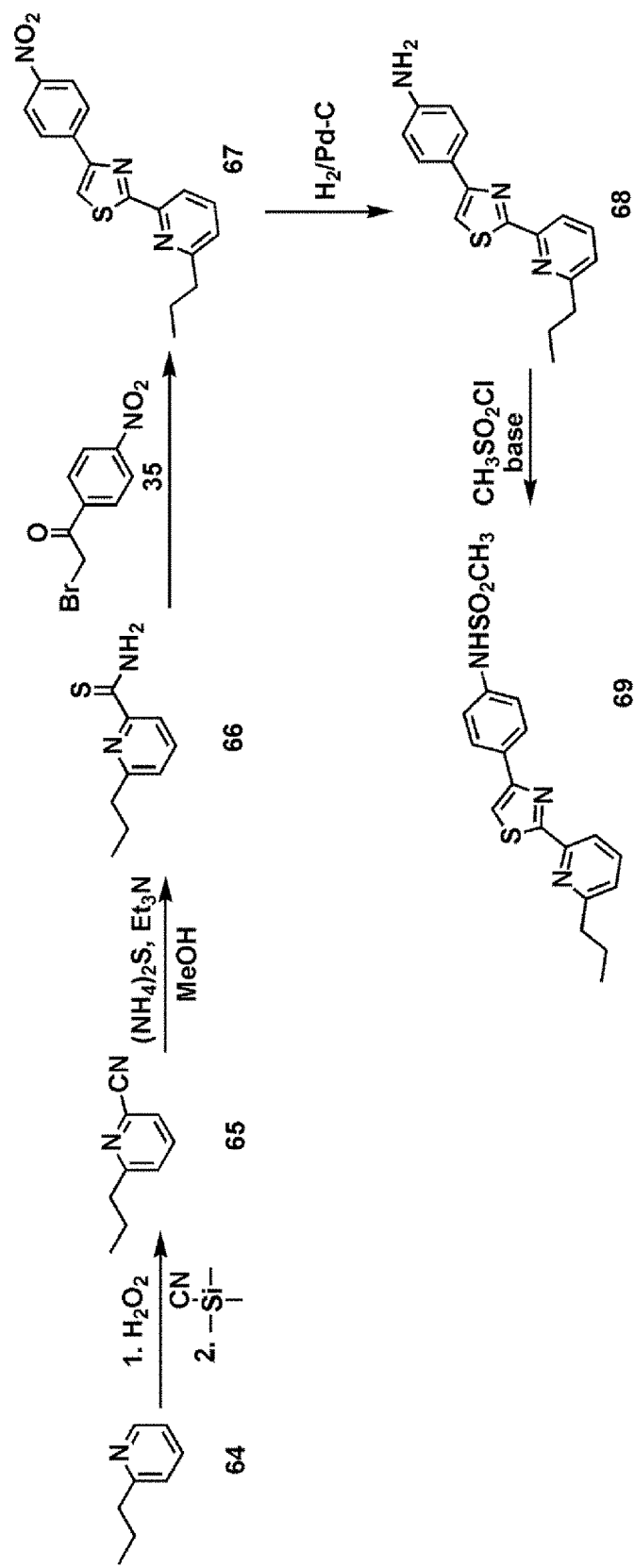
FIG. 10 illustrates the synthesis of thiazole derivative 69 from 2-propylpyridine (64).

Synthesis of thiazole derivative 69 is shown in FIG. 10. Starting with compound 64, the method involves incorporation of a cyano group to obtain compound 65, which is then converted to the thioamide 66. Reaction of the thioamide 66 with compound 35 results in the formation of thiazole derivative 67. The nitro group of compound 67 is reduced (e.g. hydrogenation) to produce an amine 68. Protection of the amine with methanesulfonyl chloride in the presence of a base (such as Et$_3$N) yields the corresponding sulfonamide 69.

Figure 11:
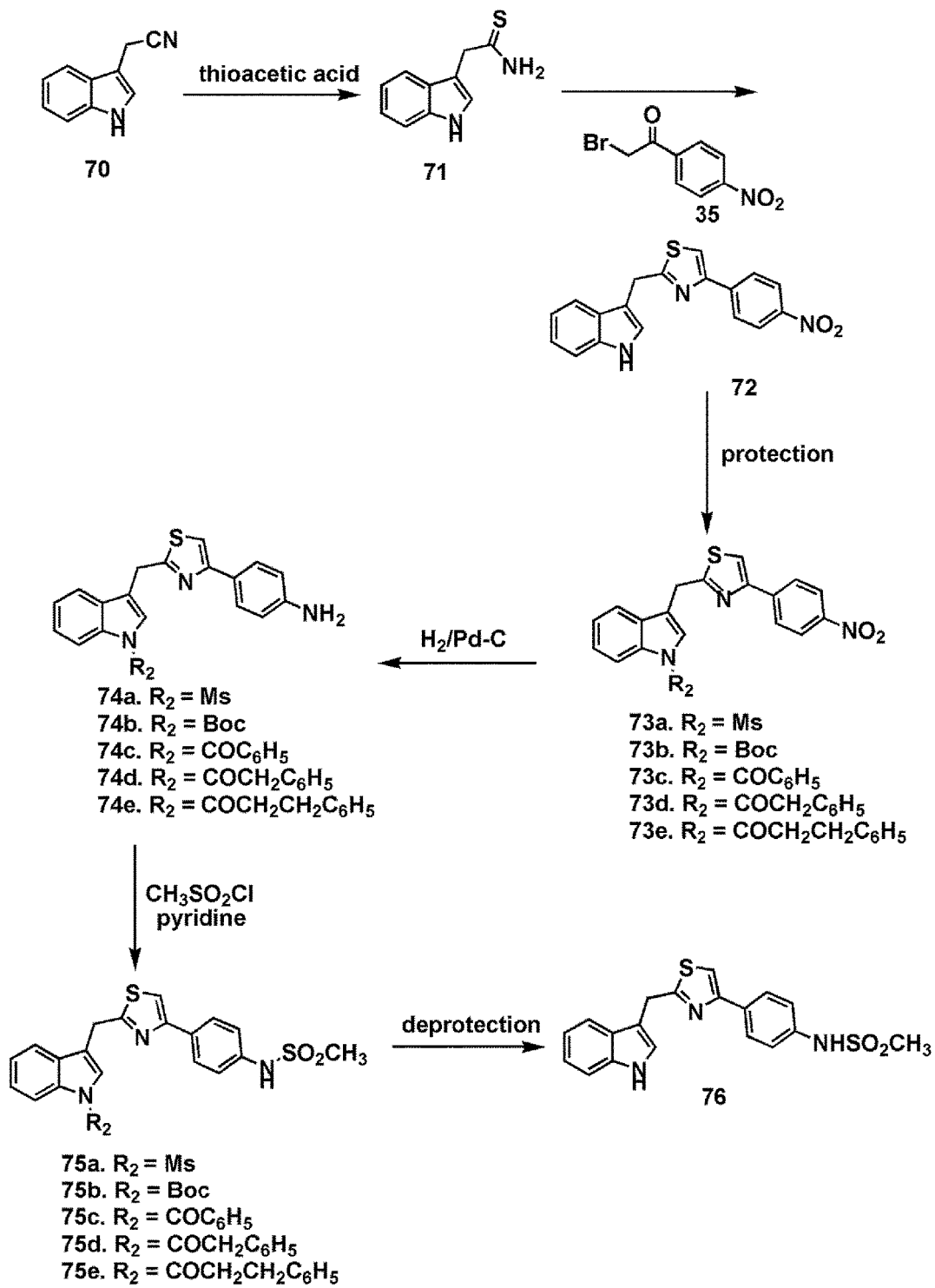
FIG. 11 illustrates the synthesis of thiazole derivative 76 from 2-(1H-indol-3-yl)acetonitrile (70).

Synthesis of thiazole derivative 76 is shown in FIG. 11. The indole 70 when reacted with thioacetic acid yields the corresponding thioamide 71. Thioamide 71 upon reaction with the bromoketone 35 and subsequent protection of the free —NH group of the indole with suitable protecting groups afforded compounds 73a-73e. The nitro group of compounds 73a-73e was reduced to corresponding amine to yield compounds 74a-74e, which was then protected as the sulfonamides 74a-75e. Removal of the protecting groups present in the indole nitrogen results in the formation of thiazole derivative 76.

Figure 12A:
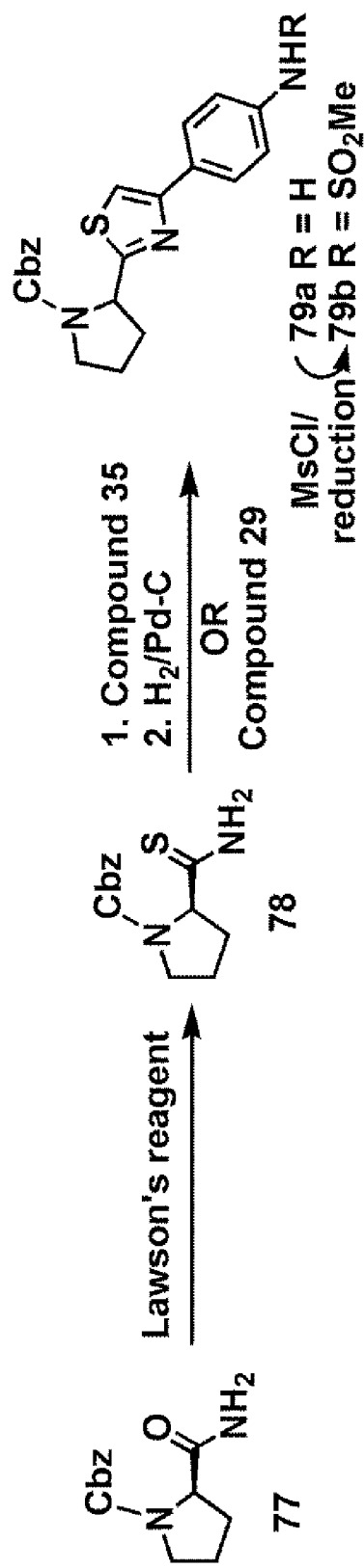
FIG. 12A illustrates the synthesis of thiazole derivatives 79a-79b from pyrrolidine-2-carboxamide (77).
Figure 12B:
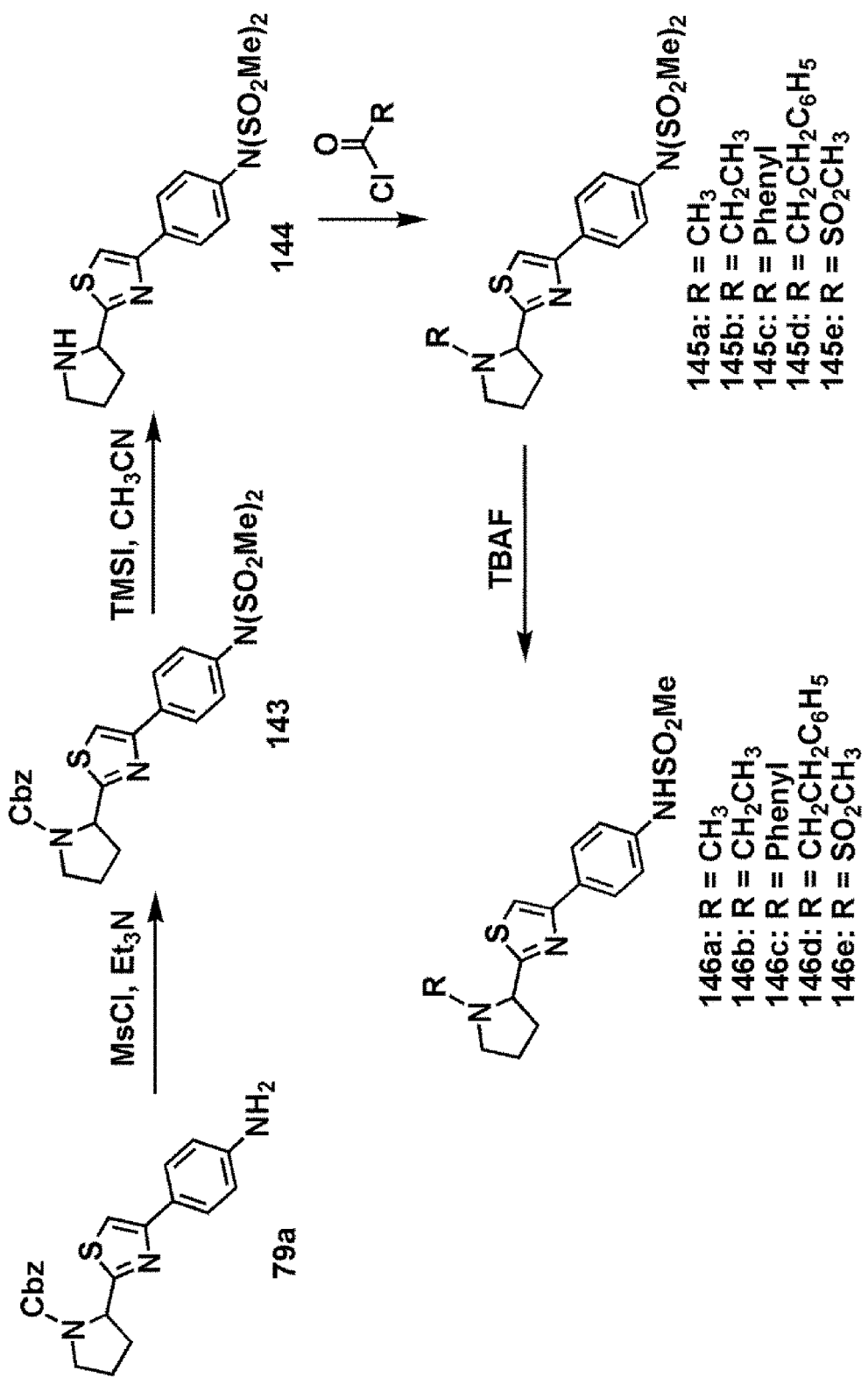
Figure 13:
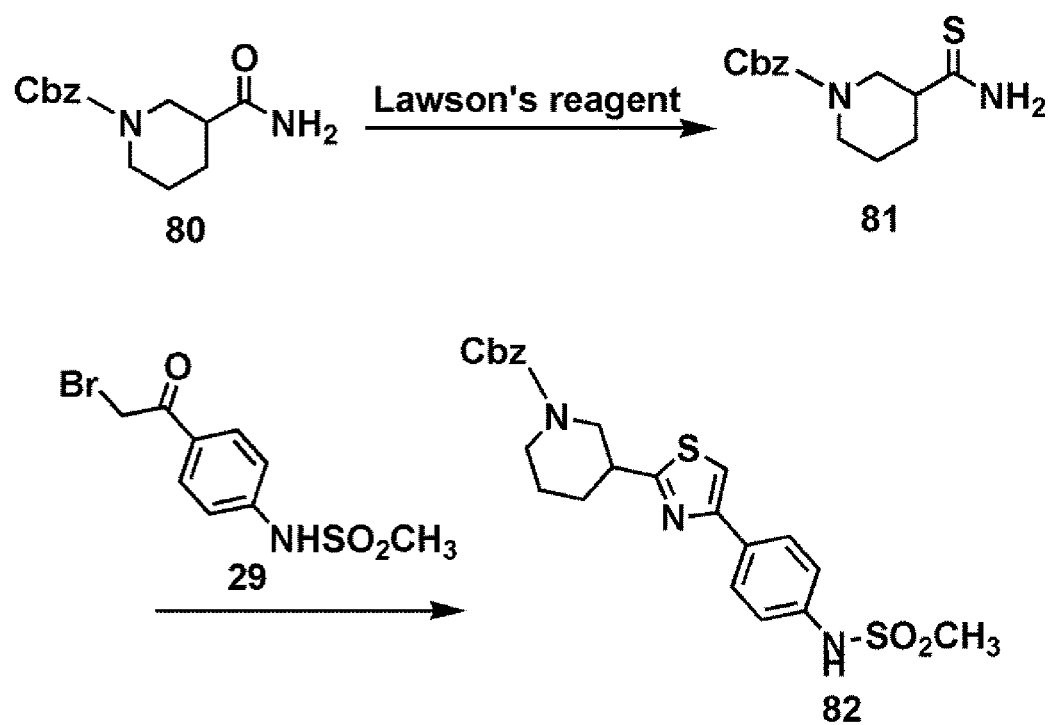
FIG. 13 illustrates the synthesis of thiazole derivative 82 from piperidine-3-carboxamide (80).
Figure 14:
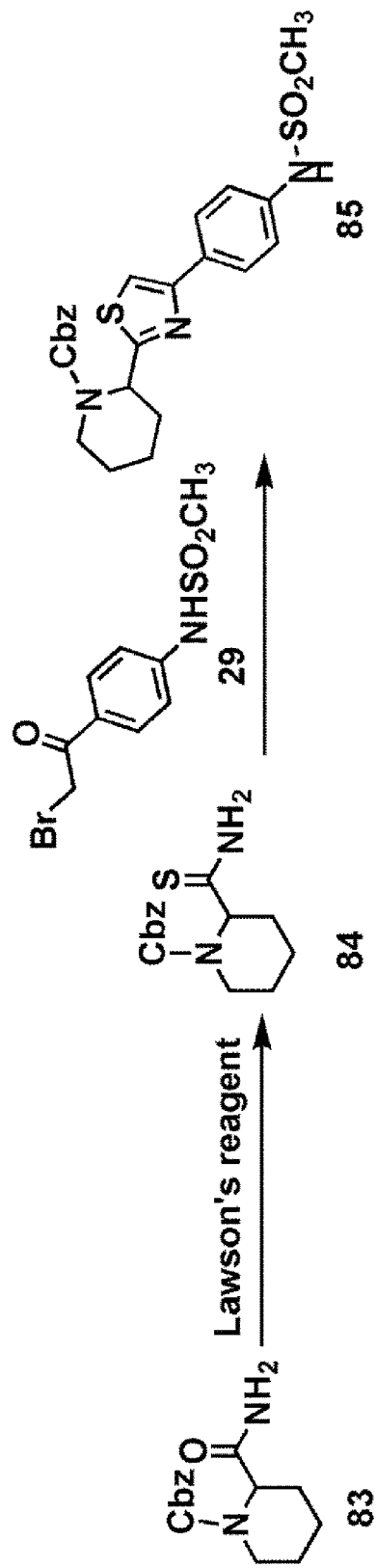
FIG. 14 illustrates the synthesis of thiazole derivative 85 from piperidine-2-carboxamide (83).

Synthesis of thiazole derivatives 79a-79b is shown in FIG. 12A. Pyrrolidine-2-carboxamide (77) upon reaction with Lawson's reagent yields the thioamide 78. Reaction of 78 with the acyl bromide 35 and subsequent reduction of the nitrogroup yielded the thiazole derivative 79a, which was protected as the sulfonamide derivative 79b. Other derivatives 146a-146e are prepared as shown in FIG. 12B.

Using similar strategy, piperidine-3-carboxamide (80) and piperidine 2-carboxamide (83) are converted to the thiazole derivatives 82 (FIG. 13) and 85 (FIG. 14) respectively.

Figure 15:
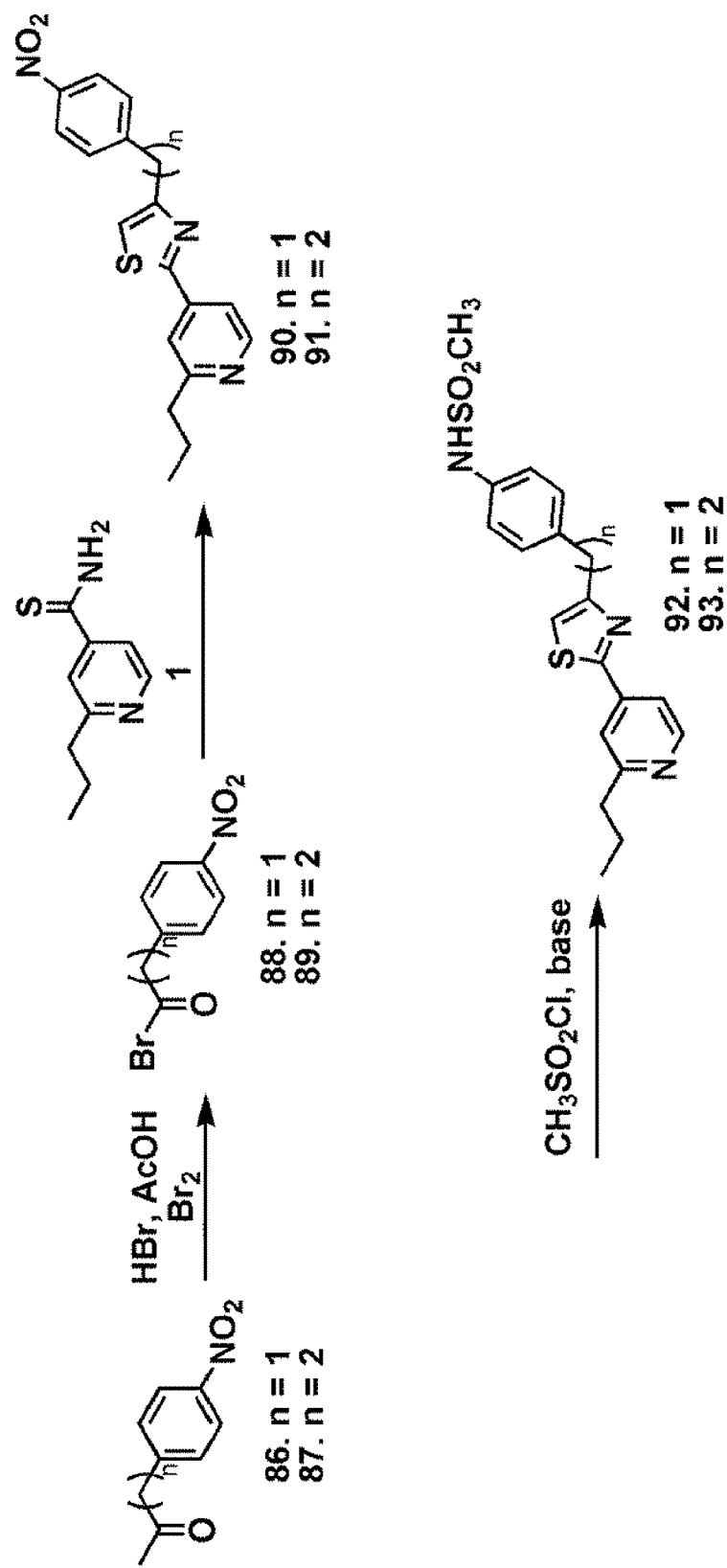
FIG. 15 illustrates the synthesis of thiazole derivatives 92-93.

Synthesis of thiazole derivatives 92 and 93 are shown in FIG. 15. The methyl ketone present in compounds 86 and 87 are converted to acyl bromides 88 and 89 by reaction with HBr in acetic acid in the presence of bromine. The acyl bromides 88 and 89 are then reacted with prothionamide (1) to yield the thiazoles 90 and 91 respectively. The nitro group of compounds 90 and 91 are reduced (e.g. hydrogenation) to produce corresponding amines, which are subsequently protected with methanesulfonyl chloride to yield the sulfonamides 92 and 93.

Figure 16:
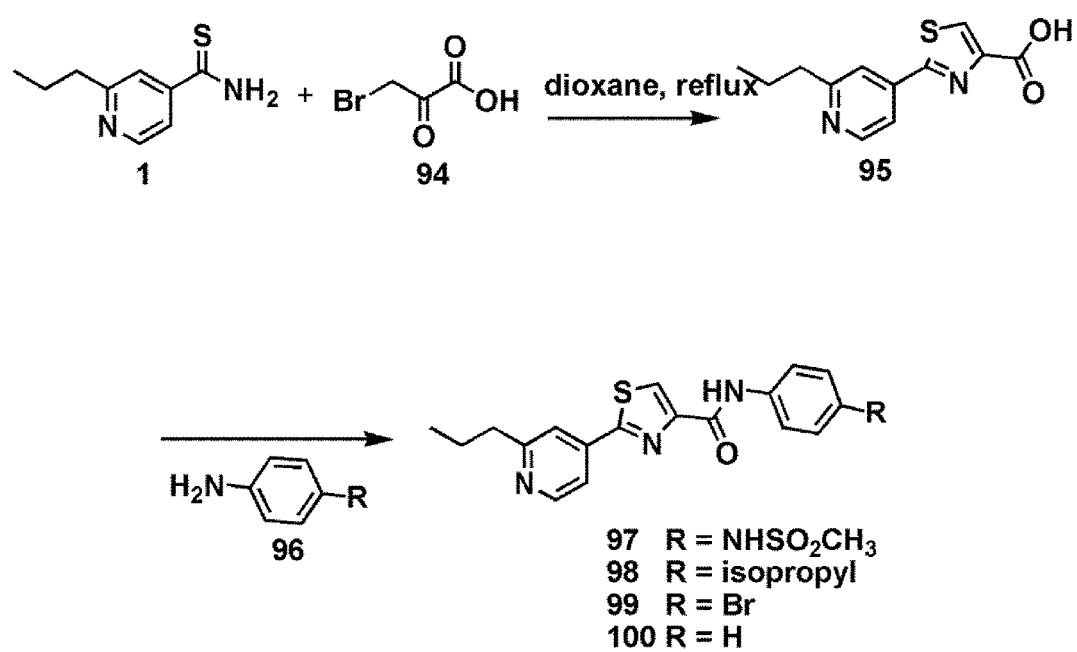
FIG. 16 illustrates the synthesis of thiazole derivatives 97-100 from 2-propylpyridine-4-carbothioamide (prothionamide; 1).
Figure 17:
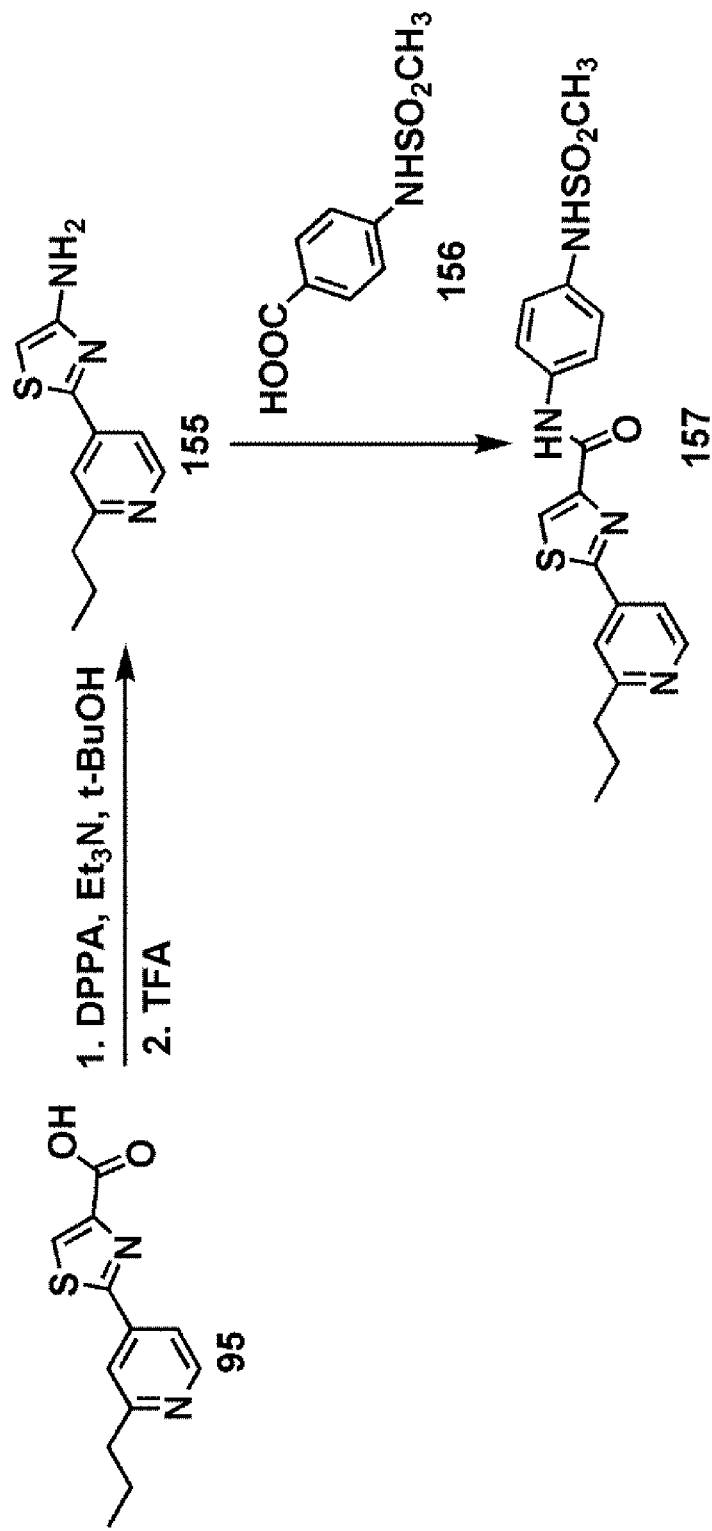
FIG. 17 illustrates the synthesis of thiazole derivatives 157 and 159 from carboxylic acid 95.

Synthesis of thiazole derivatives 97-100 are shown in FIG. 16. Prothionamide (1) upon reaction with compound 94 in dioxane under reflux conditions yielded the thiazole 95. Amide formation reaction of compound 95 with the amine 96 yielded the thiazole derivative 97. Alternatively, the acid group of compound 95 is converted to an amine (conditions: DPPA, TEA, t-BuOH then TFA) to produce compound 155. Coupling reaction of compound 155 with an acid 156 resulted in the formation of thiazole derivative 157 (FIG. 17).

Figure 18:
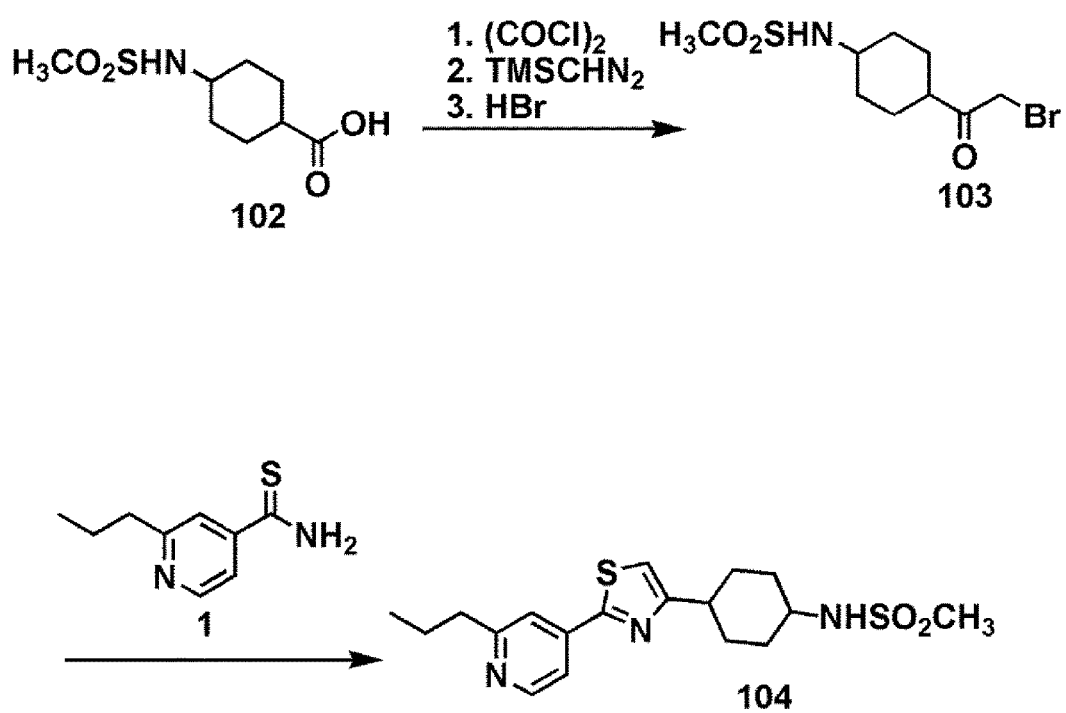
FIG. 18 illustrates the synthesis of thiazole derivative 104 from cyclohexane derivatives 102.
Figure 19:
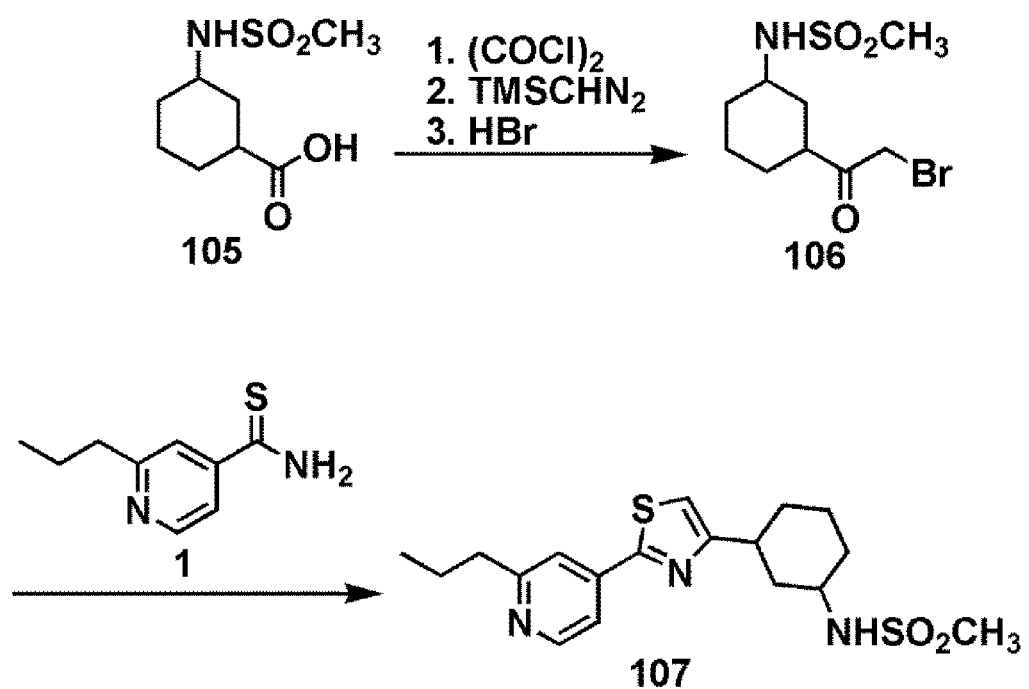
FIG. 19 illustrates the synthesis of thiazole derivative 107 from cyclohexane derivatives 105.
Figure 20:
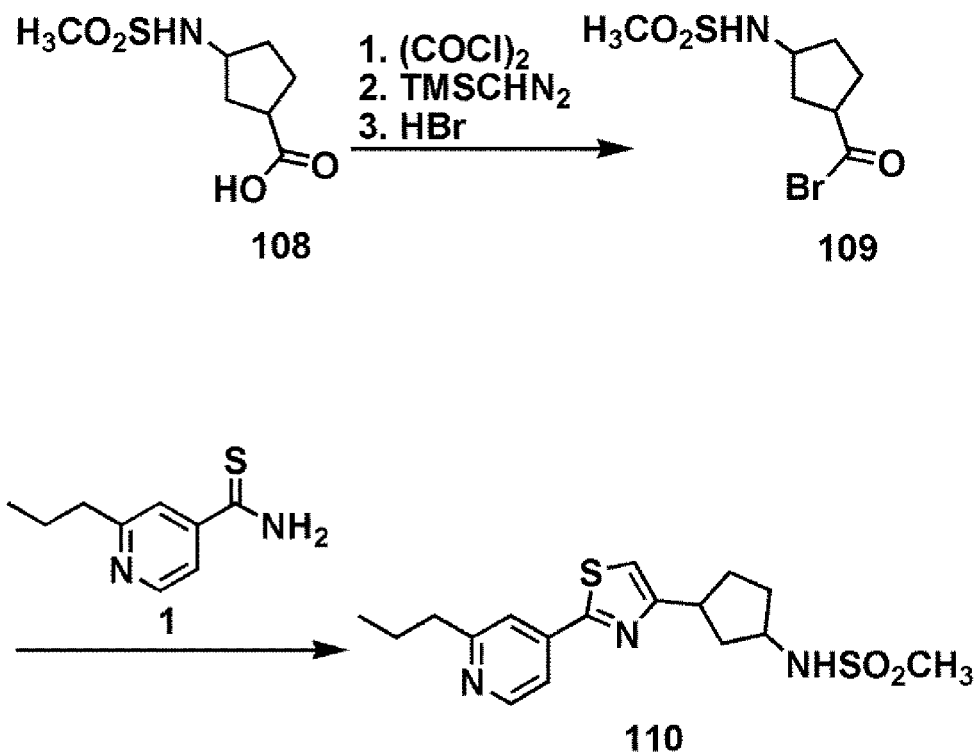
FIG. 20 illustrates the synthesis of thiazole derivative 104 and 107 from cyclohexane derivatives 102 and 105 respectively.

Synthesis of thiazole derivative 104 is shown in FIG. 18. Compound 102 is converted to the acyl bromide 103 in 3 steps. Specifically, the carboxylic acid of compound 102 is converted to the acid chloride by reaction with oxalyl chloride. The acid chloride is then reacted with TMSCHN$_2$ and subsequently reacted with HBr to yield the desired compound 103. Compound 103 when reacted with prothionamide (1) yields the thiazole derivative 104. In a similar strategy, bromoketone 106 is obtained in 3 steps from 105 (FIG. 19). Compound 105 when reacted with prothionamide (1) yields the thiazole derivative 107. Using similar approach, compound 108 is transformed to the thiazole derivative 110 (FIG. 20).

Figure 21:
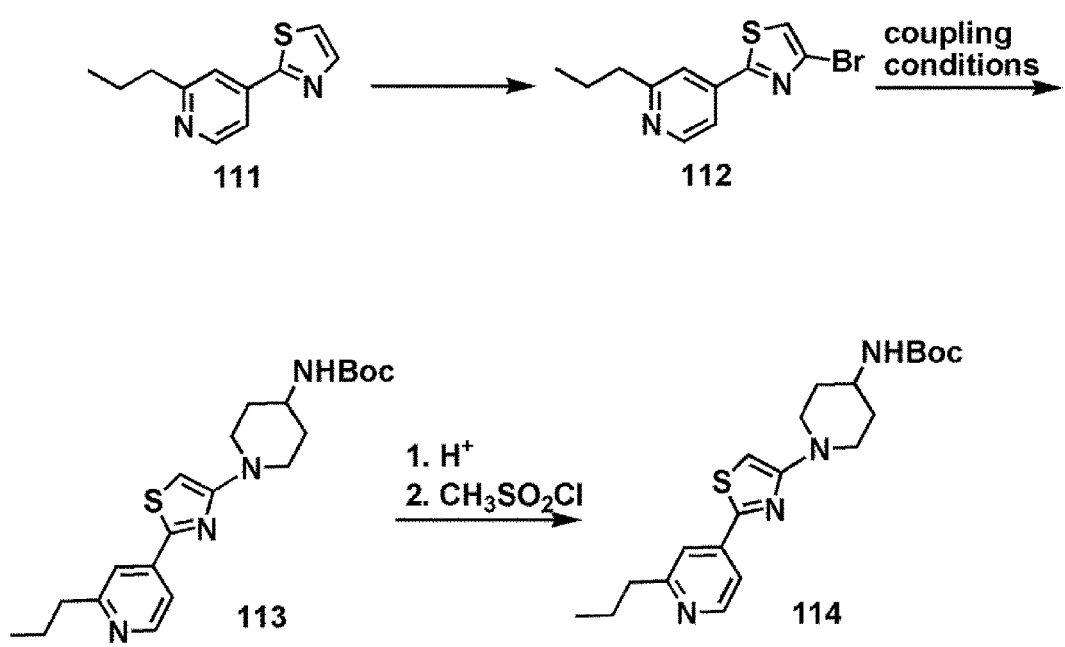
FIG. 21 illustrates the synthesis of thiazole derivative 114 from 2-propyl-4-(thiazol-2-yl)pyridine (111).

Thiazole derivative 114 is synthesized using a coupling strategy starting from 2-propyl-4-(thiazol-2-yl)pyridine (111) (FIG. 21). The bromo derivative 112 undergo a coupling reaction with an amine to yield compound 113. Removal of the Boc protection and subsequent protection with methanesulfonyl chloride yields the thiazole derivative 114.

Figure 22:
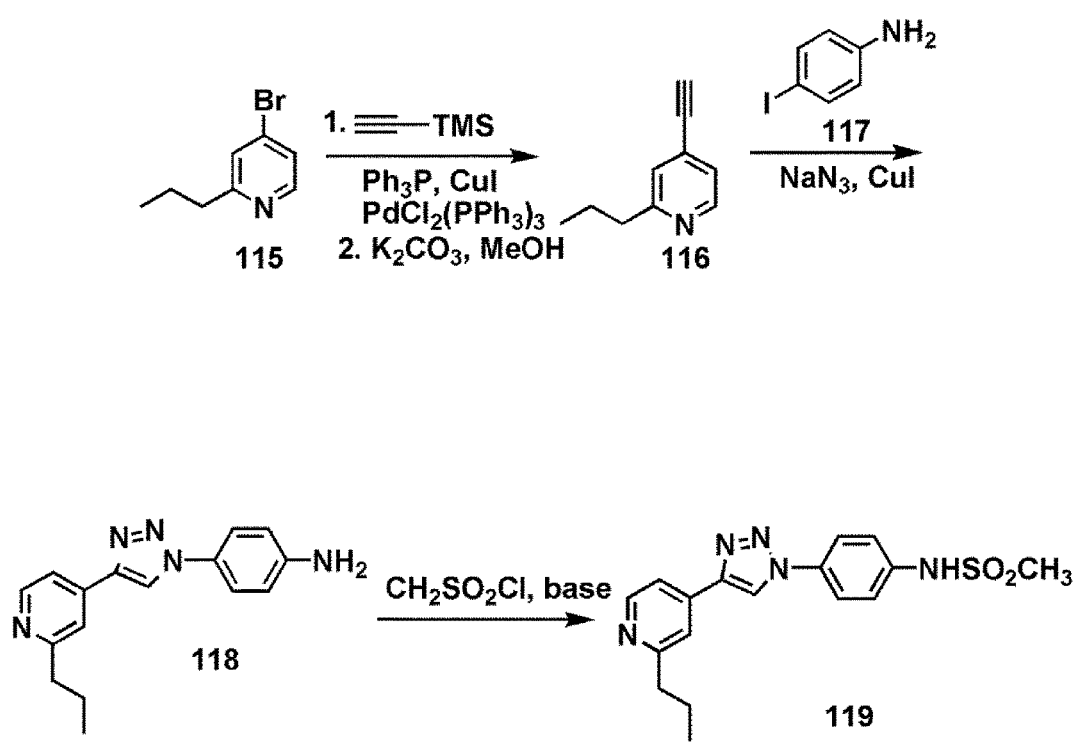
FIG. 22 illustrates the synthesis of triazole derivative 119 from 4-bromopropylpyridine (115).

Synthesis of triazole derivative 119 is shown in FIG. 22. Compound 116 is obtained from 115 by the reaction with TMS-acetylene using coupling conditions ($Ph_3P$, CuI, $PdCl_2$ $(PPh_3)_3$). Compound 116 then subjected to click chemistry with suitable azides in the present of CuI followed by reaction with 117 to obtain compound 118. Protection of the amine with methanesulfonyl chloride in the presence of a base yields compound 119.

Figure 23:
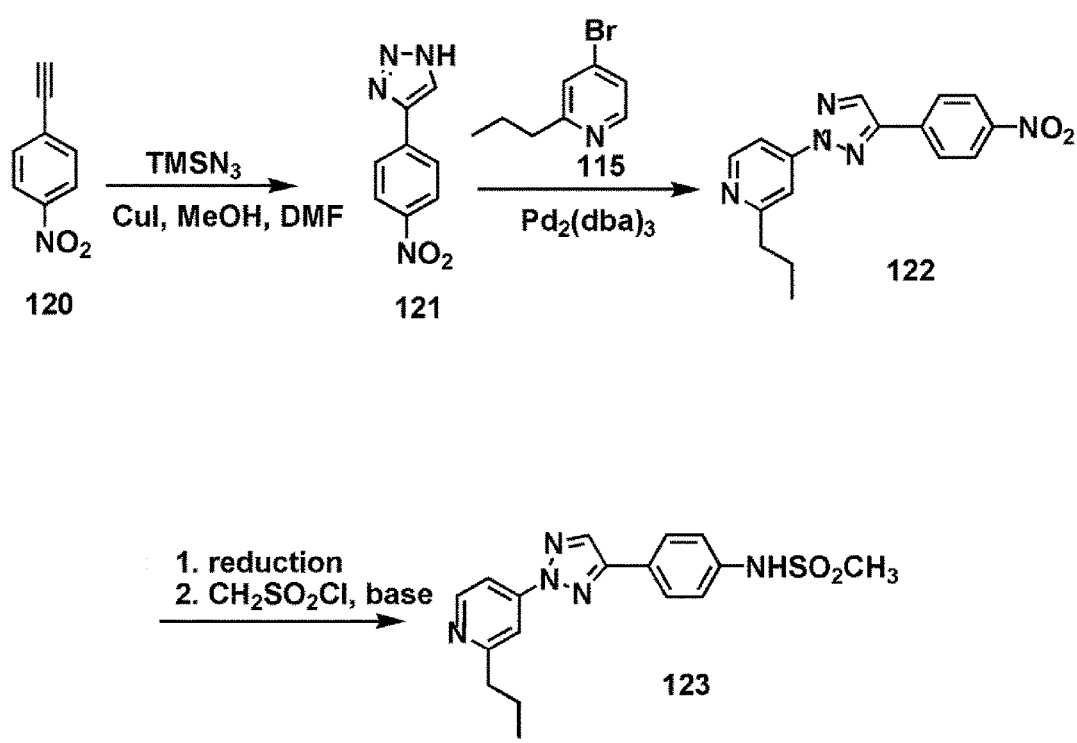
FIG. 23 illustrates the synthesis of triazole derivative 123 from 1-ethynyl-4-nitrobenzene (120).

In a related approach, synthesis of triazole derivative 123 is accomplished as shown in FIG. 23. Reaction of the alkyne 120 with trimethylsilylazide in the presence of CuI yields compound 121 which upon reaction with 115 in the presence of $Pd_2(dba)_3$ catalyst yields compound 122. Reduction of the nitro group and subsequent protection of the resultant amine with methanesulfonyl chloride yields the triazole derivative 123.

Figure 24:
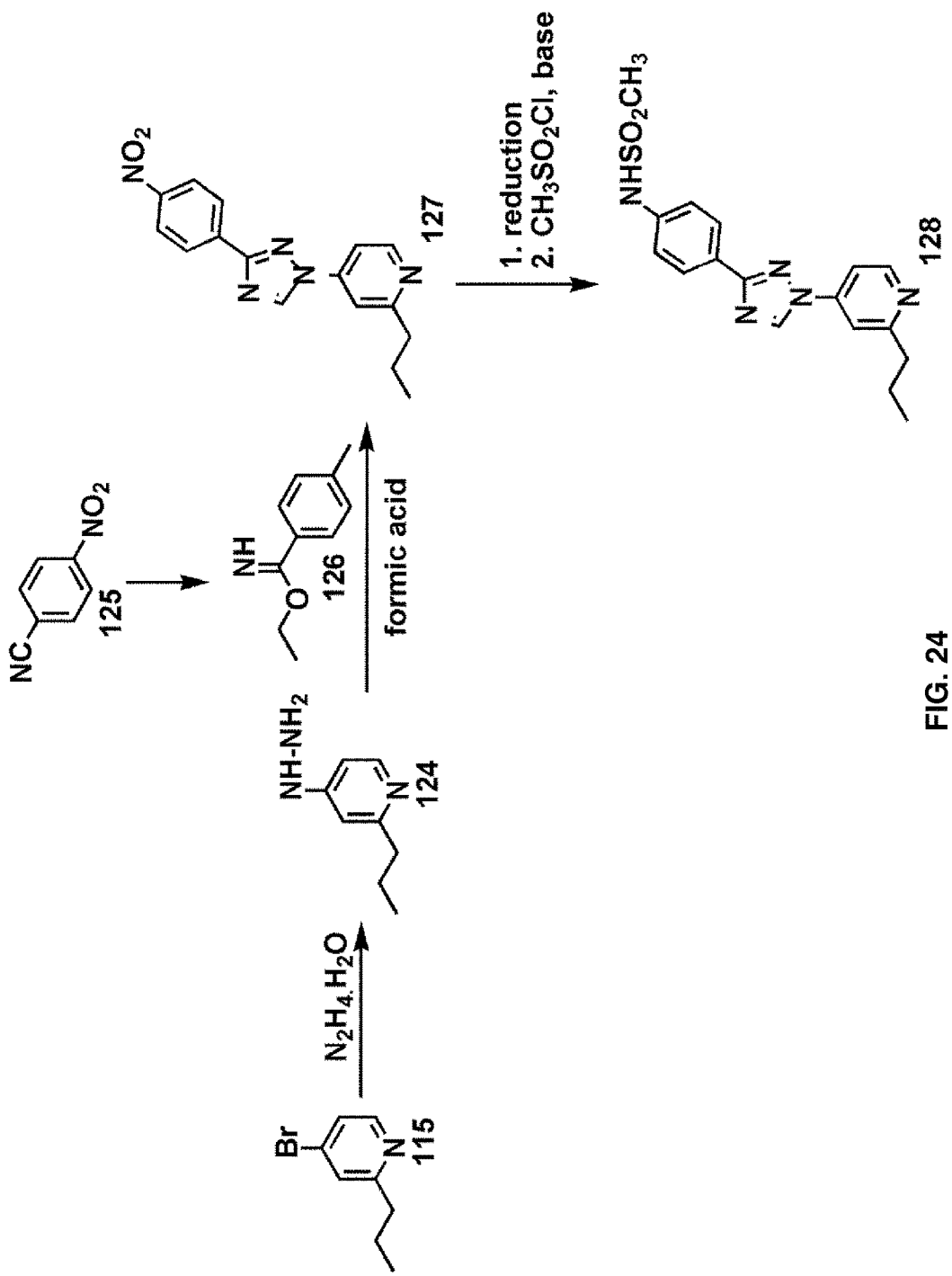
FIG. 24 illustrates the synthesis of triazole derivative 128 from 4-bromopropylpyridine (115).

Synthesis of triazole derivative 128 is shown in FIG. 24. Compound 115 when reacted with hydrazine hydrate yields compound 124. Reaction of 124 with 126, which in turn is obtained from 125, yields the compound 127. Reduction of the nitro group and subsequent protection of the resultant amine with methanesulfonyl chloride yields the triazole derivative 128.

Figure 25:
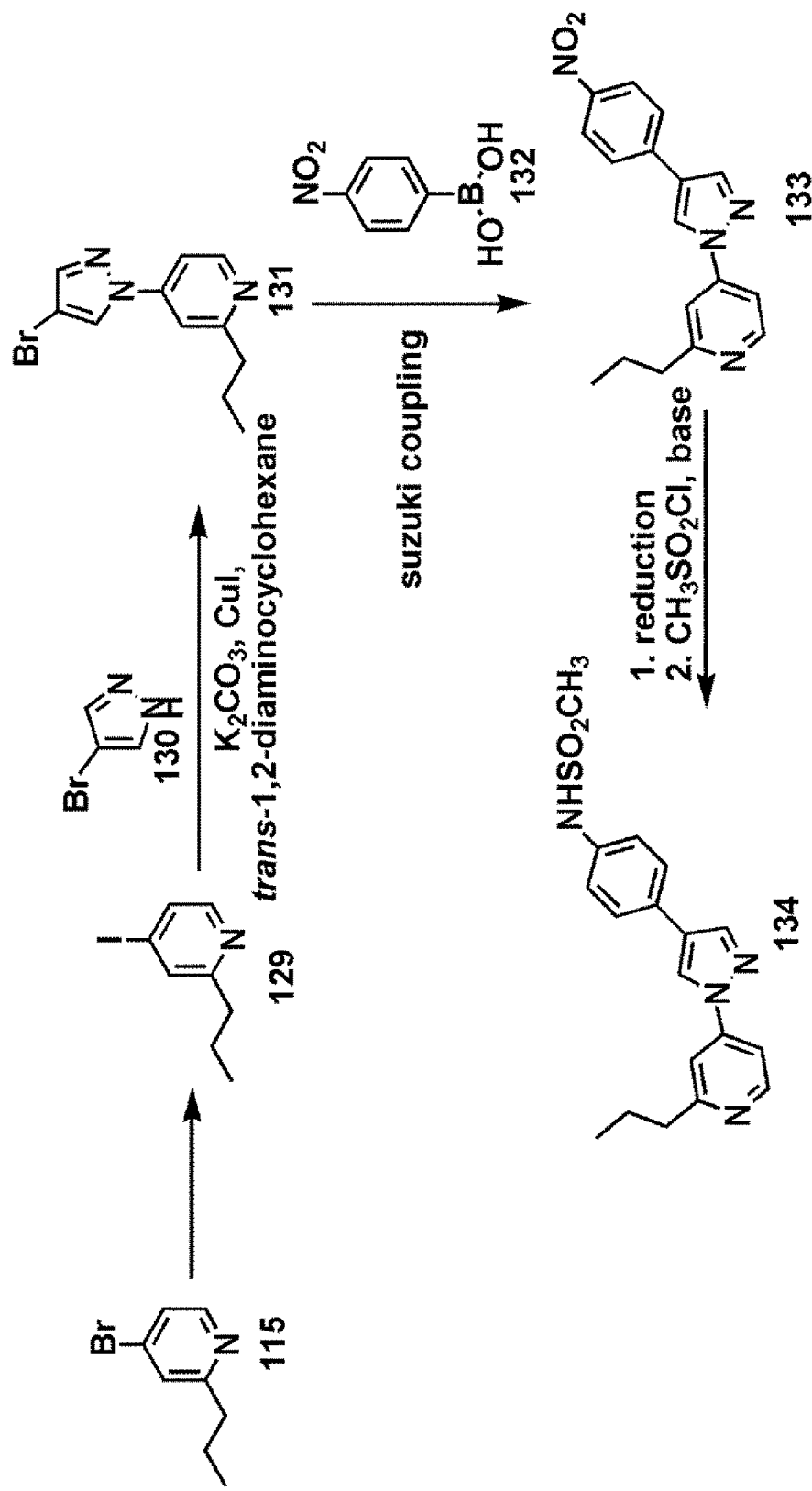
FIG. 25 illustrates the synthesis of pyrazole derivative 134 from 4-bromopropylpyridine (115).

Synthesis of pyrazole derivative 133 is shown in FIG. 25. Compound 129, which is obtained from compound 115, when reacted with 130 in the presence of CuI and $K_2CO_3$ yields compound 131. Compound 131 is subjected to Suzuki coupling reactions with boronic acid 132, to yield compound 133. Reduction of the nitro group and subsequent protection of the resultant amine with methanesulfonyl chloride yields the triazole derivative 133.

Figure 26:
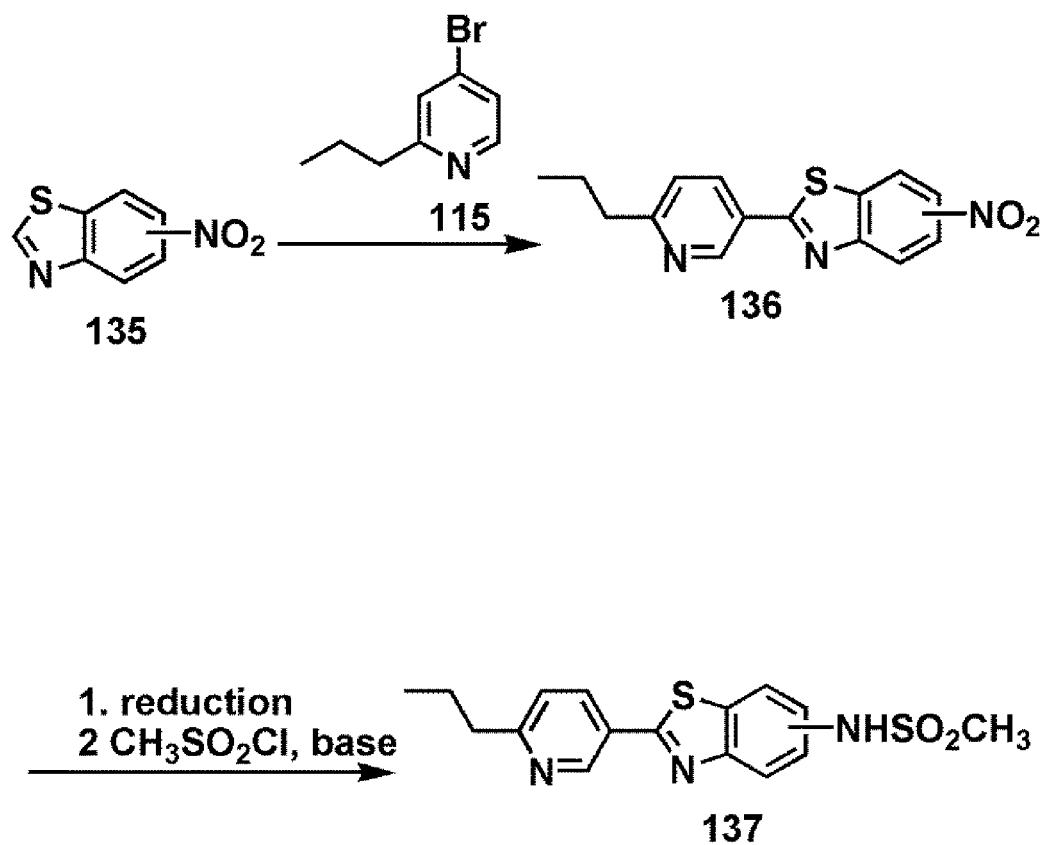
FIG. 26 illustrates the synthesis of benzothiazole derivative 137 from benzothiazole (135).

Synthesis of benzothiazole derivative 137 is shown in FIG. 26. Nitro-substituted benzothiazole 135 reacts with compound 115 to produce compound 136. Reduction of the nitro group and subsequent protection of the resultant amine with methanesulfonyl chloride yields the triazole derivative 137.

Figure 27:
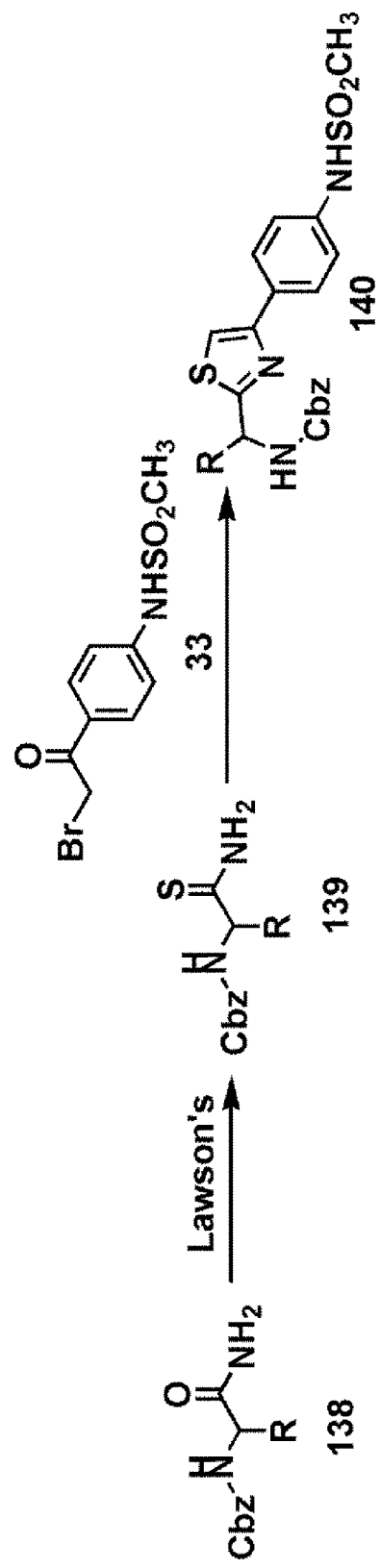
FIG. 27 illustrates the synthesis of thiazole derivative 140 from aminoacetamide derivative (138).

Synthesis of thiazole derivative 140 is shown in FIG. 27. The amide 138 is converted to the thioamide 139 by reaction with Lawson's reagent. The thioamide 139 then react with the acyl bromide 33 to yield the thiazole derivative 140.

Figure 28:
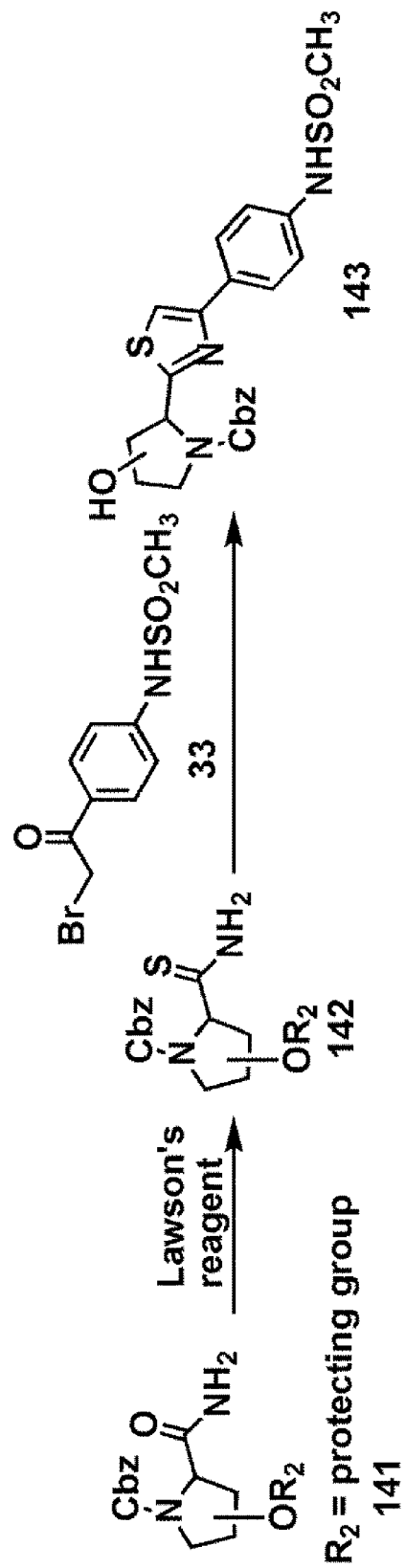
FIG. 28 illustrates the synthesis of thiazole derivative 143 from pyrrolidine derivative (141).

Synthesis of thiazole derivative 143 is shown in FIG. 28. The amide 141 is converted to the thioamide 142 by reaction with Lawson's reagent. The thioamide 142 then react with the acyl bromide 33 to yield the thiazole derivative 143.

Figure 29:
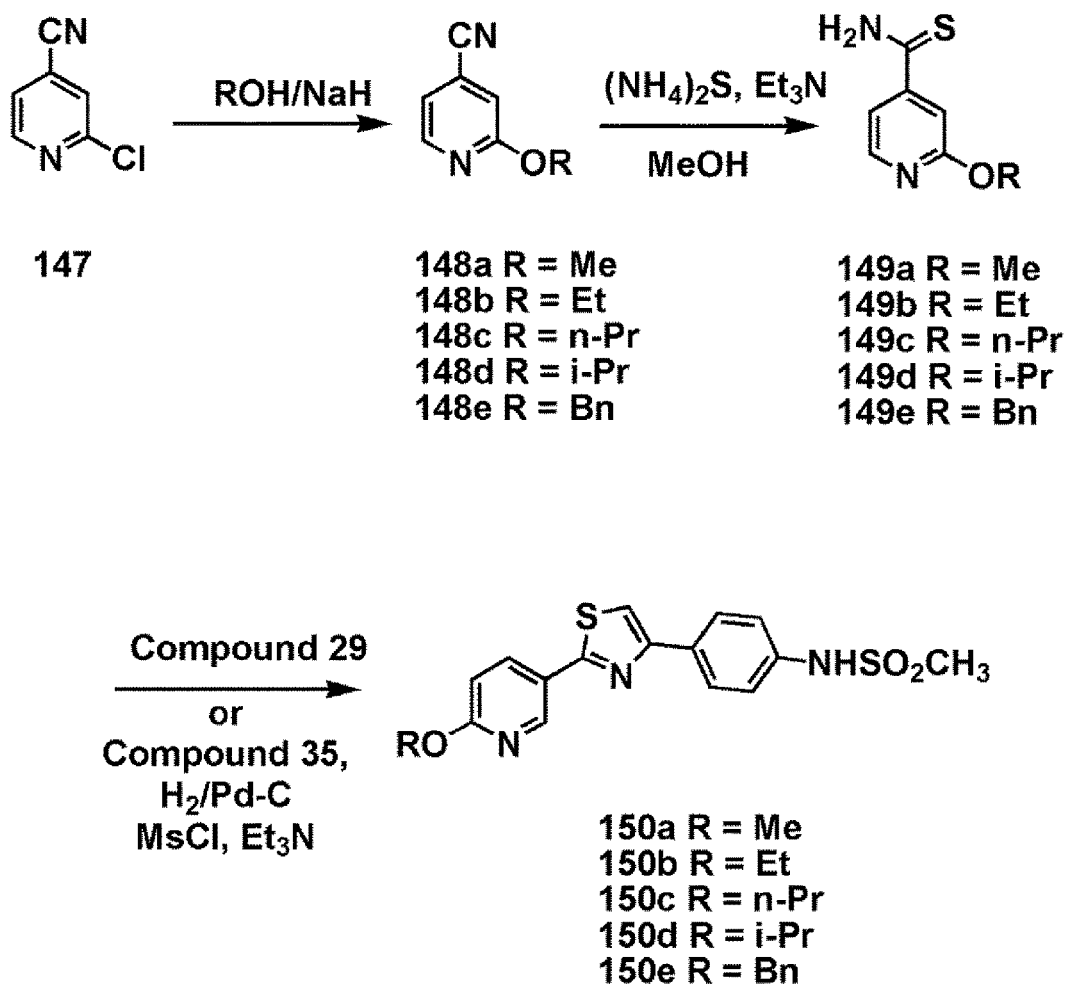
FIG. 29 illustrates the synthesis of thiazole derivative 150a-150e from pyridine 147.
Figure 30:
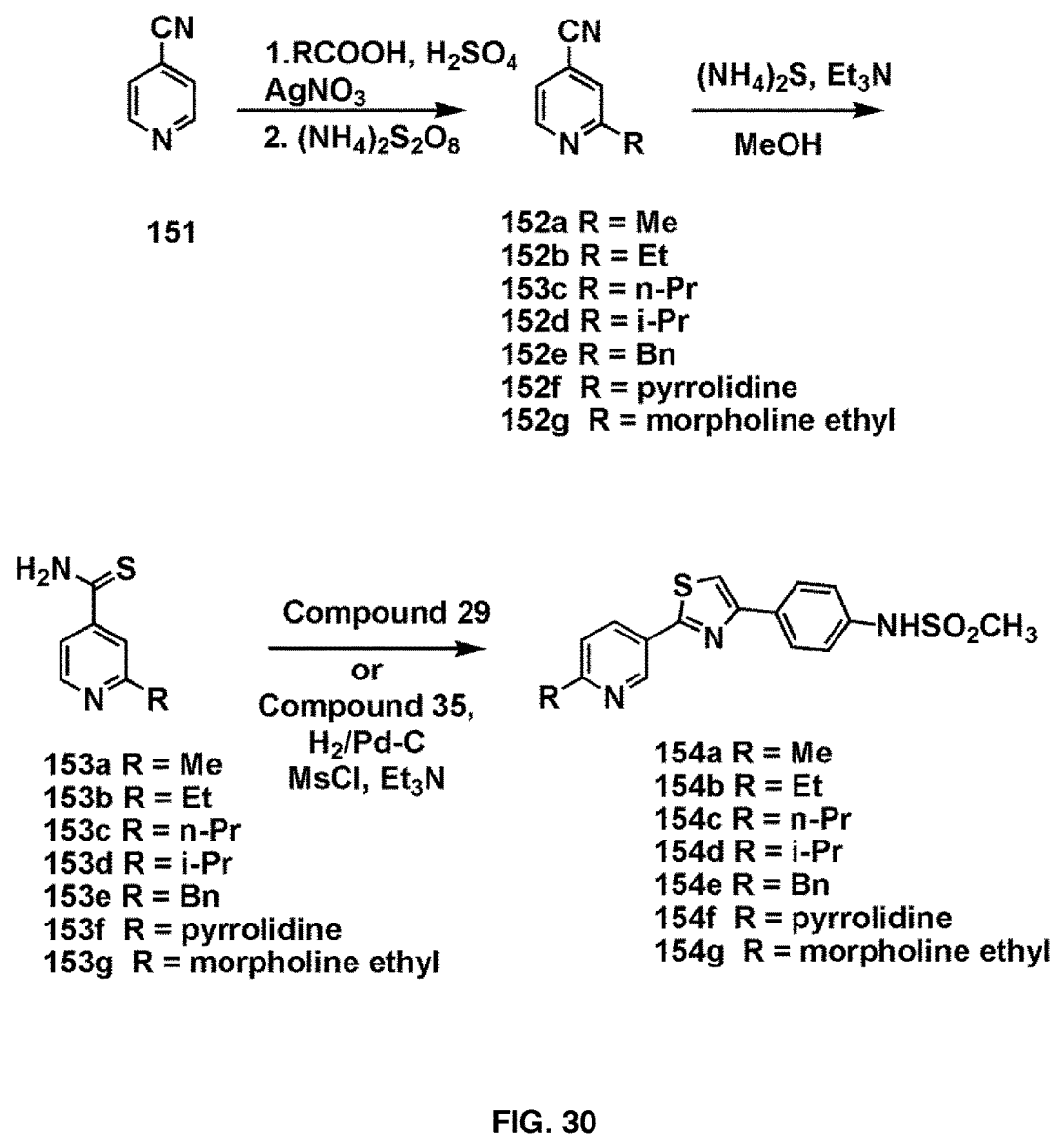

FIGS. 29 and 30 illustrate the synthesis of several thiazole derivatives containing 2 several alkyl and alkoxy substituted pyridines. Pyridine 147 is converted to thioamides 149a-149e. thioamides 149a-149e are then converted to the thiazoles 150a-150e (FIG. 29) following similar reactions as discussed above. Using alkyl-substituted pyridines 152a-152e, synthesis of thiazole derivatives 154a-154g are accomplished as shown in FIG. 30.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

General Method for the Synthesis of Compounds 11-16

A 1:1 mixture of 2-propylpyridine derivatives 1-3 and nitro-substituted benzoyl bromide 4 were heated to 70° C. in EtOH for 1 h and cooled to room temperature. The reaction mixture was extracted with ethyl acetate, washed with aqueous $NaHCO_3$ and filtered. The organic fractions were dried over anhydrous $Na_2SO_4$ and evaporated under vacuo. The crude mixture was subjected to reduction conditions to obtain the corresponding amine. Protection of the amine with methanesulfonyl chloride afforded the compounds 11-13.

Alternatively, reductive amination with formaldehyde and subsequent protection of the resultant secondary amine with methanesulfonyl chloride yielded the compounds 14-16.

Synthesis of Compound 79b

Pyrrolidine-2-carbothioamide (78) was prepared by the reaction of Pyrrolidine-2-carboxamide (77) with Lawson's reagent. Compound 78 was then heated with bromo ketone 33 at 70° C. in ethanol for 1 h. The reaction was cooled to room temperature and the reaction mixture was extracted with EtOAc and washed with aqueous sodium bicarbonate. The organic layers were separated and dried under vacuo to produce compound 79b.

Synthesis of Compound 82

Piperidine-3-carbothioamide (82) was prepared by the reaction of Piperidine-3-carboxamide (80) with Lawson's reagent. Compound 82 was then reacted with bromo ketone 33 at 70° C. in ethanol for 1 h. The reaction was cooled to room temperature and the reaction mixture was extracted with EtOAc and washed with aqueous sodium bicarbonate. The organic layers were separated and dried under vacuo to produce compound 82.

Example 2

Effect of Compounds on mRNA

Figure 31A:
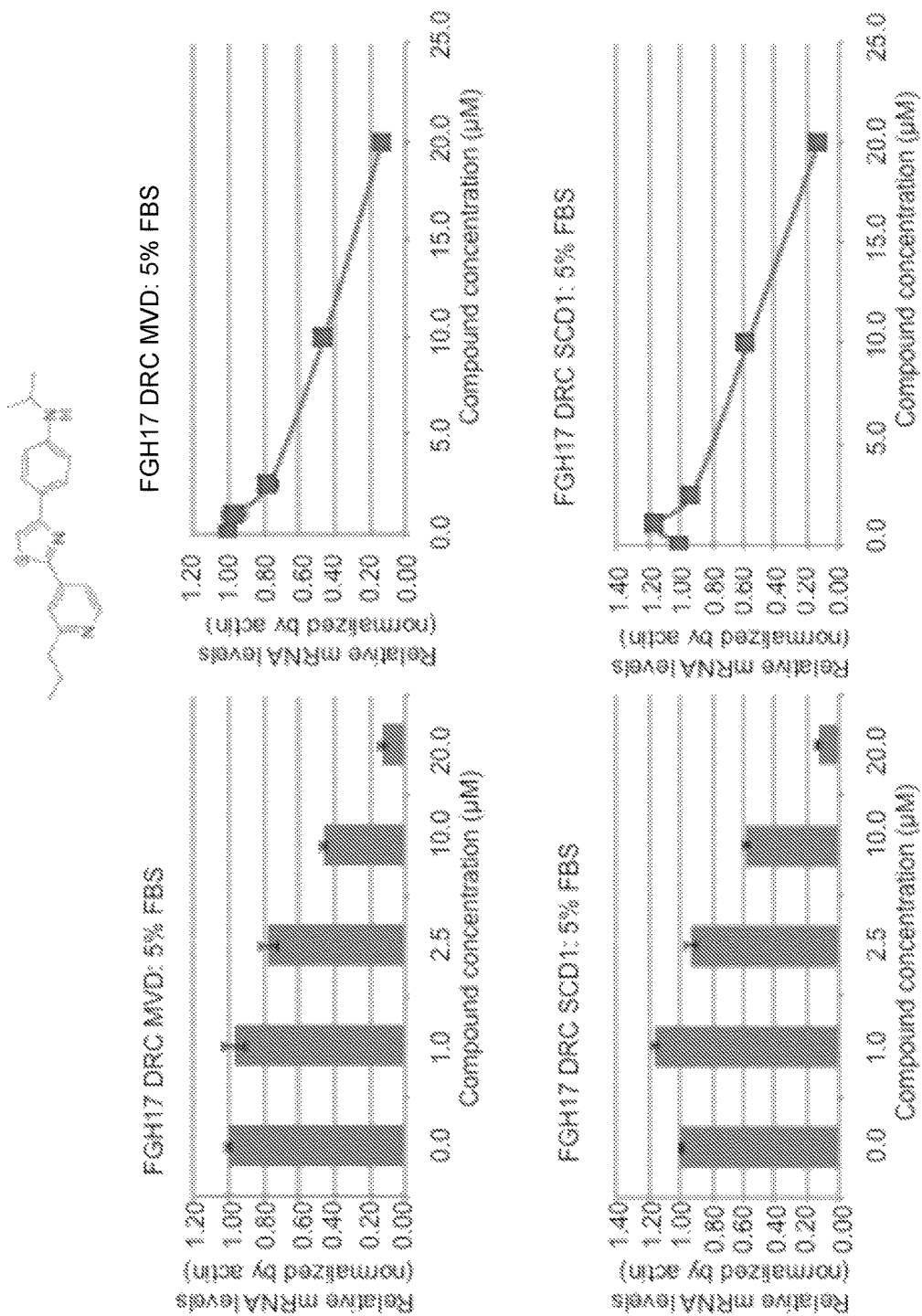
FIGS. 31A-31R show the effects of various compounds on mRNA levels drug resistant Hep3B cells.
Figure 31B:
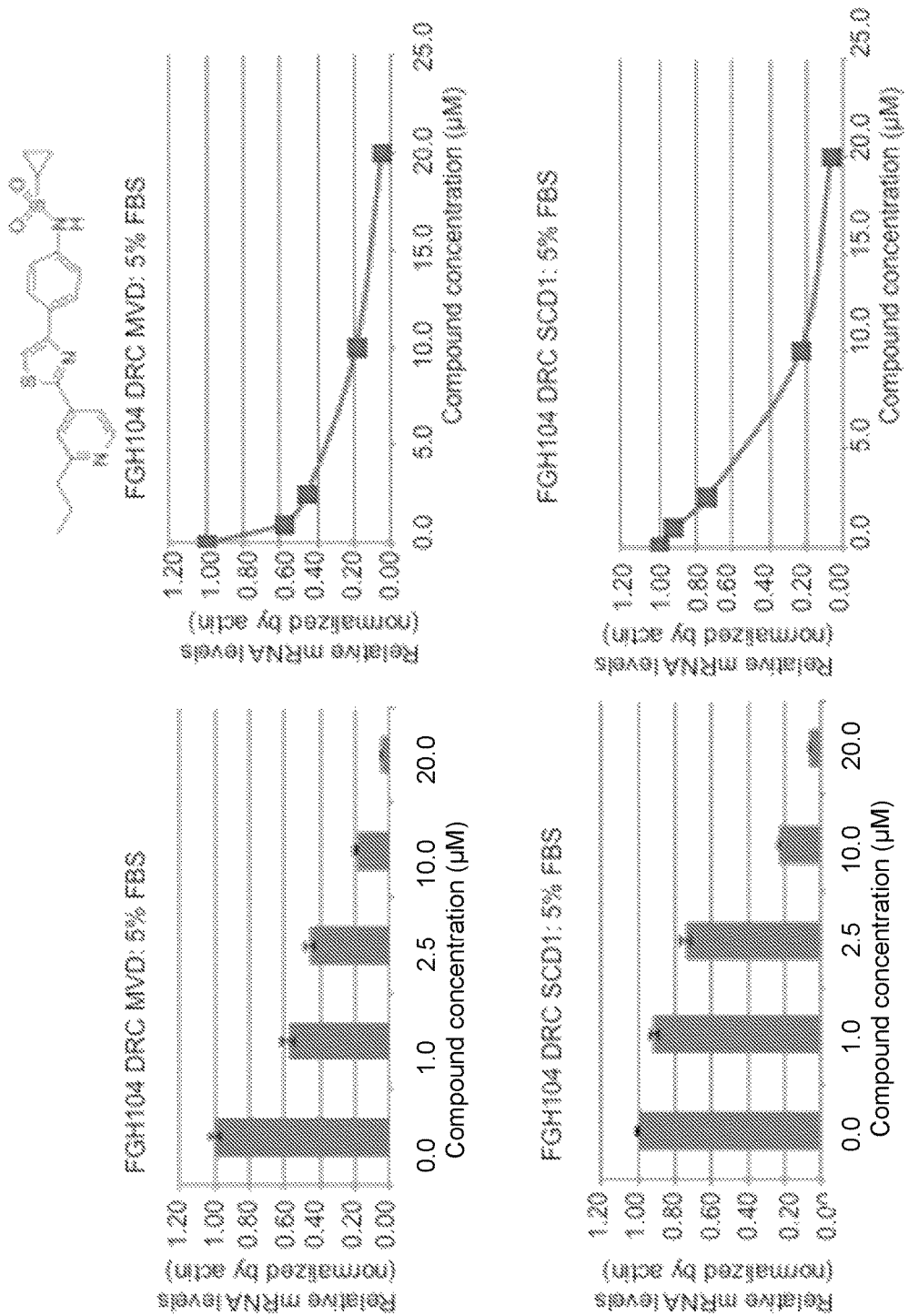
Figure 31C:
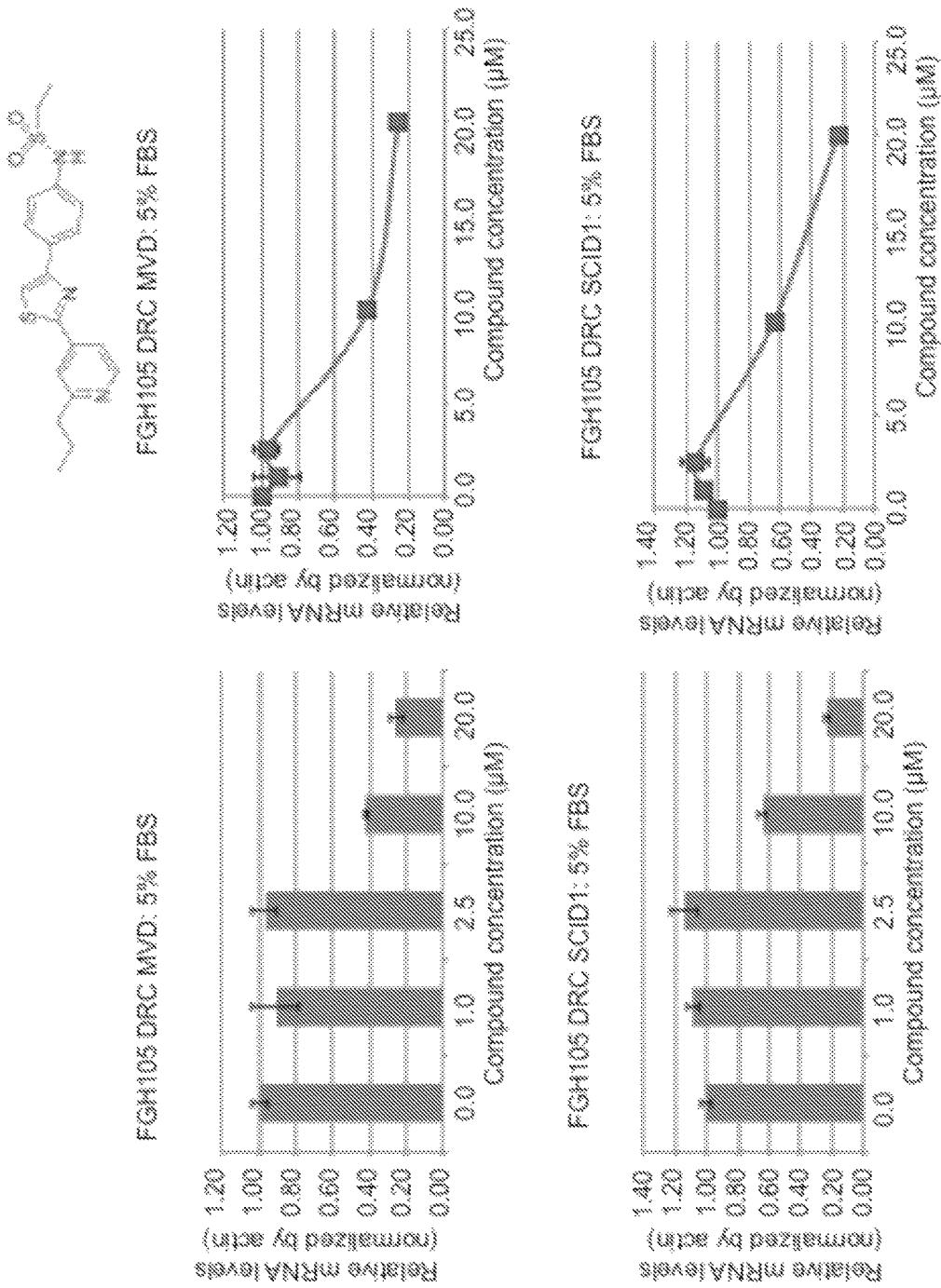
Figure 31D:
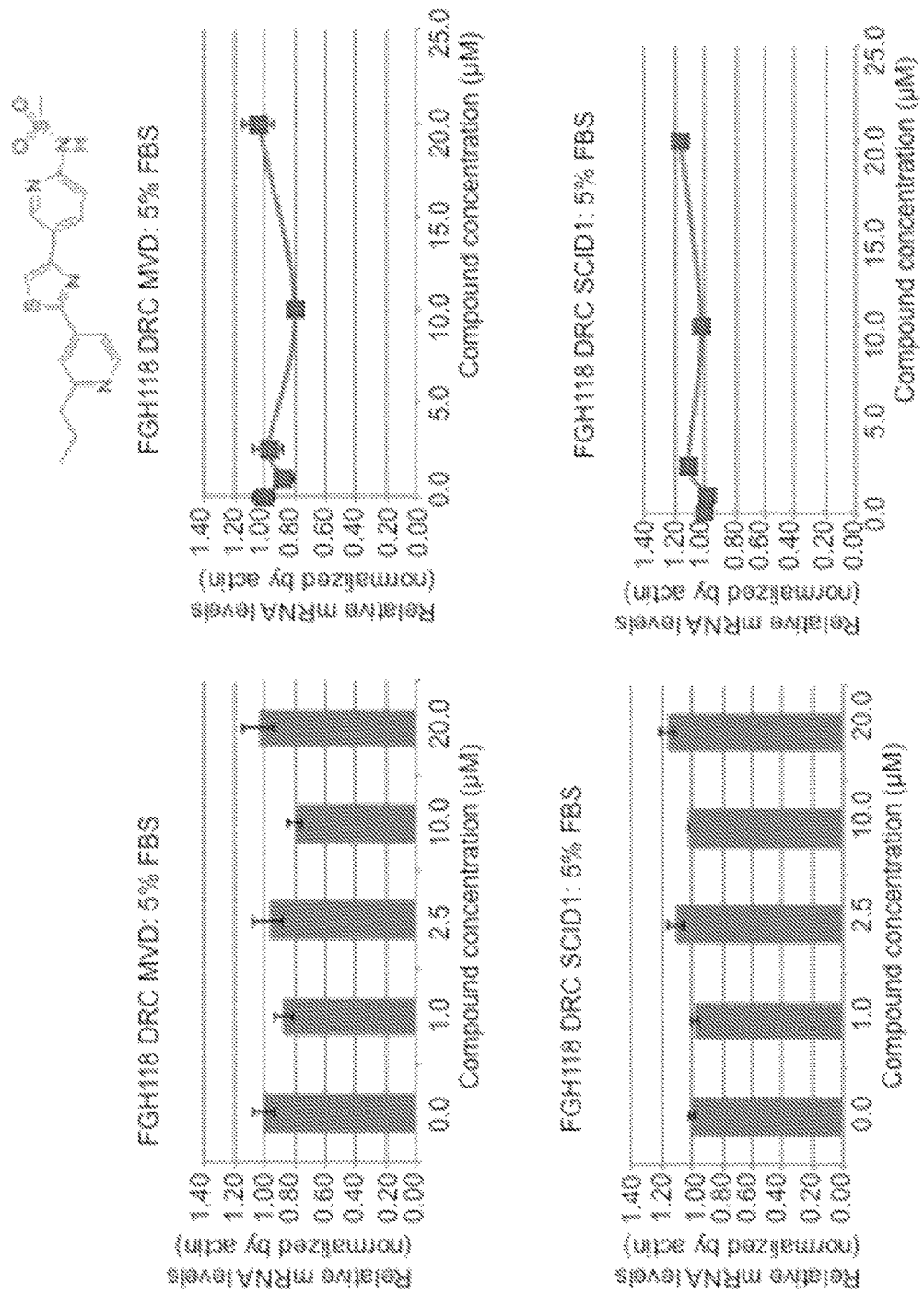
Figure 31E:
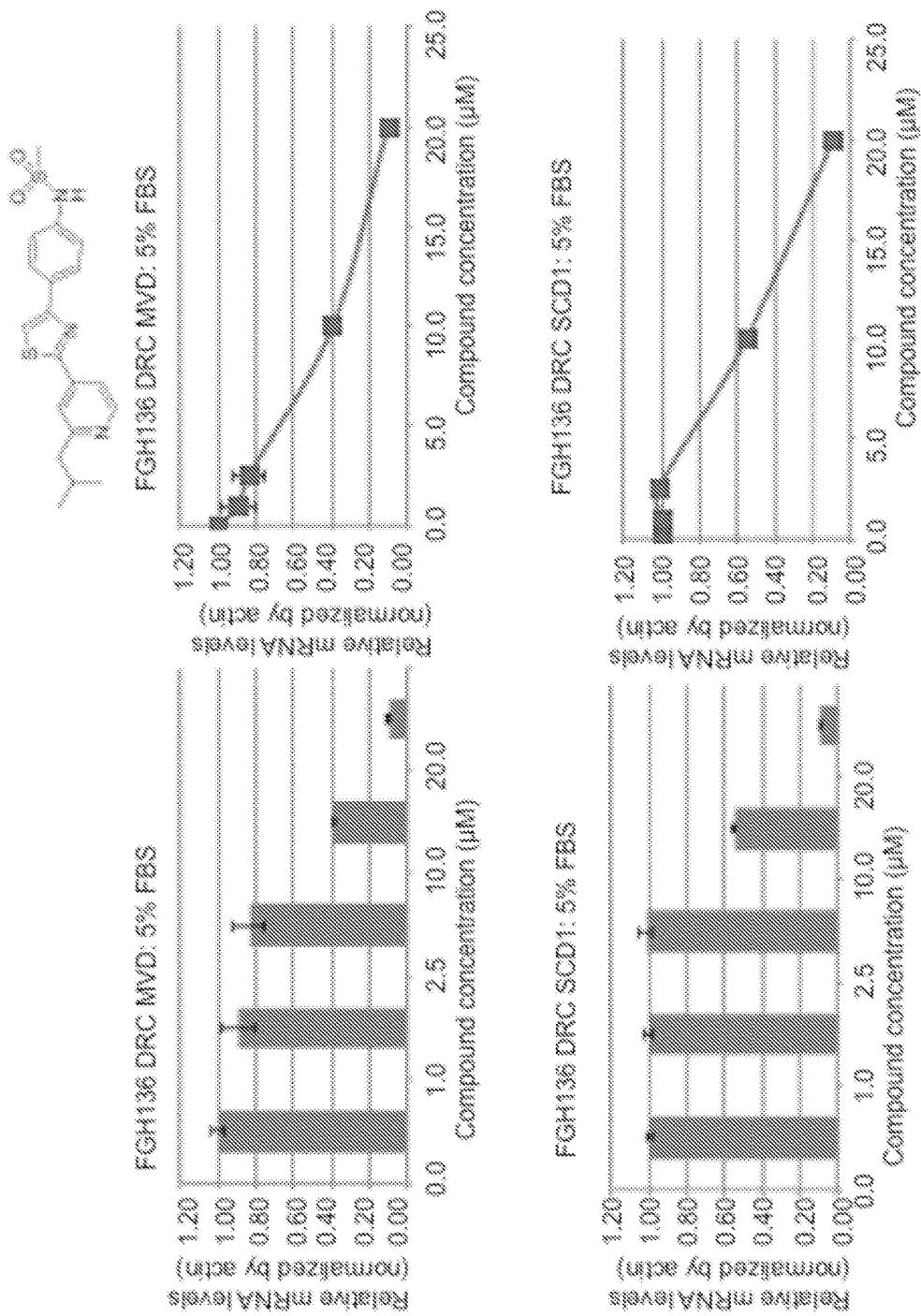
Figure 31F:
Figure 31F:
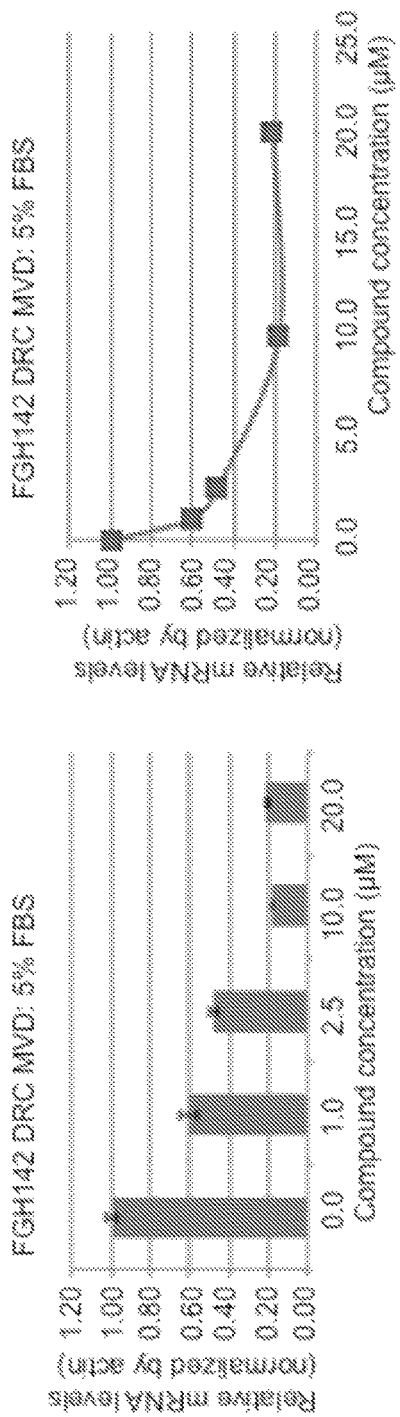
Figure 31F:
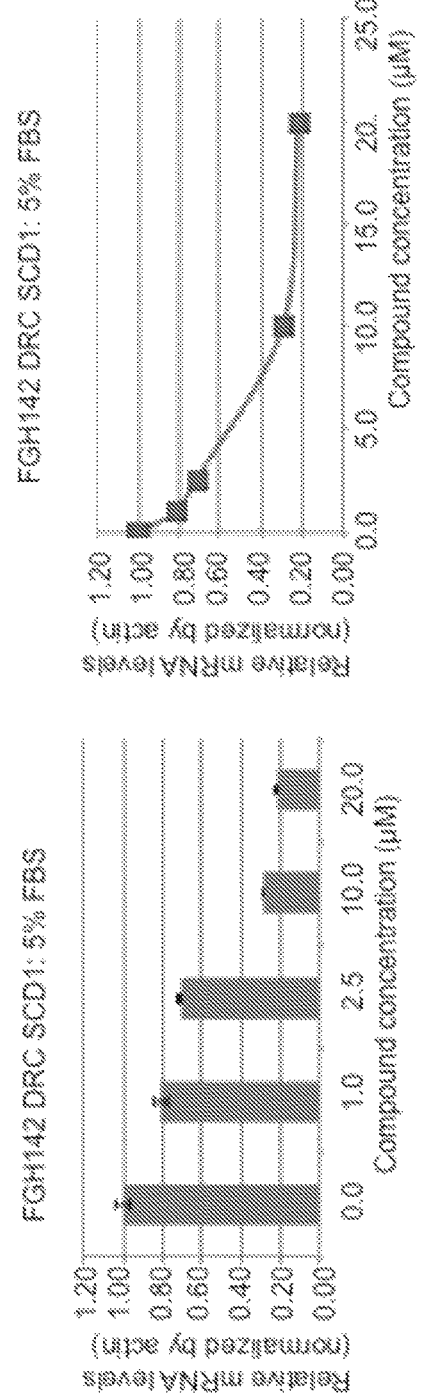
Figure 31G:
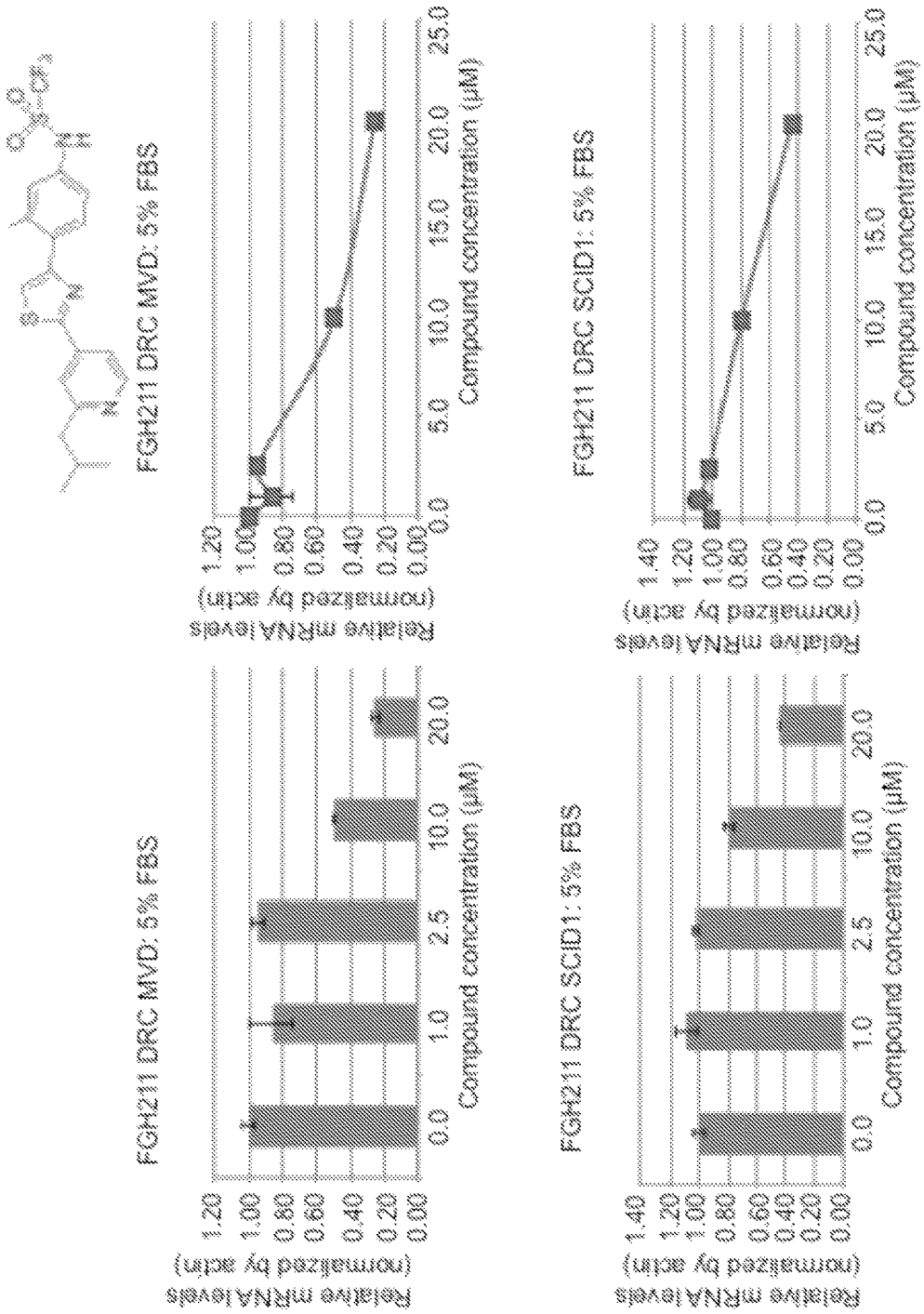
Figure 31H:
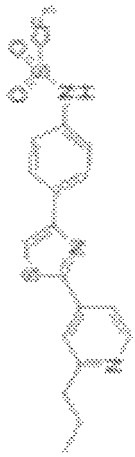
Figure 31H:
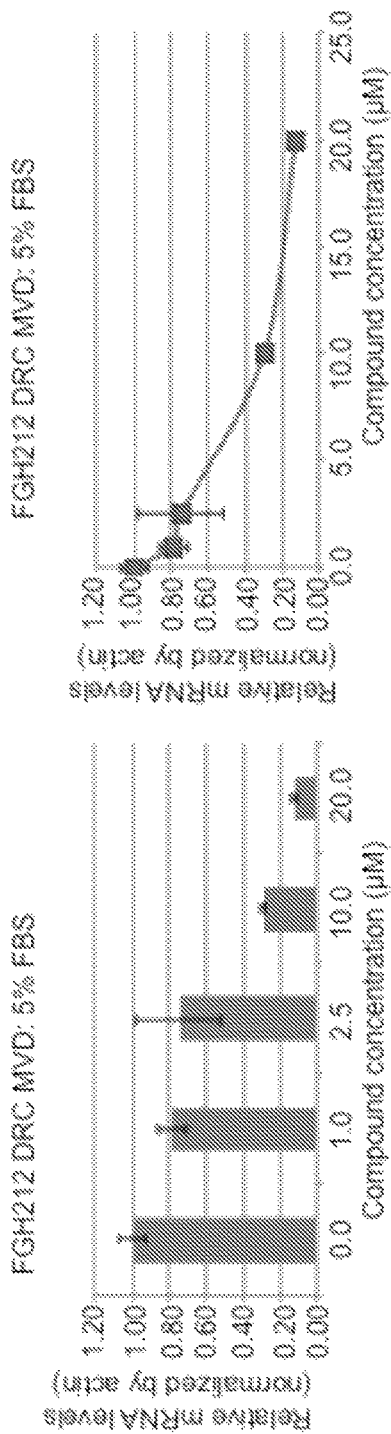
Figure 31H:
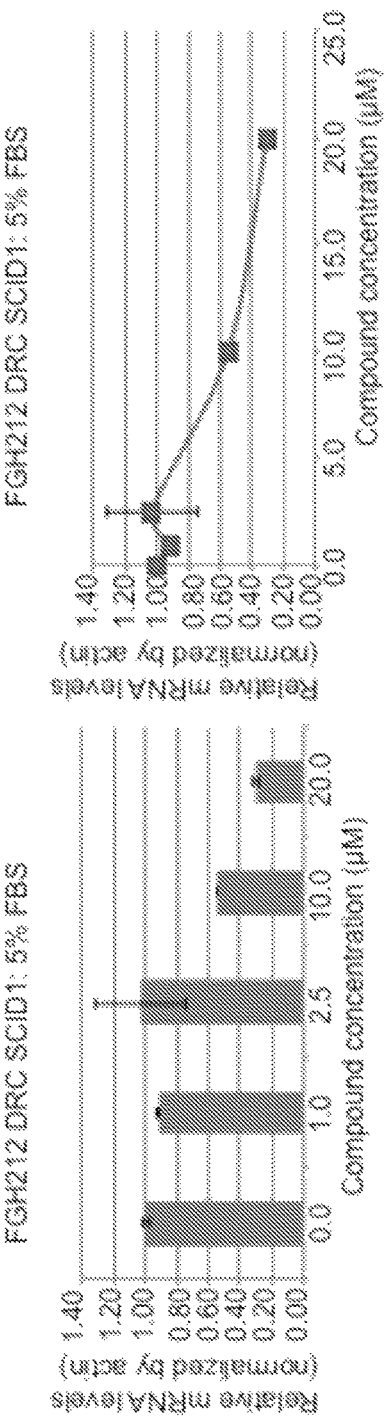
Figure 31:
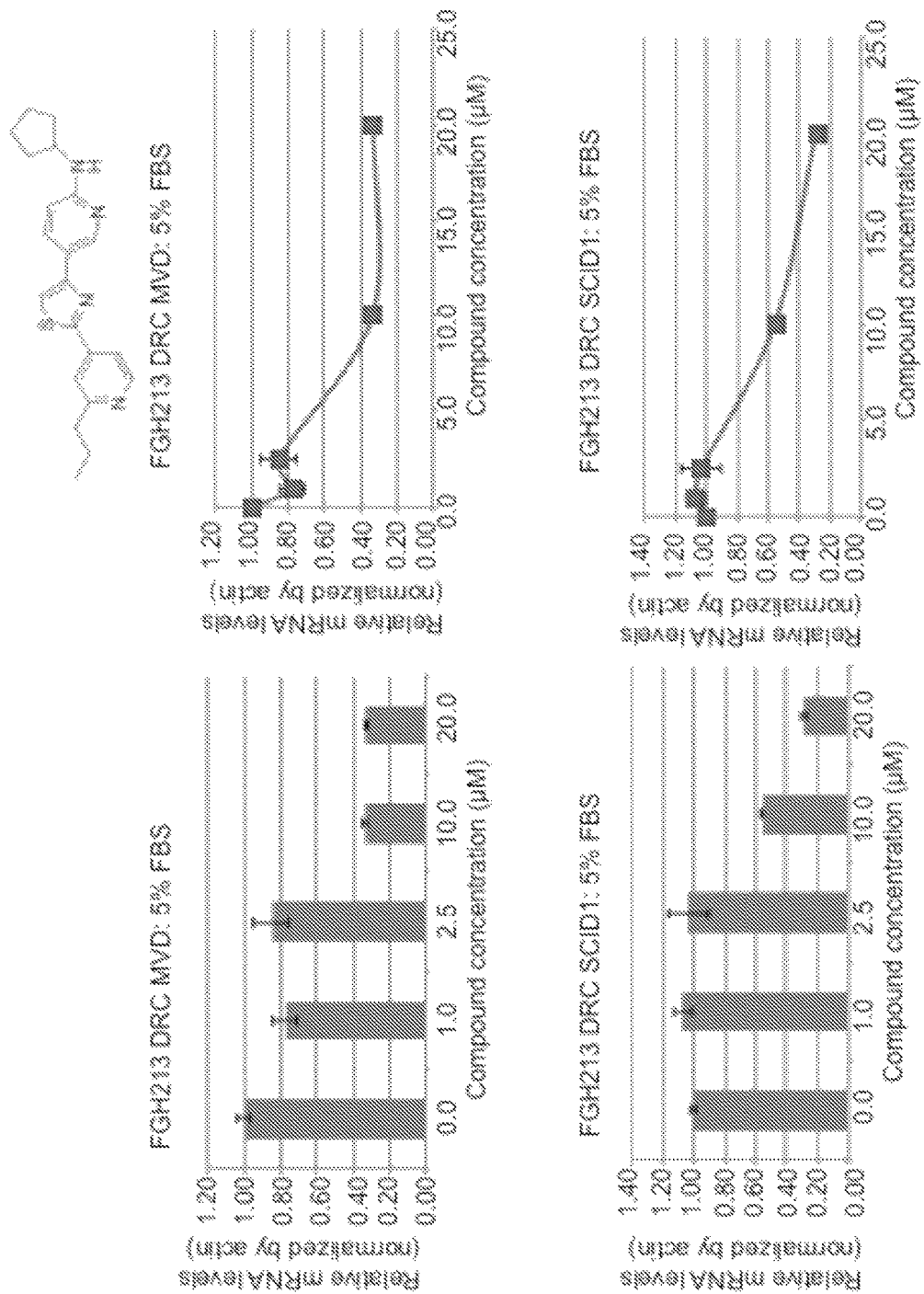
Figure 31J:
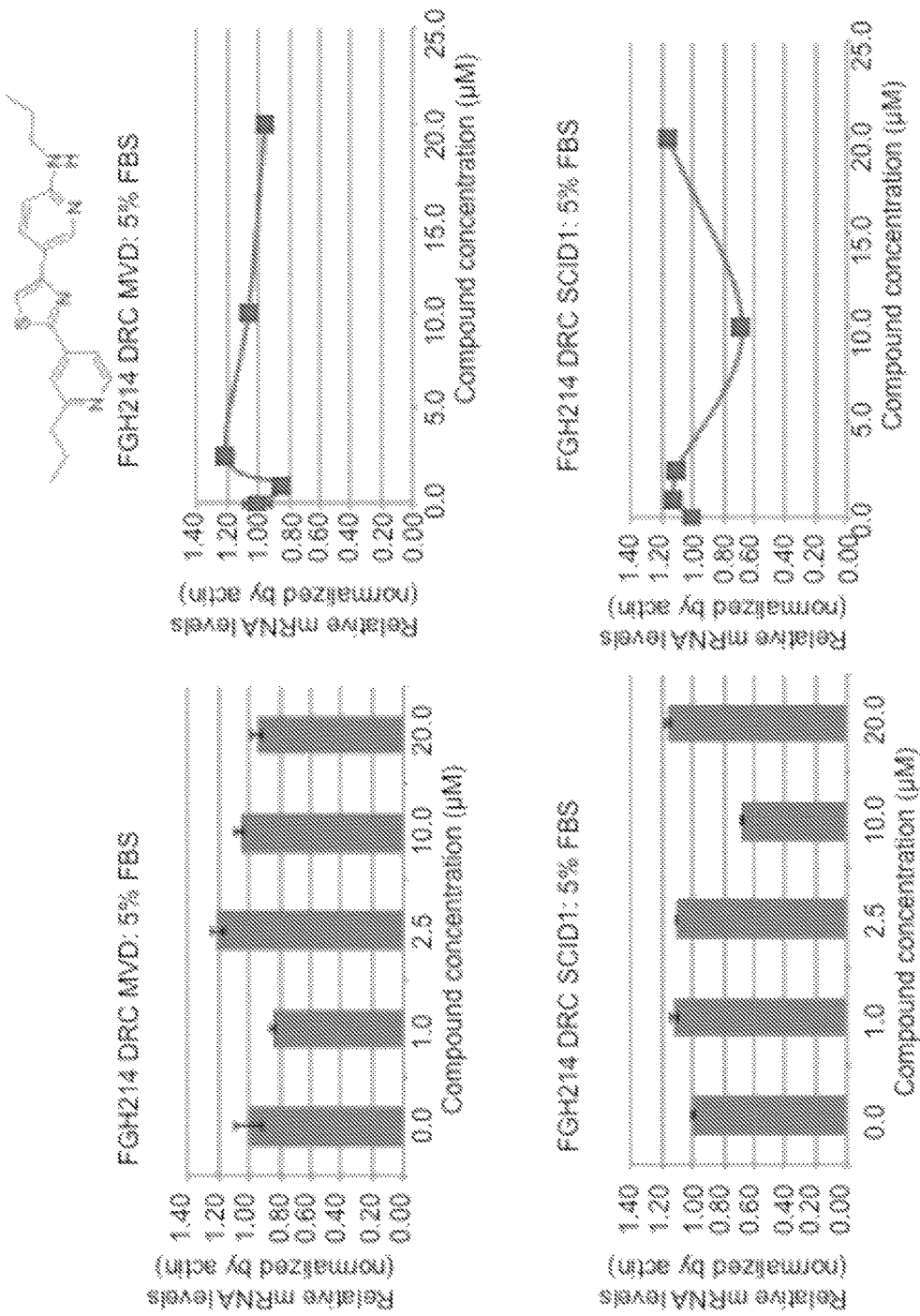
Figure 31K:
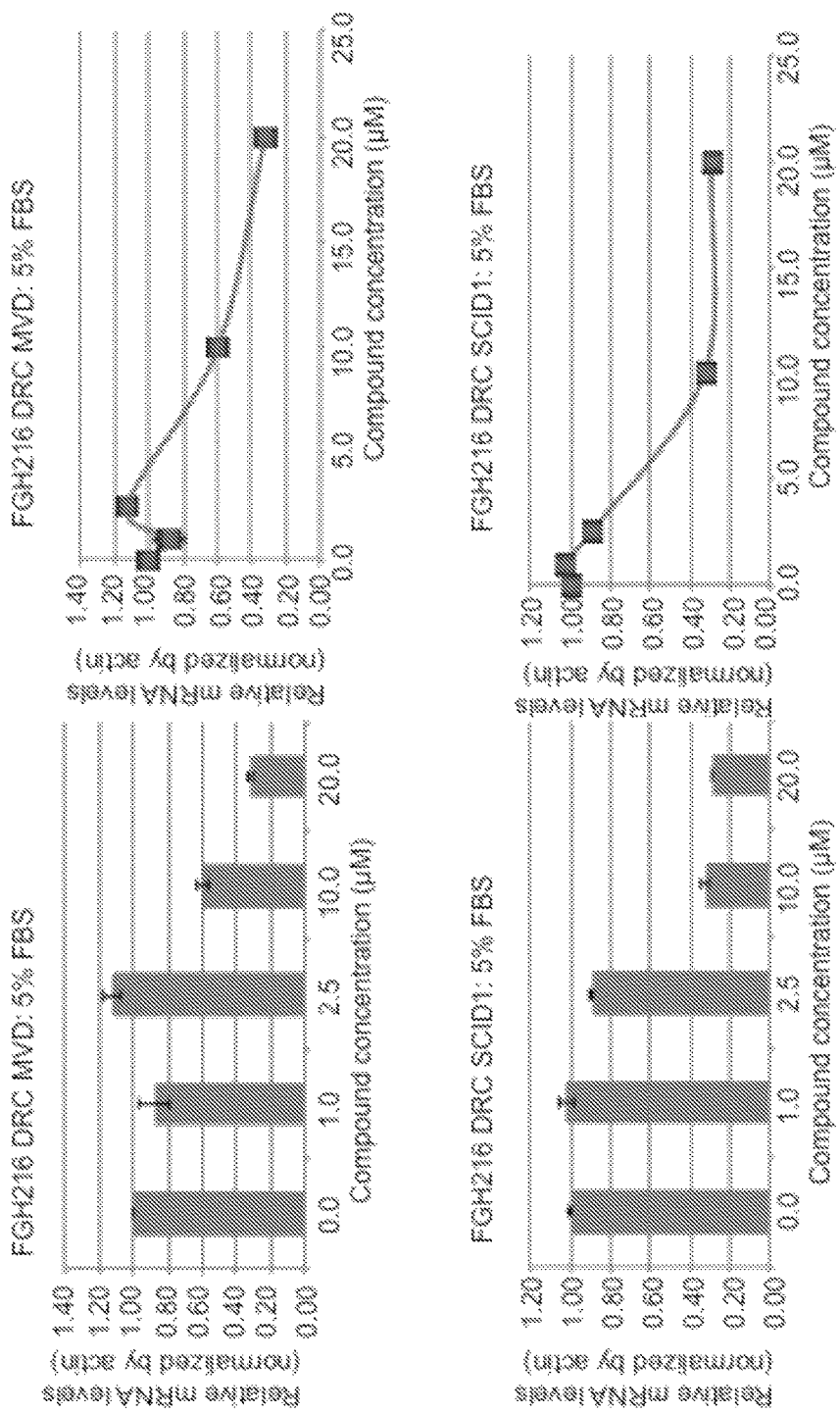
Figure 31L:
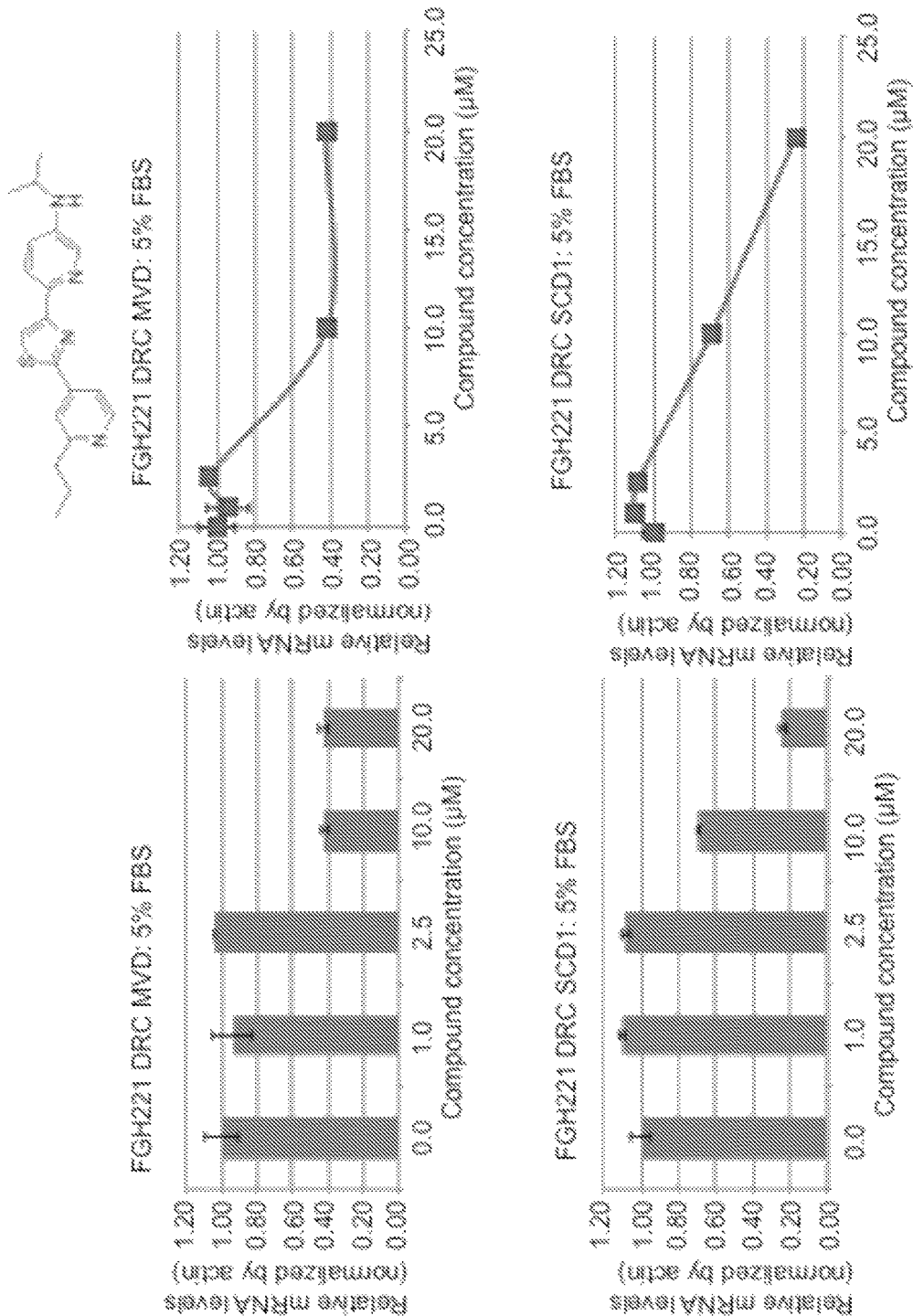
Figure 31M:
Figure 31M:
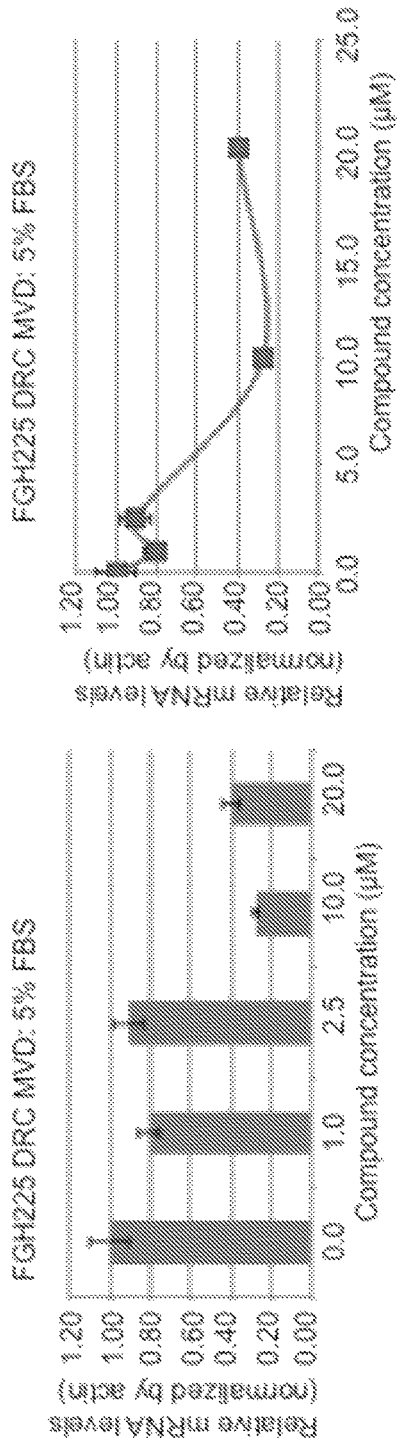
Figure 31M:
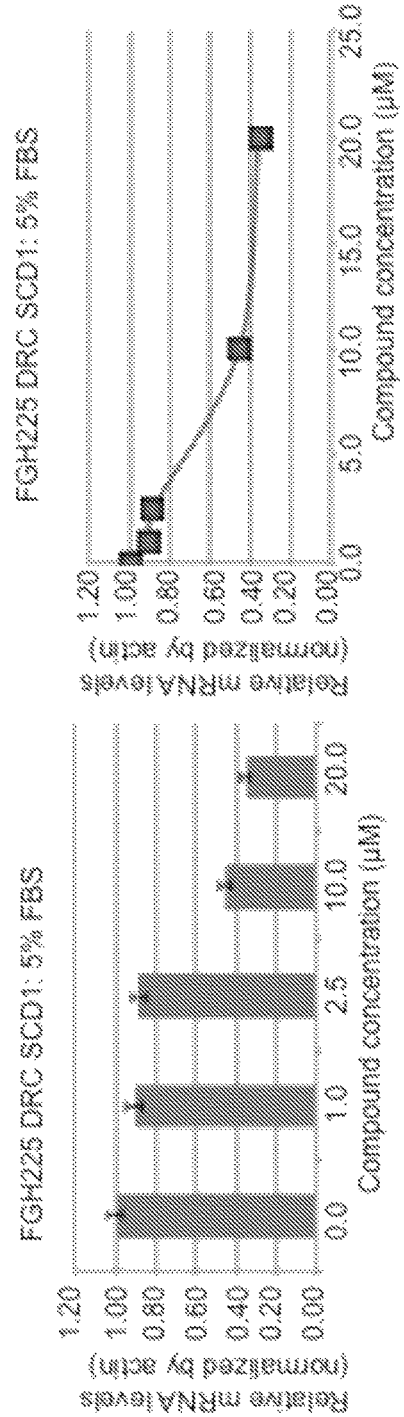
Figure 31N:
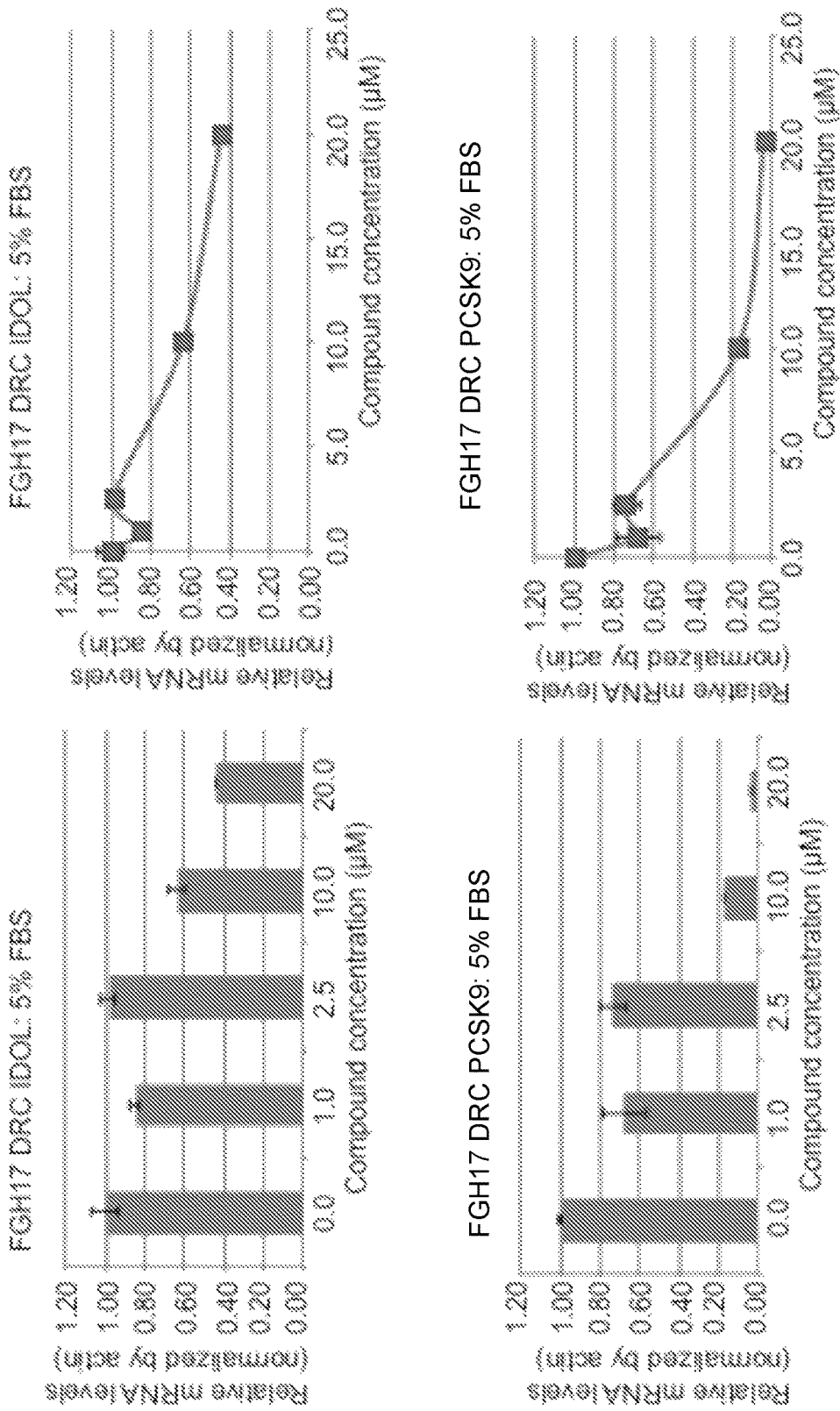
Figure 31O:
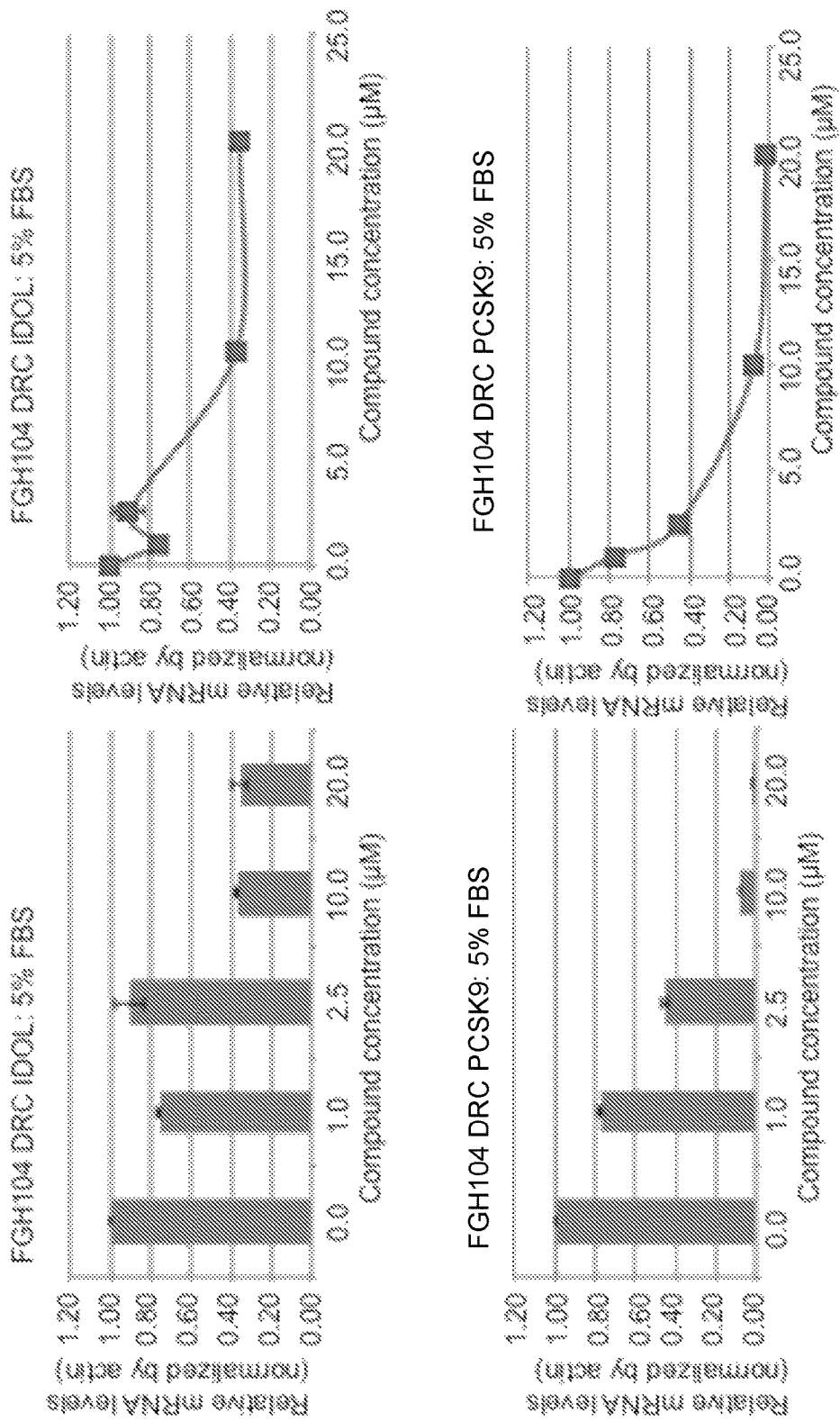
Figure 31P:
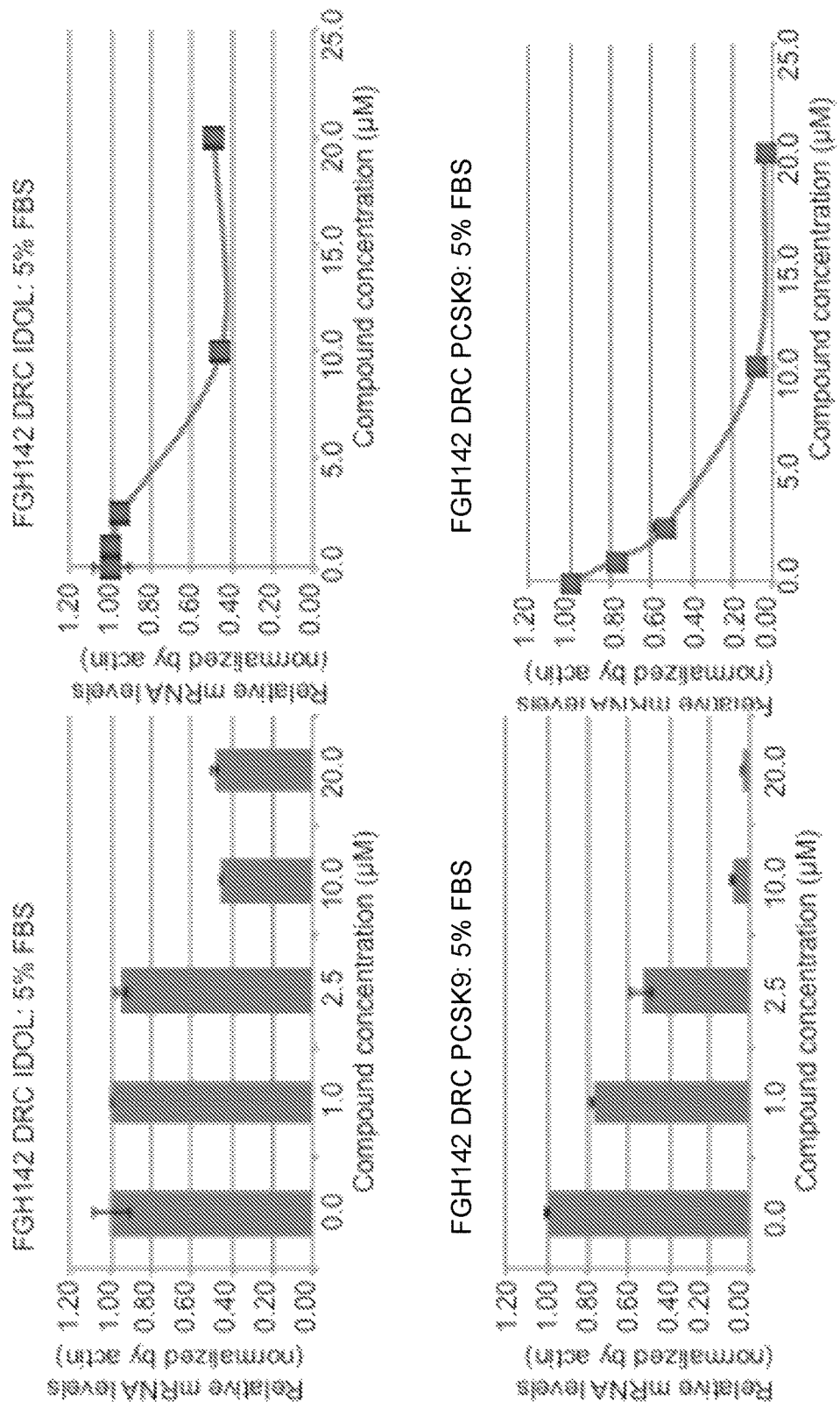
Figure 31Q:
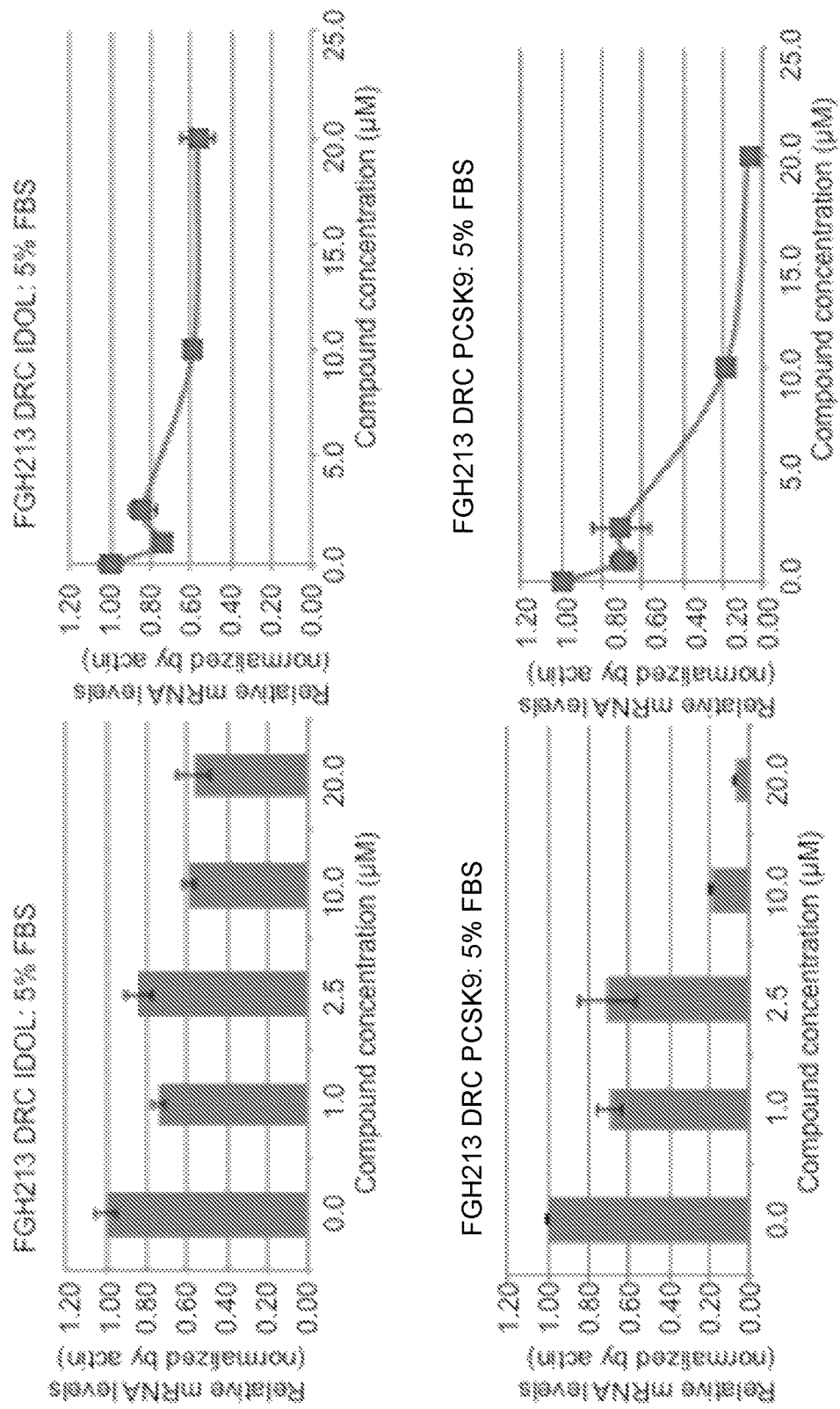
Figure 31R:
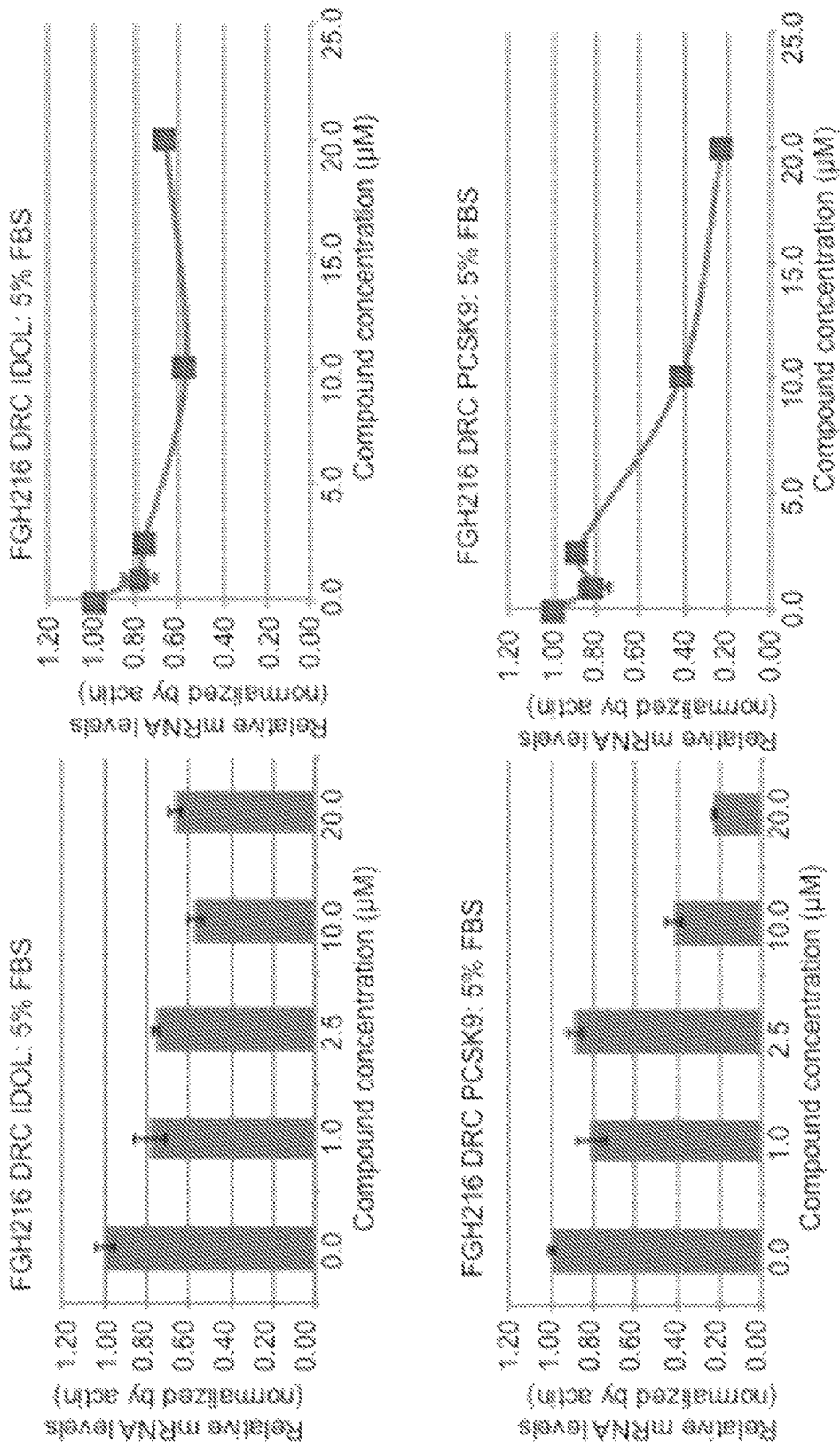

Drug resistant Hep3B cells (DRC) in culture medium containing 5% FBS were incubated with the indicated compounds at the indicated concentrations. The efficacy of these compounds in inhibiting mRNA expression for the genes coding for mevalonate diphosphate decarboxylase (MVD), stearoyl-CoA desaturase-1 (SCD1), Inducible degrader of the low-density lipoprotein receptor (IDOL) and Proprotein Convertase Subtilisin/Kexin Type 9 (PCSK9) are shown. All data are normalized to mRNA levels for the cytoskeletal protein, actin (FIGS. 31A-31S).

Example 3

Compound Structures

Figure 32:
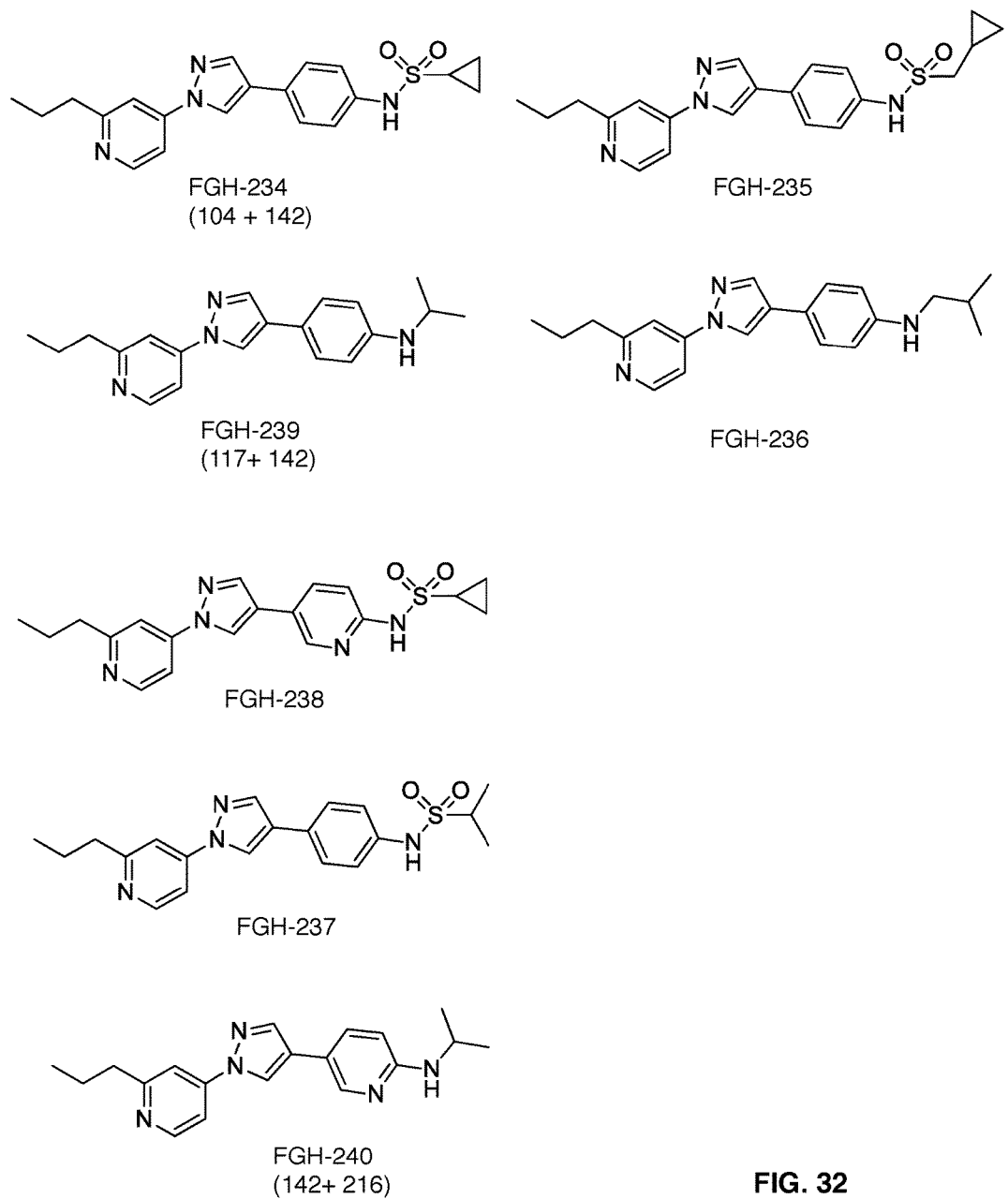
FIG. 32 shows the chemical structures of various compounds of the instant invention.

Other compounds considered for the instant invention are shown in FIG. 32.

REFERENCES

Narasimhamurthy N. et al. *Tetrahedron Lett.* 1986, 27, 3911.
WO 2004091610 A1 (Khatuya, H. et al.) Oct. 28, 2004.

WO 2008026046 A1 (Wager, T T et al.) Mar. 6, 2008.
Turner, G L et al. *Angew. Chem. Int. Ed.* 2007, 42, 7996.
US 20060148722 (Lewis, J et al.) Jul. 6, 2006.
Richardson, C et al. *J. Org. Chem.* 2007, 72, 4750.
Chen, Y et al. *J. Organomet. Chem.* 2014, 749, 215.
Ueda, S. et al. *Angew. Chem. Int. Ed.* 2011, 38, 8944.
US 20090318436 A1 (Albrecht, B.) Dec. 24, 2009.
WO 2005049033 A1 (Block, M H et al.) Jun. 2, 2005.

What is claimed is:

1. A compound selected from the group consisting of:

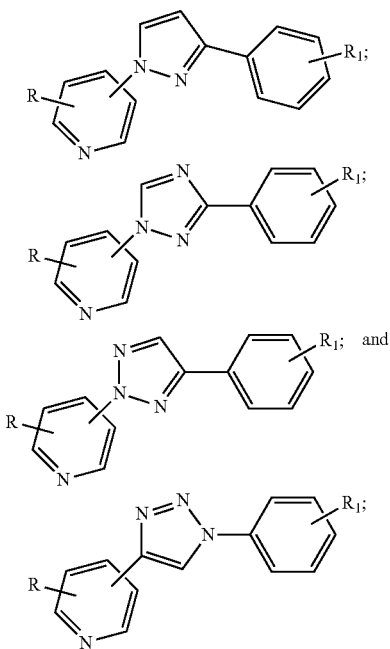

where
R is ethyl, n-propyl, isopropyl, —O—$C_{1-3}$ alkyl, unsubstituted pyrrolidinyl, or unsubstituted morpholinyl;
$R_1$ is H, halogen, —OH, —O—$C_{1-3}$ alkyl, —OC(O)$R_2$, or —N$R_3R_4$;
$R_2$ is $C_1$-$C_3$ alkyl or aryl;
$R_3$ is H, $C_1$-$C_3$ alkyl, -alkylcyclopropane, cyclohexyl, benzyl, or —SO$_2$—$R_5$;
$R_4$ is H, $C_1$-$C_3$ alkyl, or —SO$_2$—$R_5$; and
$R_5$ is alkyl, cycloalkyl, aryl, or heteroaryl;
or a pharmaceutically acceptable salt or a stereoisomer thereof or a combination thereof.

2. The compound of claim 1, wherein the compound is according to the following formula:

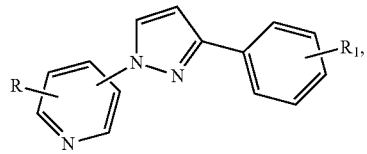

or a pharmaceutically acceptable salt or a stereoisomer thereof or a combination thereof.

3. The compound of claim 1, wherein the compound is according to the following formula:

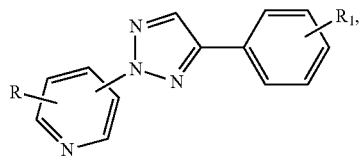

or a pharmaceutically acceptable salt or a stereoisomer thereof or a combination thereof.

4. The compound of claim 1, wherein the compound is according to the following formula:

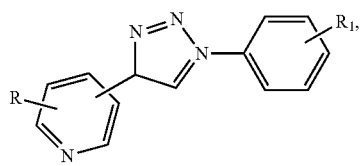

or a pharmaceutically acceptable salt or a stereoisomer thereof or a combination thereof.

5. The compound of claim 1, wherein the compound is according to the following formula:

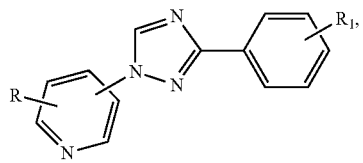

or a pharmaceutically acceptable salt or a stereoisomer thereof or a combination thereof.

6. The compound of claim 1 selected from the group consisting of

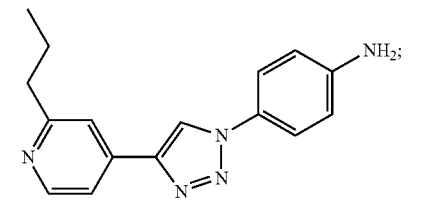

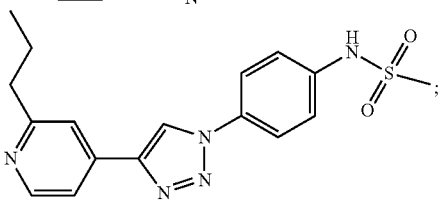

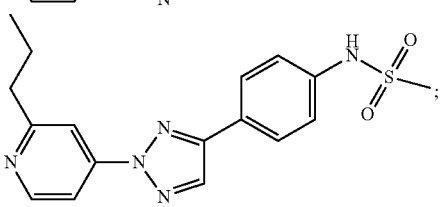

-continued

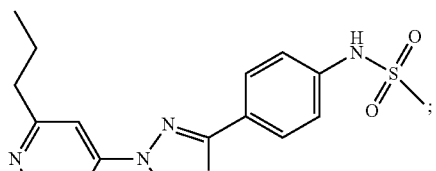

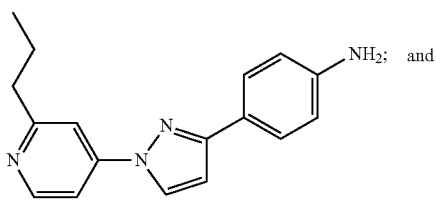

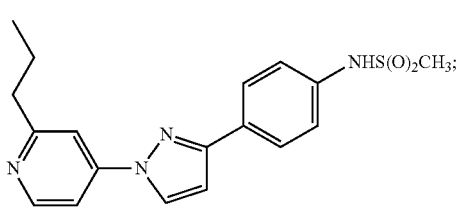

or a pharmaceutically acceptable salt thereof.

7. A compound selected from the group consisting of:

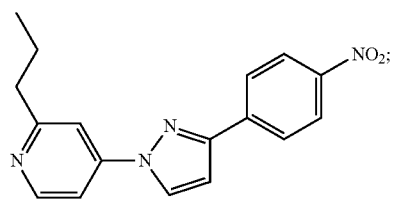

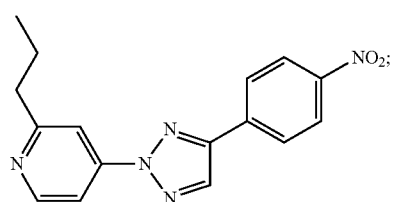

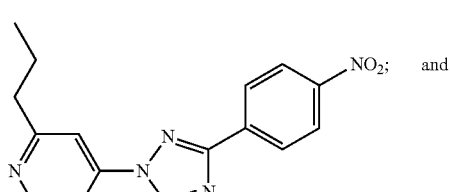

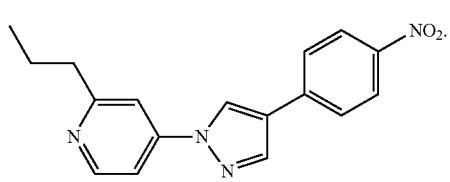

8. A compound according to the following formula:

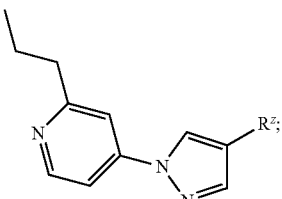

where $R^z$ is

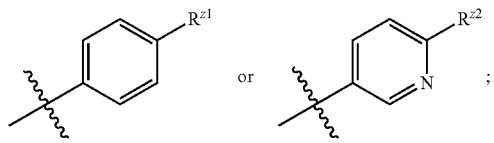

$R^{z1}$ is —NO$_2$, —NH$_2$, —NHS(O)$_2$CH$_3$,

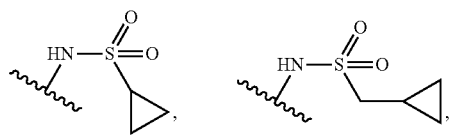 [SMILES: *NS(=O)(=O)C1CC1 ; *NS(=O)(=O)CC1CC1]

NHS(O)$_2$(isopropyl), —NH(isopropyl), or —NH(2-methylprop-1-yl); and $R^{z2}$ is —NH(isopropyl) or

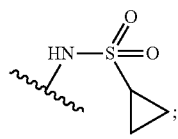 [SMILES: *NS(=O)(=O)C1CC1]

or a pharmaceutically acceptable salt thereof.

9. A method of treating a metabolic disorder in an animal in need thereof, treating a cell proliferative disease in an animal in need thereof, reducing body weight in an animal in need thereof, or increasing thermogenesis without reducing lean body mass during weight loss in an animal, comprising the step of administering to the animal a therapeutically effective amount of at least one compound according to claim 8, or a pharmaceutically acceptable salt thereof.

10. The compound according to claim 8, selected from the group consisting of:

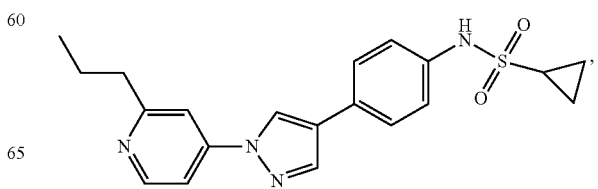

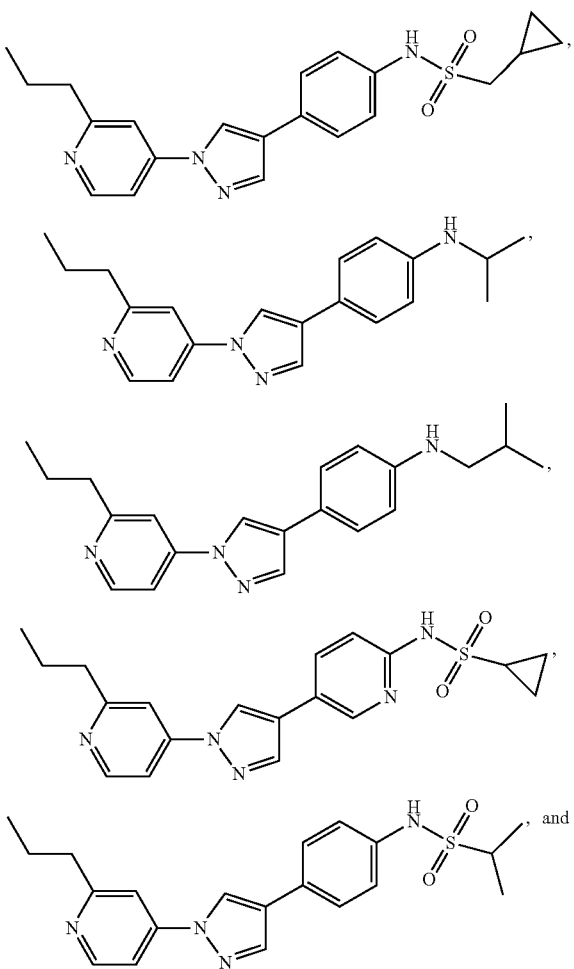

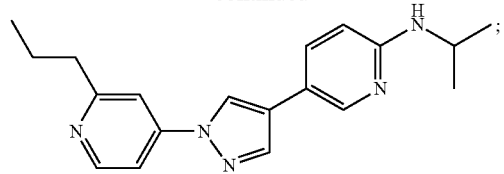

or a pharmaceutically acceptable salt thereof.

11. The method of claim 9, wherein the animal is a human.

12. The method of claim 11, wherein the cell proliferative disease is cancer.

13. The compound of claim 1, wherein $R_1$ is —OH, —O—$C_{1-3}$ alkyl, —OC(O)$R_2$, or —N$R_3R_4$.

14. A method of treating a metabolic disorder in an animal in need thereof, treating a cell proliferative disease in an animal in need thereof, reducing body weight in an animal in need thereof, or increasing thermogenesis without reducing lean body mass during weight loss in an animal, comprising the step of administering to the animal a therapeutically effective amount of at least one compound according to claim 1, or a pharmaceutically acceptable salt thereof.

15. The method of claim 14, wherein the animal is a human.

16. The method of claim 15, wherein the cell proliferative disease is cancer.

17. A method of treating a metabolic disorder in an animal in need thereof, treating a cell proliferative disease in an animal in need thereof, reducing body weight in an animal in need thereof, or increasing thermogenesis without reducing lean body mass during weight loss in an animal, comprising the step of administering to the animal a therapeutically effective amount of at least one compound according to claim 2, or a pharmaceutically acceptable salt thereof.

18. The method of claim 17, wherein the animal is a human.

19. The method of claim 18, wherein the cell proliferative disease is cancer.

* * * * *